(12) United States Patent
Budzik et al.

(10) Patent No.: US 8,288,413 B2
(45) Date of Patent: *Oct. 16, 2012

(54) BENZIMIDAZOLONES WHICH HAVE ACTIVITY AT M1 RECEPTOR

(75) Inventors: Brian Budzik, Collegeville, PA (US); David Gwyn Cooper, Harlow (GB); Ian Thomson Forbes, Harlow (GB); Jian Jin, Collegeville, PA (US); Dongchuan Shi, Collegeville, PA (US); Paul William Smith, Harlow (GB); Graham Walker, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1176 days.

This patent is subject to a terminal disclaimer.

(21) Appl. No.: 12/088,489

(22) PCT Filed: Sep. 27, 2006

(86) PCT No.: PCT/GB2006/003585
§ 371 (c)(1),
(2), (4) Date: Mar. 28, 2008

(87) PCT Pub. No.: WO2007/036711
PCT Pub. Date: Apr. 5, 2007

(65) Prior Publication Data
US 2008/0306112 A1    Dec. 11, 2008

(30) Foreign Application Priority Data

Sep. 30, 2005 (GB) .................................. 0519966.6
Feb. 13, 2006 (GB) .................................. 0602853.4

(51) Int. Cl.
*A61K 31/454* (2006.01)
*C07D 405/04* (2006.01)
(52) U.S. Cl. ...................................... 514/322; 546/199
(58) Field of Classification Search .................. 514/322; 546/199
See application file for complete search history.

(56) References Cited

U.S. PATENT DOCUMENTS

| | | | |
|---|---|---|---|
| 3,161,645 A | 12/1964 | Janssen | |
| 3,989,707 A * | 11/1976 | Janssen et al. | 546/199 |
| 4,292,321 A | 9/1981 | Pattison | |
| 4,470,989 A * | 9/1984 | Henning et al. | 514/322 |
| 5,574,044 A | 11/1996 | Thompson et al. | |
| 5,691,323 A * | 11/1997 | Thompson et al. | 514/94 |
| 5,718,912 A | 2/1998 | Thompson et al. | 514/217.06 |
| 5,977,134 A | 11/1999 | Ciccarone et al. | |
| 6,162,804 A | 12/2000 | Bilodeau et al. | |
| 6,465,484 B1 | 10/2002 | Bilodeau et al. | |
| 6,872,733 B2 | 3/2005 | Goehring et al. | |
| 6,951,849 B2 | 10/2005 | Kelly et al. | |
| 7,087,593 B2 | 8/2006 | Kelly et al. | |
| 7,598,393 B2 | 10/2009 | Kon-I et al. | |
| 7,776,885 B2 | 8/2010 | Katsu et al. | |
| 2002/0019395 A1 | 2/2002 | Zhu et al. | |
| 2003/0008886 A1 | 1/2003 | Goehring et al. | |
| 2003/0040513 A1 | 2/2003 | Baxter et al. | |
| 2003/0100545 A1 | 5/2003 | Kelly et al. | |
| 2003/0171360 A1 | 9/2003 | Gross et al. | 424/427 |
| 2004/0067931 A1 | 4/2004 | Kelly et al. | |
| 2005/0020575 A1 | 1/2005 | Cole et al. | |
| 2005/0192307 A1 | 9/2005 | Goehring et al. | |
| 2006/0025402 A1 | 2/2006 | Kelly et al. | |
| 2006/0199799 A1 | 9/2006 | Kelly et al. | |
| 2006/0205785 A1 | 9/2006 | Kelly et al. | |
| 2006/0258707 A1 | 11/2006 | Kelly et al. | |
| 2008/0103178 A1 | 5/2008 | Hashimoto et al. | |
| 2008/0255195 A1 | 10/2008 | Budzik et al. | |
| 2008/0293770 A1 | 11/2008 | Budzik et al. | |

FOREIGN PATENT DOCUMENTS

EP    0068261 A1    1/1983

(Continued)

OTHER PUBLICATIONS

Sur et al. "Seletive targting of Muscarinic . . . " Current Neuropharm. v. 3 p. 63-71 (2005).* Jassen et al. "Benzimidazolinon . . . " CA84:135657 (1976).*
Henniung et al. "N-oxazyclyl alkylpiperidine . . . " CA98:160727 (1983).*
Poulain, R., et al: "From hit to lead." Journal of Medicinal Chemistry, vol. 44 No. 21, Oct. 2001, pp. 3378-3390.

(Continued)

*Primary Examiner* — Celia Chang
(74) *Attorney, Agent, or Firm* — Linda E. Hall; John L. Lemanowicz

(57) ABSTRACT

Compounds of formula (I) and salts are provided:

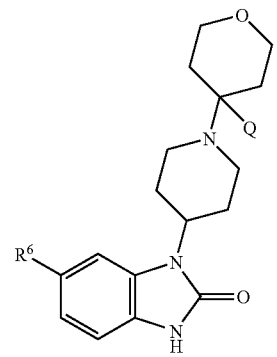

wherein $R^6$ is selected from hydrogen, halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$ alkoxy, $C_{1-6}$ alkoxy substituted with one or more fluorine atoms, and cyano, and Q is hydrogen or $C_{1-6}$alkyl. The compounds are M1 agonists and are useful for therapy, for example in the treatment of psychotic disorders and cognitive impairment.

7 Claims, No Drawings

FOREIGN PATENT DOCUMENTS

| | | |
|---|---|---|
| EP | 0 491 212 A1 | 6/1992 |
| EP | 1221443 A1 | 7/2002 |
| EP | 1386920 A1 | 2/2004 |
| EP | 1491212 A | 12/2004 |
| WO | WO96/13262 | 5/1996 |
| WO | WO96/13262 A | 5/1996 |
| WO | WO97/16186 A | 5/1997 |
| WO | WO 99/32481 | 7/1999 |
| WO | WO03/105781 A | 12/2003 |
| WO | WO 2004/054974 A | 7/2004 |
| WO | WO2004/089942 | 10/2004 |
| WO | WO2007/036711 A | 4/2007 |
| WO | WO2007/036715 A | 4/2007 |
| WO | WO2007/036718 A | 4/2007 |
| WO | WO2008/119711 | 10/2008 |
| WO | WO2008/119712 | 10/2008 |
| WO | WO2008/119713 | 10/2008 |
| WO | WO2008/119714 | 10/2008 |
| WO | WO 2008/119715 | 10/2008 |
| WO | WO2008/119716 | 10/2008 |
| WO | WO2008/119717 | 10/2008 |
| WO | WO2008/119718 | 10/2008 |
| WO | WO2008/119719 | 10/2008 |
| WO | WO2008/119720 | 10/2008 |
| WO | WO2008/119721 | 10/2008 |
| WO | WO2008/0293770 | 11/2008 |

OTHER PUBLICATIONS

Hennings, R., et al: "Synthesis and neuroleptic activity of a series of 1-[1-(benzo-1,4-dioxan-2-ylmethyl)-4-piperidinyl] benzimidazolone derivatives". Journal of Medicinal Chemistry, vol. 30, No. 5, May 1987 pp. 814-819.

Rossi, A., et al: "Benzimidazol-Derivate and verwandte Heterocyclen V. Die Kondensation von o-Phenylendiamine mit aliphatischen and alicyclischen beta-Ketoestern" Helvetica Chimica Acta, vol. 43, No. 5, Aug. 1, 1960, pp. 1298-1313.

Gustin D. J. et al: "Discovery and SAR studies of a novel series of noncovalent cathepsin S inhibitors" Bioorganic & Medicinal Chemistry Letters, vol. 15, No. 6, Mar. 15, 2005 pp. 1687-1691.

Poulain R., et al: "From hit to lead. Analyzing structure-profile relationships" Journal of Medicinal Chemistry, vol. 44, Sep. 11, 2001, pp. 3391-3401.

Burgey et al, "Benzodiazepine calcitonin gene-related peptide (CGRP) receptor antagonists: Optimization of the 4-substituted piperidine" Bioorganic & Medicinal Chemistry Letters, vol. 16, No. 19, Oct. 1, 2006 pp. 5052-5056.

* cited by examiner

BENZIMIDAZOLONES WHICH HAVE ACTIVITY AT M1 RECEPTOR

This invention relates to novel compounds, pharmaceutical compositions containing them and their use in therapy, in particular as antipsychotic agents.

Muscarinic acetylcholine receptors are members of the G protein coupled receptor superfamily which mediate the actions of the neurotransmitter acetylcholine in both the central and peripheral nervous system. Five muscarinic receptor subtypes have been cloned, $M_1$ to $M_5$. The muscarinic $M_1$ receptor is predominantly expressed in the cerebral cortex and hippocampus, although it is also expressed in the periphery e.g. exocrine glands.

Muscarinic receptors in the central nervous system, especially $M_1$, play a critical role in mediating higher cognitive processing. Diseases associated with cognitive impairments, such as Alzheimer's disease, are accompanied by loss of cholinergic neurons in the basal forebrain. Furthermore, in animal models, blockade or lesion of central cholinergic pathways results in profound cognitive deficits.

Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to side effects resulting from stimulation of peripheral muscarinic receptors including disturbed gastrointestinal motility and nausea.

The dopamine hypothesis of schizophrenia suggests that excess dopaminergic stimulation is responsible for the positive symptoms of the disease, hence the utility of dopamine receptor antagonists to reduce psychotic symptoms. However, conventional dopamine receptor antagonists can cause extrapyramidal side effects (EPS) in patients, including tremor and tardive dyskinesias.

$M_1$ receptor agonists have been sought for the symptomatic treatment of cognitive decline. More recently, a number of groups have shown that muscarinic receptor agonists display an atypical antipsychotic-like profile in a range of pre-clinical paradigms. The muscarinic agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine-induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile.

Xanomeline has also been shown to reduce psychotic symptoms such as suspiciousness, hallucinations and delusions in Alzheimer's patients. However, the relatively non-selective nature of the compound gives rise to dose-limiting peripheral cholinergic side effects.

Selective $M_1$ receptor agonists have the potential utility to ameliorate positive and cognitive symptoms of psychotic disorders such as schizophrenia, schizo-affective disorders, schizophreniform diseases, psychotic depression, mania, acute mania, paranoid and delusional disorders, and cognitive impairment including memory disorders such as Alzheimer's disease without peripheral cholinergic side effects mediated predominantly through $M_2$ and $M_3$ receptors.

$M_1$ receptor agonists may also be suitable for combination with other typical and atypical antipsychotics and other actives such as mood stabilisers, antidepressants, anxiolytics, drugs for extrapyrimidal side effects and cognitive enhancers, to provide improved treatment of psychotic disorders.

We have now found a novel group of compounds which are useful for the treatment of psychotic disorders.

In a first aspect therefore, the invention provides a compound of formula (I) or a salt or solvate thereof:

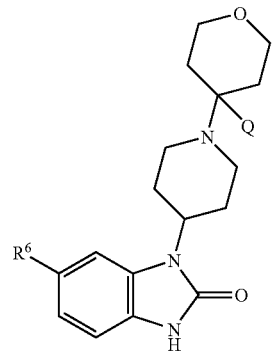

wherein:

$R^6$ is selected from hydrogen, halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$alkoxy, $C_{1-6}$alkoxy substituted with one or more fluorine atoms, and cyano, and Q is hydrogen or $C_{1-6}$alkyl.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. $C_{1-3}$alkyl means a straight or branched alkyl containing at least 1, and at most 3, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "cycloalkyl" refers to a non-aromatic hydrocarbon ring containing the specified number of carbon atoms. For example, $C_{3-6}$cycloalkyl means a non-aromatic ring containing at least three, and at most six, ring carbon atoms. Examples of "cycloalkyl" as used herein include, but are not limited to, cyclopropyl, cyclobutyl, cyclopentyl and cyclohexyl.

As used herein, the term "halogen" (or the abbreviated form "halo") refers to the elements fluorine (which may be abbreviated to "fluoro"), chlorine (which may be abbreviated to "chloro"), bromine (which may be abbreviated to "bromo") and iodine (which may be abbreviated to "iodo"). Examples of halogens are fluorine, chlorine and bromine.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. The solvent used may be water and the solvate may also be referred to as a hydrate.

As used herein, the term "substituted" refers to substitution with the named substituent or substituents, multiple degrees of substitution being allowed unless otherwise stated. For example, there may be 1, 2, 3 or 4 substituents on a given substituted group. For example, if $R^6$ is a $C_{1-6}$alkyl group, it may be substituted by 1, 2, 3 or 4 fluoro groups; and if $R^6$ is a $C_{1-6}$alkoxy group, it may be substituted by 1, 2, 3 or 4 fluoro groups. For example, $R^6$ may be a $C_{1-6}$alkyl group substituted by 3 fluoro groups; and $R^6$ may be a $C_{1-6}$alkoxy group substituted by 3 fluoro groups.

In one embodiment, $R^6$ is selected from hydrogen, halogen, $C_{1-6}$alkyl, $C_{1-6}$alkyl substituted with one, two, or three fluorine atoms, $C_{3-6}$cycloalkyl, $C_{3-6}$cycloalkyl substituted with one, two or three fluorine atoms, $C_{1-6}$alkoxy, $C_{1-6}$alkoxy substituted with one, two or three fluorine atoms, and cyano.

In one embodiment, $R^6$ is selected from hydrogen, halogen, $C_{1-4}$alkyl, $C_{1-4}$alkyl substituted with one, two or three fluorine atoms, $C_{3-6}$cycloalkyl, $C_{3-6}$cycloalkyl substituted with one, two or three fluorine atoms, $C_{1-4}$alkoxy, $C_{1-4}$alkoxy substituted with one, two or three fluorine atoms, and cyano.

In one embodiment, $R^6$ is selected from hydrogen, halogen, $C_{1-4}$alkyl, $C_{1-4}$alkyl substituted with one, two or three fluorine atoms, $C_{3-6}$cycloalkyl, $C_{1-4}$alkoxy, $C_{1-4}$alkoxy substituted with one, two or three fluorine atoms, and cyano.

In one embodiment of the invention, $R^6$ is selected from halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$alkoxy and $C_{1-6}$alkoxy substituted with one or more fluorine atoms.

In one embodiment of the invention, $R^6$ is selected from halogen, $C_{1-4}$alkyl, $C_{1-4}$alkyl substituted with one, two or three fluorine atoms, $C_{3-6}$cycloalkyl, $C_{3-6}$cycloalkyl substituted with one, two or three fluorine atoms, $C_{1-4}$alkoxy and $C_{1-4}$alkoxy substituted with one, two or three fluorine atoms.

In one embodiment, $R^6$ is selected from hydrogen, fluoro, chloro, bromo, methyl, ethyl, isopropyl, cyclopropyl, methoxy, isopropoxy, trifluoromethoxy, difluoromethoxy, $OCH_2CF_3$, trifluoromethyl, and cyano.

In one embodiment, $R^6$ is selected from hydrogen, chloro, bromo, fluoro, methyl, ethyl, isopropyl, methoxy, trifluoromethoxy and trifluoromethyl.

In one embodiment, $R^6$ is selected from chloro, bromo, methyl, ethyl, isopropyl, methoxy, trifluoromethoxy and trifluoromethyl.

In one embodiment, Q is selected from hydrogen and $C_{1-3}$alkyl. In a further embodiment, Q is selected from hydrogen, methyl, ethyl and propyl. In one embodiment, Q represents hydrogen or methyl.

In an embodiment of the invention, Q is hydrogen.

In one embodiment, the invention provides a compound of formula (Ia):

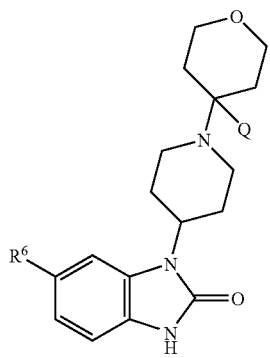

(Ia)

wherein $R^6$ is selected from hydrogen, halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$ alkoxy and $C_{1-6}$ alkoxy substituted with one or more fluorine atoms, and Q is hydrogen or $C_{1-6}$alkyl; or a pharmaceutically acceptable salt or solvate thereof.

In another embodiment, the present invention provides a compound of formula (Ib):

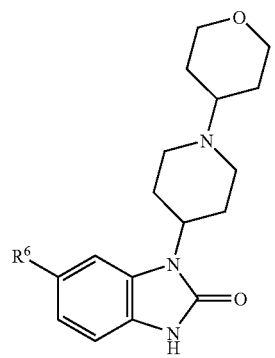

(Ib)

wherein $R^6$ is selected from hydrogen, halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$ alkoxy and $C_{1-6}$ alkoxy substituted with one or more fluorine atoms, or a pharmaceutically acceptable salt or solvate thereof.

All features and embodiments for formula (I) apply to compounds of formula (Ia) and (Ib) mutatis mutandis. Hereinafter, all references to compounds of formula (I) include compounds of formula (Ia) and compounds of formula (Ib).

It will be appreciated that for use in medicine the salts of formula (I) should be pharmaceutically acceptable. Suitable salts will be apparent to those skilled in the art and include for example acid salts, for example sodium, potassium, calcium, magnesium and tetraalkylammonium and the like, or mono- or di-basic salts formed with inorganic acids e.g. hydrochloric, hydrobromic, sulfuric, nitric or sulfamic phosphoric acid; and organic acids e.g. succinic, maleic, malic, mandelic, acetic, isethionic fumaric, glutamic, lactic, citric, tartaric, benzoic, lactobionic benzenesulfonic, p-toluenesulfonic, methanesulfonic ethanesulfonic or naphthalenesulfonic acid. Examples of salts further include trifluoroacetate salts and formate salts. Other non-pharmaceutically acceptable salts e.g. oxalates, may be used, for example in the isolation of compounds of formula (I) and are included within the scope of this invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain of the compounds of formula (I) may form acid addition salts with less than one (for example, 0.5 equivalent of a dibasic acid) or one or more equivalents of an acid. The present invention includes within its scope all possible stoichiometric and non-stoichiometric forms thereof.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

The present invention includes within the scope all pharmaceutically acceptable derivatives of the compounds of formula (I). As used herein, the term "pharmaceutically acceptable derivative", means any pharmaceutically acceptable salt, solvate, or prodrug e.g. ester, of a compound of formula (I), which upon administration to the recipient is capable of providing (directly or indirectly) a compound of formula (I), or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable protecting groups for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Suitable prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Particular compounds according to the invention include those specifically exemplified in the Examples section and named hereinafter including, without limitation:—
1-[1-(Tetrahydro-2H-pyran-4-yl)-4-piperidinyl]-1,3-dihydro-2H-benzimidazol-2-one
6-Fluoro-1-[1-(tetrahydro-2H-pyran-4-yl)-4-piperidinyl]-1,3-dihydro-2H-benzimidazol-2-one
6-Chloro-1-[1-(tetrahydro-2H-pyran-4-yl)-4-piperidinyl]-1,3-dihydro-2H-benzimidazol-2-one
6-Bromo-1-[1-(tetrahydro-2H-pyran-4-yl)-4-piperidinyl]-1,3-dihydro-2H-benzimidazol-2-one
6-Methyl-1-[1-(tetrahydro-2H-pyran-4-yl)-4-piperidinyl]-1,3-dihydro-2H-benzimidazol-2-one
6-(Methoxy)-1-[1-(tetrahydro-2H-pyran-4-yl)-4-piperidinyl]-1,3-dihydro-2H-benzimidazol-2-one
1-[1-(Tetrahydro-2H-pyran-4-yl)-4-piperidinyl]-6-(trifluoromethyl)-1,3-dihydro-2H-benzimidazol-2-one
6-Ethyl-1-[1-(tetrahydro-2H-pyran-4-yl)-4-piperidinyl]-1,3-dihydro-2H-benzimidazol-2-one
1-[1-(Tetrahydro-2H-pyran-4-yl)-4-piperidinyl]-6-[(trifluoromethyl)oxy]-1,3-dihydro-2H-benzimidazol-2-one
6-(1-Methylethyl)-1-[1-(tetrahydro-2H-pyran-4-yl)-4-piperidinyl]-1,3-dihydro-2H-benzimidazol-2-one
6-Methyl-1-[1-(4-methyltetrahydro-2H-pyran-4-yl)-4-piperidinyl]-1,3-dihydro-2H-benzimidazol-2-one
1-[1-(4-Ethyltetrahydro-2H-pyran-4-yl)-4-piperidinyl]-6-methyl-1,3-dihydro-2H-benzimidazol-2-one
6-Methyl-1-[1-(4-propyltetrahydro-2H-pyran-4-yl)-4-piperidinyl]-1,3-dihydro-2H-benzimidazol-2-one
1-[1-(4-Methyltetrahydro-2H-pyran-4-yl)piperidin-4-yl]-6-(trifluoromethoxy)-1,3-dihydro-2H-benzimidazol-2-one
6-Cyclopropyl-1-[1-(4-methyltetrahydro-2H-pyran-4-yl)-4-piperidinyl]-1,3-dihydro-2H-benzimidazol-2-one
6-Cyclopropyl-1-[1-(tetrahydro-2H-pyran-4-yl)-4-piperidinyl]-1,3-dihydro-2H-benzimidazol-2-one
6-[(1-Methylethyl)oxy]-1-[1-(tetrahydro-2H-pyran-4-yl)-4-piperidinyl]-1,3-dihydro-2H-benzimidazol-2-one
6-[(Difluoromethyl)oxy]-1-[1-(tetrahydro-2H-pyran-4-yl)-4-piperidinyl]-1,3-dihydro-2H-benzimidazol-2-one
1-[1-(Tetrahydro-2H-pyran-4-yl)-4-piperidinyl]-6-[(2,2,2-trifluoroethyl)oxy]-1,3-dihydro-2H-benzimidazol-2-one
2-Oxo-3-[1-(tetrahydro-2H-pyran-4-yl)-4-piperidinyl]-2,3-dihydro-1H-benzimidazole-5-carbonitrile
and salts and solvates thereof, for example the hydrochloride salt, the trifluoroacetate salt or the formate salt.

Specific examples of salts of the compounds of formula (I) include:
1-[1-(Tetrahydro-2H-pyran-4-yl)-4-piperidinyl]-1,3-dihydro-2H-benzimidazol-2-one trifluoroacetate
6-Fluoro-1-[1-(tetrahydro-2H-pyran-4-yl)-4-piperidinyl]-1,3-dihydro-2H-benzimidazol-2-one trifluoroacetate
6-Chloro-1-[1-(tetrahydro-2H-pyran-4-yl)-4-piperidinyl]-1,3-dihydro-2H-benzimidazol-2-one hydrochloride
6-Bromo-1-[1-(tetrahydro-2H-pyran-4-yl)-4-piperidinyl]-1,3-dihydro-2H-benzimidazol-2-one hydrochloride
6-Methyl-1-[1-(tetrahydro-2H-pyran-4-yl)-4-piperidinyl]-1,3-dihydro-2H-6-(Methoxy)-1-[1-(tetrahydro-2H-pyran-4-yl)-4-piperidinyl]-1,3-dihydro-2H-benzimidazol-2-one trifluoroacetate
1-[1-(Tetrahydro-2H-pyran-4-yl)-4-piperidinyl]-6-(trifluormethyl)-1,3-dihydro-2H-benzimidazol-2-one trifluoroacetate
6-Ethyl-1-[1-(tetrahydro-2H-pyran-4-yl)-4-piperidinyl]-1,3-dihydro-2H-benzimidazol-2-one hydrochloride
1-[1-(Tetrahydro-2H-pyran-4-yl)-4-piperidinyl]-6-[(trifluoromethyl)oxy]-1,3-dihydro-2H-benzimidazol-2-one hydrochloride
6-(1-Methylethyl)-1-[1-(tetrahydro-2H-pyran-4-yl)-4-piperidinyl]-1,3-dihydro-2H-benzimidazol-2-one hydrochloride
6-Methyl-1-[1-(4-methyltetrahydro-2H-pyran-4-yl)-4-piperidinyl]-1,3-dihydro-2H-benzimidazol-2-one hydrochloride
1-[1-(4-Ethyltetrahydro-2H-pyran-4-yl)-4-piperidinyl]-6-methyl-1,3-dihydro-2H-benzimidazol-2-one hydrochloride
6-Methyl-1-[1-(4-propyltetrahydro-2H-pyran-4-yl)-4-piperidinyl]-1,3-dihydro-2H-benzimidazol-2-one hydrochloride
1-[1-(4-Methyltetrahydro-2H-pyran-4-yl)piperidin-4-yl]-6-(trifluoromethoxy)-1,3-dihydro-2H-benzimidazol-2-one hydrochloride 6-Cyclopropyl-1-[1-(tetrahydro-2H-pyran-4-yl)-4-piperidinyl]-1,3-dihydro-2H-benzimidazol-2-one hydrochloride 6-[(1-Methylethyl)oxy]-1-[1-(tetrahydro-2H-pyran-4-yl)-4-piperidinyl]-1,3-dihydro-2H-benzimidazol-2-one hydrochloride 6-[(Difluoromethyl)oxy]-1-[1-(tetrahydro-2H-pyran-4-yl)-4-piperidinyl]-1,3-dihydro-2H-benzimidazol-2-one hydrochloride 1-[1-(Tetrahydro-2H-pyran-4-yl)-4-piperidinyl]-6-[(2,2,2-trifluoroethyl)oxy]-1,3-dihydro-2H-benzimidazol-2-one hydrochloride and 2-Oxo-3-[1-(tetrahydro-2H-pyran-4-yl)-4-piperidinyl]-2,3-dihydro-1H-benzimidazole-5-carbonitrile hydrochloride.

In a further aspect, the invention provides a general process (A1) for preparing compounds of formula (I) in which Q=H, which process comprises:

coupling a compound of formula (II)

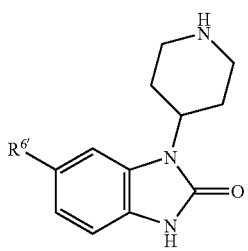

(II)

with a compound of formula (III)

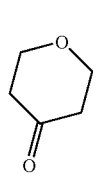

(III)

wherein $R^{6'}$ is a group $R^6$ as previously defined, or a group convertible to $R^6$.

The reaction is carried out under conditions suitable for reductive alkylation. The reductive alkylation reaction is typically carried out using sodium triacetoxyborohydride in dichloroethane, optionally in the presence of triethylamine, and optionally in the presence of titanium tetraisopropoxide. Alternatively sodium cyanoborohydride can be used as the reducing reagent in solvents such as methanol or ethanol, or the reductive alkylation can be effected under catalytic hydrogenation conditions using a palladium catalyst. In a further variation, the compounds (II) and (III) can be condensed under dehydrating conditions e.g. molecular sieves or magnesium sulfate, and the resultant imine or enamine reduced using for example sodium borohydride or by catalytic hydrogenation.

A modification of general process (A1) is required where Q=$C_{1-6}$ alkyl. Thus, in general process (A2), a compound of formula (II) can be reacted with a compound of formula (III) in the presence of a source of cyanide, e.g. acetone cyanohydrin, to form the cyano intermediate (XXXX) which can be reacted with an alkyl Grignard reagent QMgX to form compounds of formula (I).

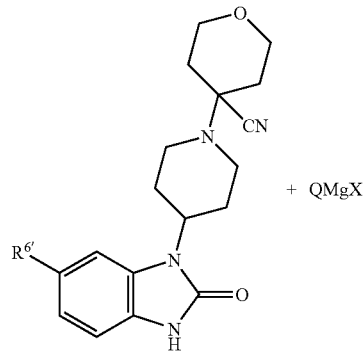

(XXXX)

+ QMgX wherein $R^{6'}$ is a group $R^6$ as previously defined, or a group convertible to $R^6$, Q is as previously defined, and X is chloro, bromo or iodo.

The reaction is carried out using conditions similar to those described in the literature (Arch Pharm (Weinheim), 1987, 320 (4), 348-361). The piperidine and ketone components are treated with potassium cyanide in water at pH3 or reacted with acetone cyanohydrin in dimethyl acetamide at elevated temperature to form the adduct (XXXX). Reaction of the adduct (XXXX) with the alkyl Grignard reagent QMgX in ether or tetrahydrofuran provides compounds of formula (I).

In a further aspect, the invention provides a general process (B) for preparing compounds of formula (I) which process comprises:

coupling a compound of formula (IV)

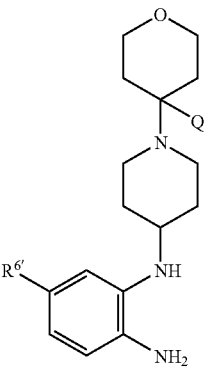

(IV)

with a compound of formula (V)

(V)

wherein $R^{6'}$ is a group $R^6$ as previously defined, or a group convertible to $R^6$, Q is as previously defined, and X and Y both represent leaving groups. X and Y can be the same or different and examples are Cl, PhO, EtO, imidazole. When X and Y are both Cl, i.e. phosgene, this reagent can be generated in situ e.g. from diphosgene or triphosgene.

The above reaction is carried out using standard methodology e.g. reacting the diamine (IV) with the reagent (V) in an inert solvent for example dichloromethane or toluene or dimethylformamide, optionally in the presence of a base such as triethylamine or potassium carbonate, and optionally with heating.

In a further aspect, the invention provides a general process (C) for preparing compounds of formula (I) which process comprises:
treatment of a compound of formula (VI)

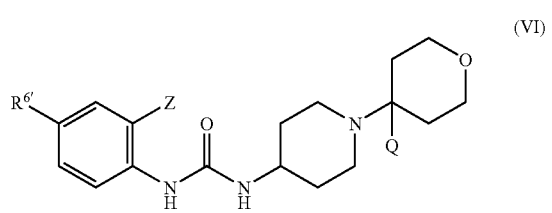

(VI)

with a palladium or copper catalyst (VII) to effect an intramolecular cyclisation
wherein $R^{6'}$ is a group $R^6$ as previously defined, or a group convertible to $R^6$, Q is as previously defined, and Z is a leaving group such as bromo, iodo, chloro or triflate.

The cyclisation reaction can be carried out using a variety of palladium or copper reagents as described in the literature (JACS, 2003, 125, 6653, Tet. Lett., 2004, 45, 8535, or JACS, 2002, 124, 7421.)

In a further aspect, the invention provides a general process (D) for preparing compounds of formula (I) which process comprises:
coupling a compound of formula (VIII)

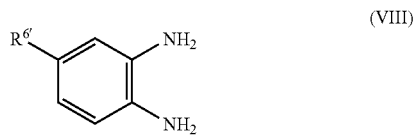

(VIII)

with a compound of formula (IX)

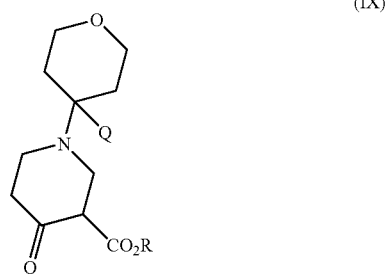

(IX)

wherein $R^{6'}$ is a group $R^6$ as previously defined, or a group convertible to $R^6$, Q is as previously defined, and R is a $C_{1-5}$ alkyl group.

These condensation and cyclisation reactions can be carried out under reaction conditions similar to those described in the literature for an analogous process (U.S. Pat. No. 3,161,645) (for example heating in an inert solvent such as xylene) followed by reduction of the piperidine double bond using for example catalytic hydrogenation over palladium or Raney nickel.

In a further aspect, the invention provides a general process (E) for preparing compounds of formula (I) which process comprises:
reaction of a compound of formula (X)

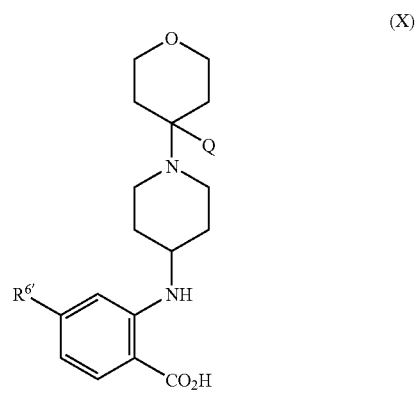

(X)

with diphenylphosphoryl azide or other reagent/combination of reagents to effect the Curtius rearrangement of compound (X), followed by intramolecular cyclisation.
wherein $R^{6'}$ is a group $R^6$ as previously defined, or a group convertible to $R^6$, and Q is as previously defined.

The Curtius rearrangement is typically carried out by mixing the two reactants in an inert solvent such as toluene, optionally with heating.

In a further aspect, the invention provides a general process (F) for preparing compounds of formula (I) which process comprises:
coupling a compound of formula (XI)

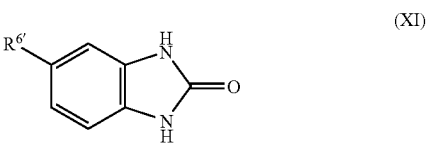

(XI)

with a compound of formula (XII)

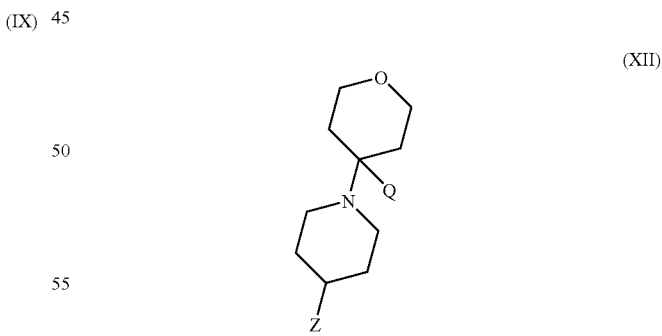

(XII)

wherein $R^{6'}$ is a group $R^6$ as previously defined, or a group convertible to $R^6$, Q is as previously defined, and Z is hydroxy or a leaving group such as chloro, bromo or iodo, or alkyl/aryl sulfonate.

The alkylation reaction (Z=a leaving group) can be carried out under classical alkylation or Mitsunobu reaction (Z=OH) conditions. Using classical alkylation conditions, the benzimidazolone intermediate (XI) can be deprotonated using a base such as sodium hydride in an inert solvent such as dimethylformamide, and then treated with the alkylating reagent (XII), optionally with heating. The Mitsunobu reaction with (XII) Z=OH can be carried out using standard conditions e.g. triphenylphosphine and diethylazodicarboxylate in an inert solvent such as dichloromethane or tetrahydrofuran at room temperature Conversion of $R^{6'}$ to $R^6$ or interconversions of $R^6$ may be accomplished as indicated below.

For example, when $R^{6'}$ is a halogen, it can be converted to an alkoxy or trifluoromethyl group by copper catalysed reaction, using an alcohol, or methyl fluorosulfonyl(difluoro) acetate, respectively. It may also be converted to an alkyl group with an organometallic reagent, for example an alkylstannane.

As another example, when $R^{6'}$ is hydroxy, it may be converted to alkoxy by reaction with an alkyl halide or sulfonate, or to trifluoromethoxy by conversion to the xanthate followed by oxidation in the presence of fluoride ion.

As a further example, when $R^{6'}$ is methyl, it may be converted to trifluoromethyl by chlorination or bromination followed by displacement of the introduced halogens with fluoride.

Compounds of formula (II) are generally known in the literature or can be prepared by a range of different processes for example:

(a) displacement of an ortho-fluoro or ortho-chloro nitrobenzene intermediate (XIII) with the amine (XIV), wherein $R^{6'}$ is a group $R^6$ as previously defined, or a group convertible to $R^6$, and P represents a nitrogen protecting group e.g. Boc, acetyl, trifluoroacetyl, ethoxycarbonyl, benzyloxycarbonyl, to give (XXIII), followed by reduction of the nitro group, cyclisation using phosgene or a phosgene equivalent, and deprotection of the piperidine nitrogen using standard literature conditions (Scheme 1).

Scheme 1.

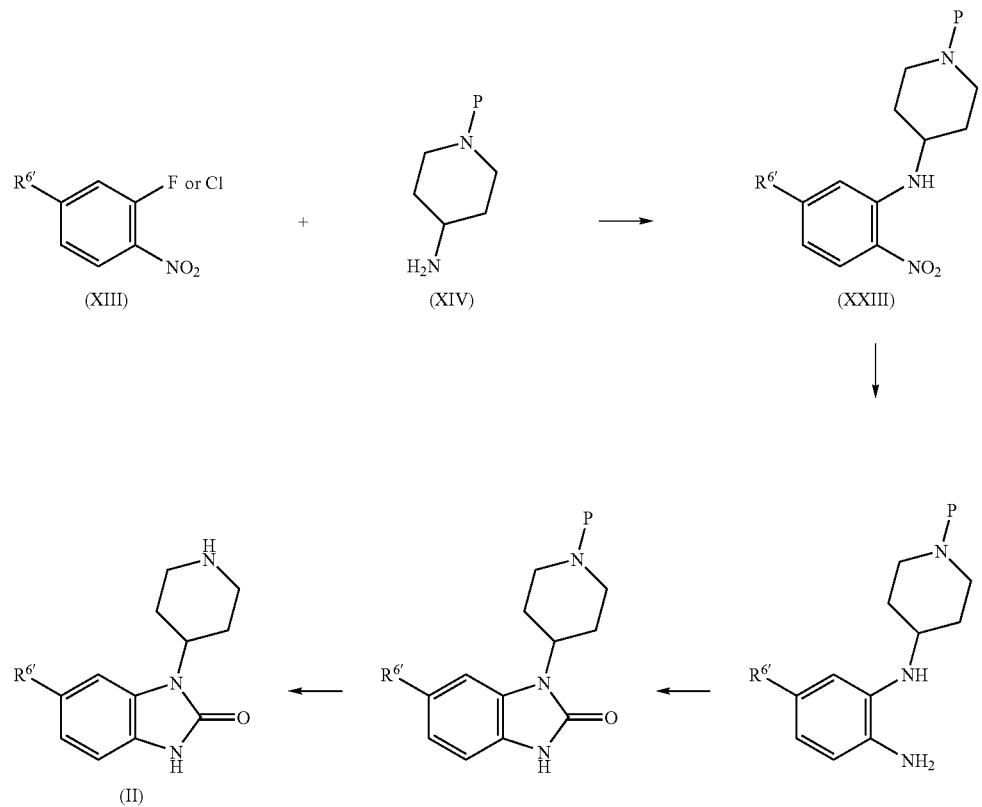

Compounds of formula (XIII) are commercially available or can be prepared by standard methodology. The compound (XIV) in which P=Boc is commercially available (b) metal catalysed cyclisation of an intermediate (XV) followed by deprotection of the piperidine nitrogen, wherein $R^{6'}$ is a group $R^6$ as previously defined, or a group convertible to $R^6$, P represents a nitrogen protecting group e.g. Boc, acetyl, trifluoroacetyl, benzyloxycarbonyl, and Z represents a leaving group such as bromo, iodo, chloro or triflate. Reaction conditions for the Buchwald cyclisation are summarised in Process C. The urea (XV) can be prepared using any of the classical methods for urea formation as illustrated in Scheme 2. The starting materials for this process are commercially available or can be prepared using standard methodology.

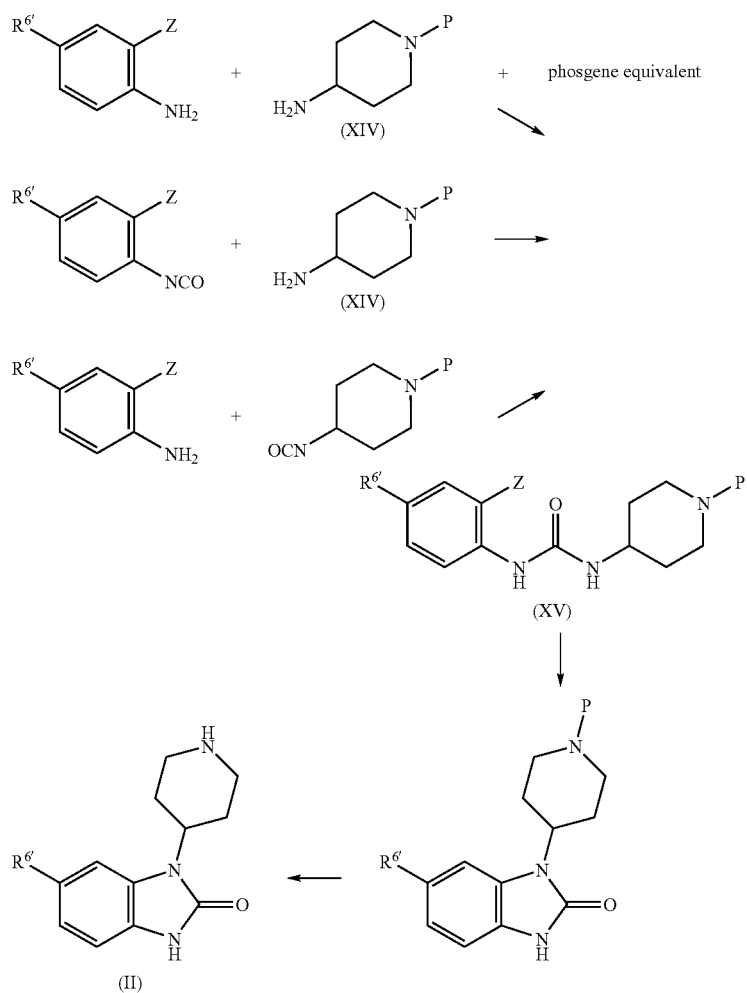

(c) Curtius rearrangement of an intermediate (XVI), wherein $R^{6'}$ is a group $R^6$ as previously defined, or a group convertible to $R^6$, P represents a nitrogen protecting group e.g. Boc, acetyl, trifluoroacetyl, benzyloxycarbonyl, and R represents H or a C1-5 alkyl group e.g. methyl or ethyl, followed by intramolecular cyclisation and deprotection of the piperidine nitrogen (Scheme 3). The anthranilic acid or ester starting materials (XVII) are commercially available or can be made by standard methodology. The piperidone starting material (R=Boc or benzyl) is commercially available. The Curtius rearrangement can be effected using the conditions described under process E.

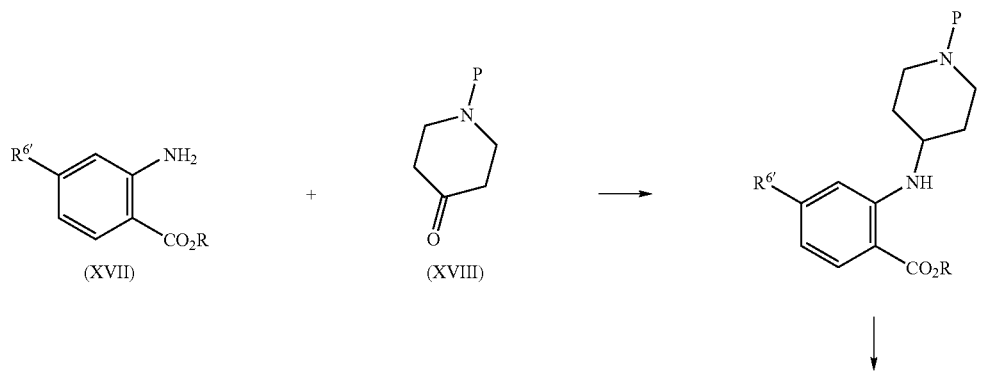

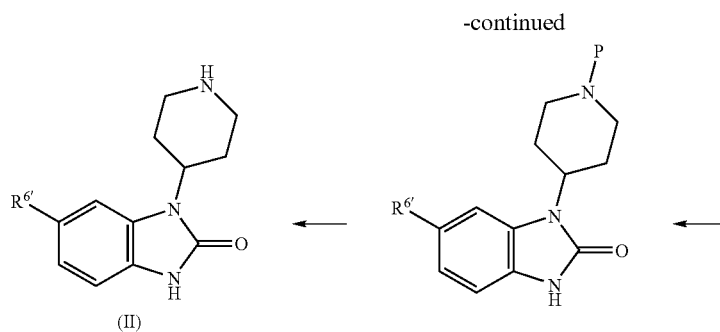

(II)   (XVI)

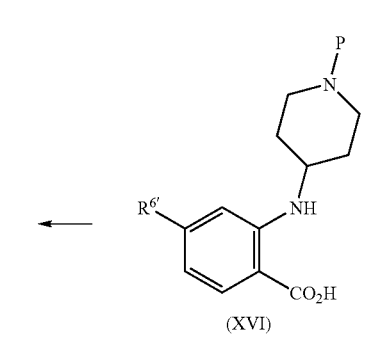

-continued

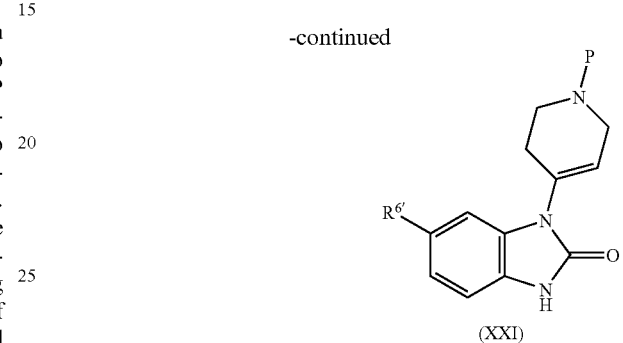

(XXI)

(d) Condensation of an orthophenylenediamine (VIII) with a 3-alkoxycarbonyl-4-piperidone (XX), wherein $R^{6'}$ is a group $R^6$ as previously defined, or a group convertible to $R^6$, P represents a nitrogen protecting group e.g. Boc, acetyl, trifluoroacetyl, benzyloxycarbonyl and R is a C1-5 alkyl group (Scheme 4), by heating in an inert solvent at elevated temperature, to afford the tetrahydropyridine intermediate (XXI). Hydrogenation of the double bond and deprotection of the piperidine nitrogen can be accomplished separately or concomitantly dependent on the precise nature of the protecting group P, to afford the desired product (II). Compounds of formula (VIII) are commercially available or can be prepared by standard methodology. Compounds of formula (XX) are commercially available or can be prepared by standard methodology.

(II)

(e) Reductive alkylation of an ortho nitroaniline (XXII) with an N-protected 4-piperidone (XVIII), wherein $R^{6'}$ is a group $R^6$ as previously defined, or a group convertible to $R^6$, and P represents a nitrogen protecting group e.g. Boc, acetyl, trifluoroacetyl, benzyloxycarbonyl, using for example sodium triacetoxyborohydride to give the intermediate (XXIII). Reduction of the nitro group, followed by cyclisation and deprotection as described hereinbefore provides the desired product (II) (Scheme 5). Compounds of formula (XXII) and (XVIII) are commercially available or can be prepared by standard methodology Scheme 4.

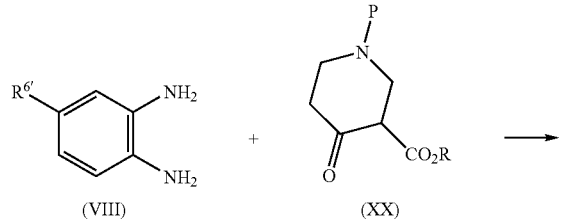

(VIII)   (XX)

Scheme 5.

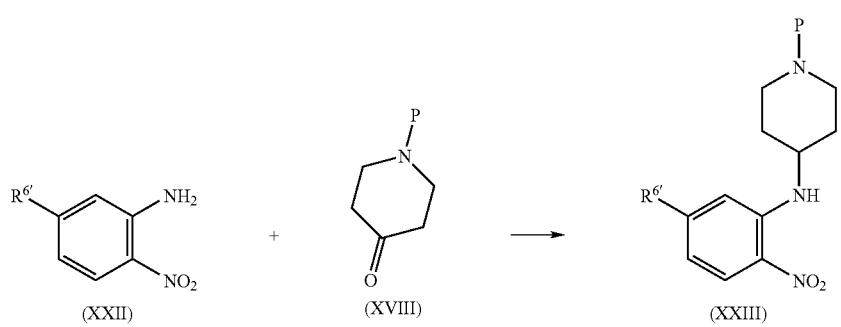

(XXII)   (XVIII)   (XXIII)

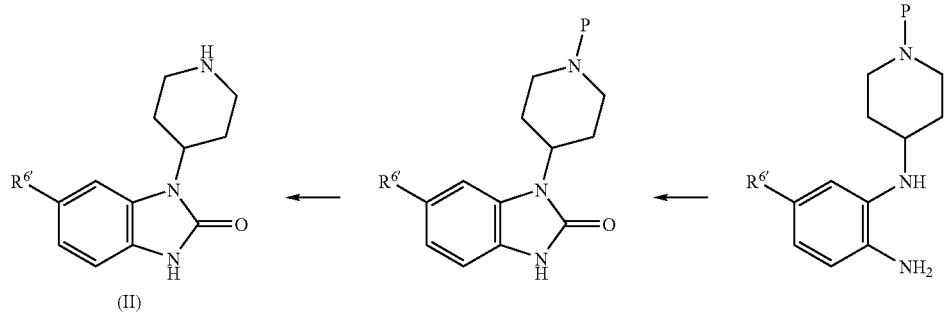

(f) metal catalysed reaction between the amine (XIV) and a suitably substituted nitrobenzene compound (XXIV) wherein $R^{6'}$ is a group $R^6$ as previously defined, or a group convertible to $R^6$, P represents a nitrogen protecting group e.g. Boc, acetyl, trifluoroacetyl, benzyloxycarbonyl, and Z represents a leaving group such as bromo, iodo, chloro or triflate (Scheme 6). This process generates intermediates of formula (XXIII) and subsequent reactions are similar to that for Scheme 5. Compounds of formula (XXIV) are commercially available or can be prepared by known methodology. The compound (XIV) in which P=Boc is commercially available

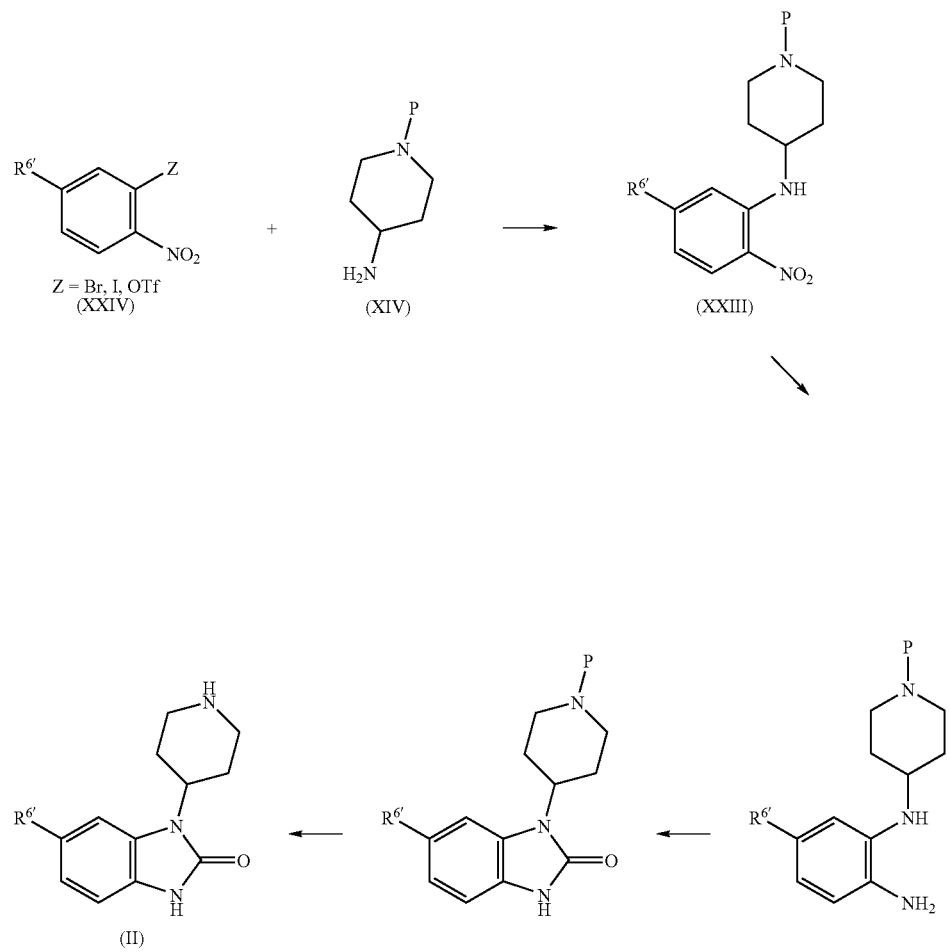

Scheme 6.

(g) metal catalysed reaction between the amine (XIV) and the protected aniline (XXV), wherein R⁶' is a group R⁶ as previously defined, or a group convertible to R⁶, P represents a nitrogen protecting group e.g. Boc, acetyl, trifluoroacetyl, benzyloxycarbonyl, and Z represents a leaving group such as bromo, iodo, chloro or triflate, to give the intermediate (XXVI) (Scheme 7). Deprotection of the aniline followed by the same reaction sequence as in Scheme 6 affords the desired intermediate (II). Compounds of formula (XXV) are commercially available or can be prepared by known methodology e.g. halogenation ortho to the aniline group. The compound (XIV) in which P=Boc is commercially available Scheme 7.

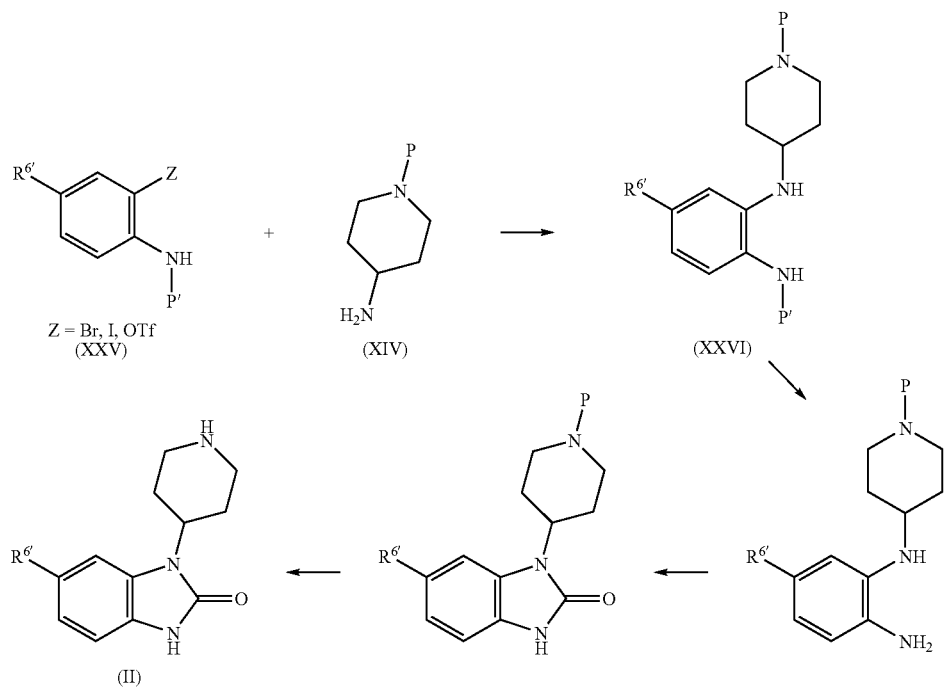

The compound of formula (III) is commercially available.

Compounds of formula (IV) can be prepared by a number of different processes e.g.

(h) displacement of an ortho-fluoro or ortho-chloro nitrobenzene intermediate (XIII) with the amine (XXVII) to afford compound (XXVIII) followed by reduction of the nitro group using standard conditions e.g. hydrogenation over palladium or Raney nickel (Scheme 8). Compounds of formula (XIII) are commercially available or can be prepared by standard methodology.

Scheme 8.

-continued

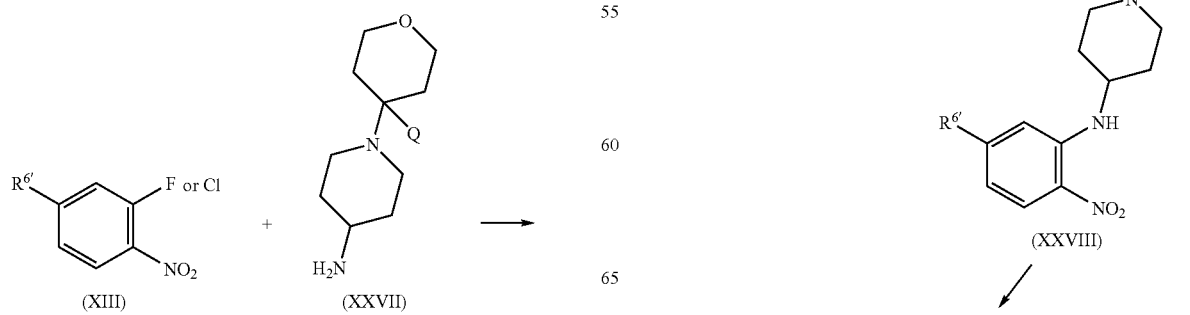

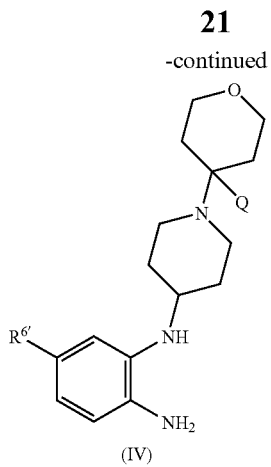

(IV)

(i) metal catalysed reaction of the amine (XXVII) with the ortho substituted nitrobenzene (XXIX) to afford compound (XXVIII) (Scheme 9) followed by the same reactions as illustrated in Scheme 8. Compounds of formula (XXIX) are commercially available or can be prepared by standard methodology.

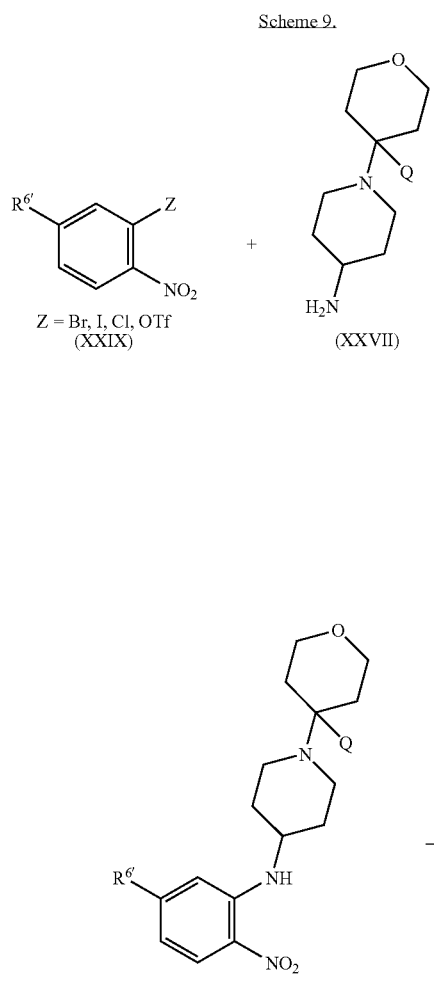

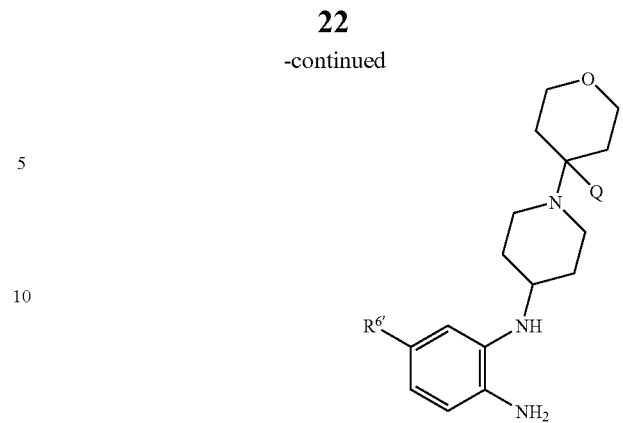

(IV)

(j) metal catalysed reaction of the amine (XXVII) with the protected aniline derivative (XXV), where P represents a nitrogen protecting group such as acetyl, trifluoroacetyl, Boc, phthalimide, to afford compound (XXXI) (Scheme 10) followed by deprotection of the aniline group. Compounds of formula (XXV) are commercially available or can be prepared by standard methodology.

Scheme 10.

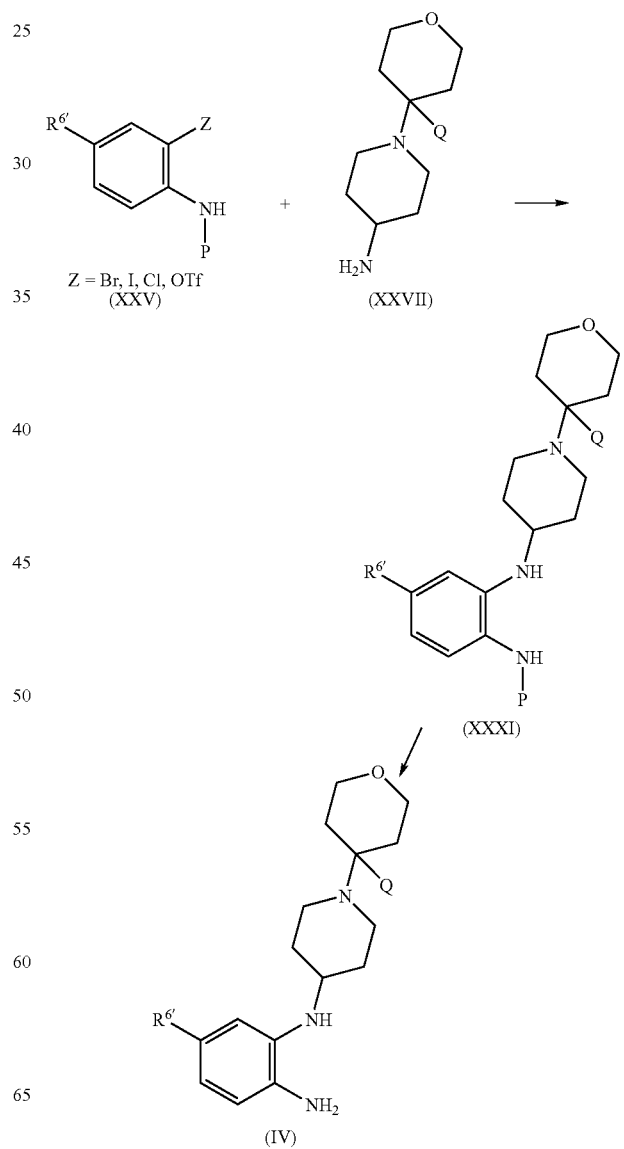

etoxyborohydride in dichloroethane to give the intermediate (XXVIII) (Scheme 11). Reduction of the nitro group using, for example, palladium on carbon or Raney nickel affords the desired intermediate (IV)

Scheme 11.

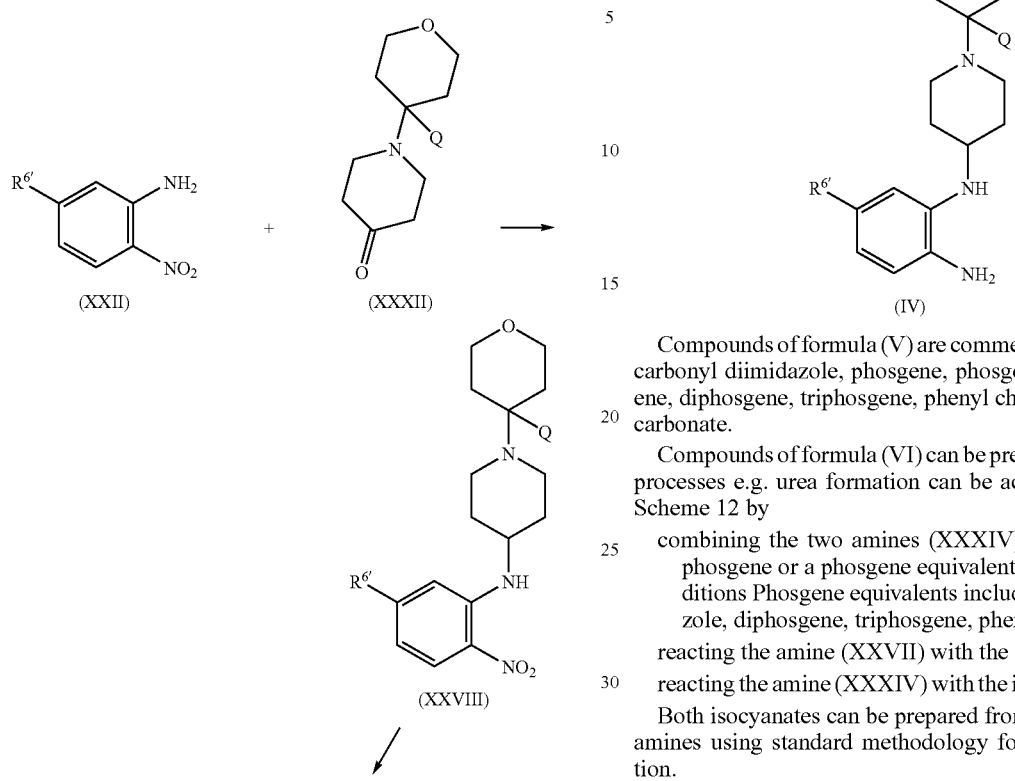

Compounds of formula (V) are commercially available e.g. carbonyl diimidazole, phosgene, phosgene solution in toluene, diphosgene, triphosgene, phenyl chloroformate, diethyl carbonate.

Compounds of formula (VI) can be prepared by a variety of processes e.g. urea formation can be achieved as shown in Scheme 12 by combining the two amines (XXXIV) and (XXVII) with phosgene or a phosgene equivalent using standard conditions Phosgene equivalents include carbonyl diimidazole, diphosgene, triphosgene, phenyl chloroformate reacting the amine (XXVII) with the isocyanate (XXXV)

reacting the amine (XXXIV) with the isocyanate (XXXVI)

Both isocyanates can be prepared from the corresponding amines using standard methodology for isocyanate formation.

Scheme 12.

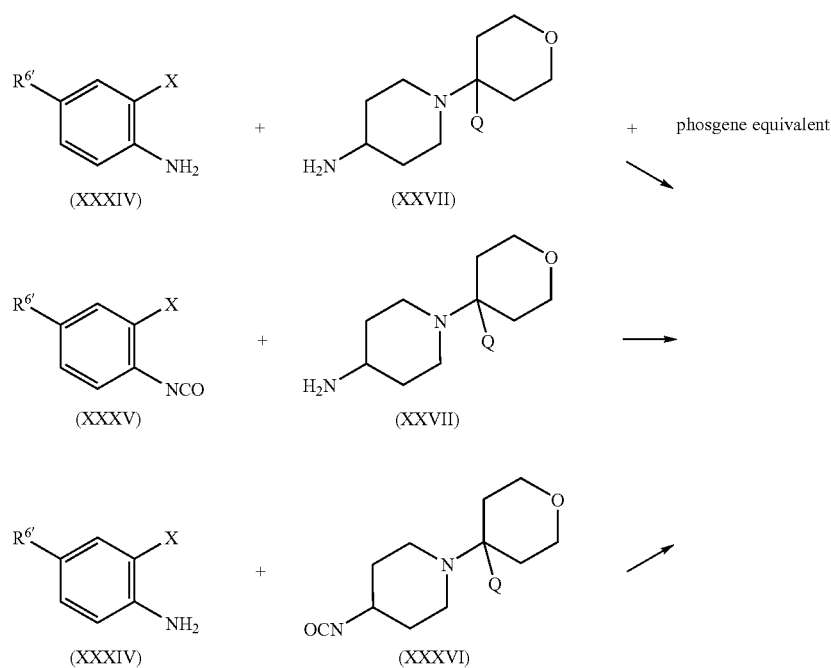

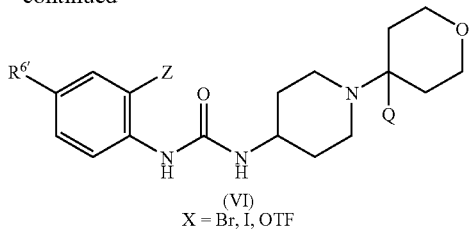

(VI)
X = Br, I, OTF

Palladium and copper catalysts (VII) are commercially available or can be prepared as described in the literature (see references in Process C).

Compounds of formula (VIII) are commercially available or can be prepared by known literature routes e.g. reduction of a mono or dinitrobenzene precursor.

Compounds of formula (IX) can be prepared by reductive alkylation of the 3-alkoxycarbonyl-4-piperidone with tetrohydropyran-4-one.

Compounds of formula (X) can be prepared as shown in Scheme 13. Reductive alkylation of an anthranilic acid or ester (XVII) with the ketone (XXXII), followed if appropriate by hydrolysis of the ester group.

Scheme 13.

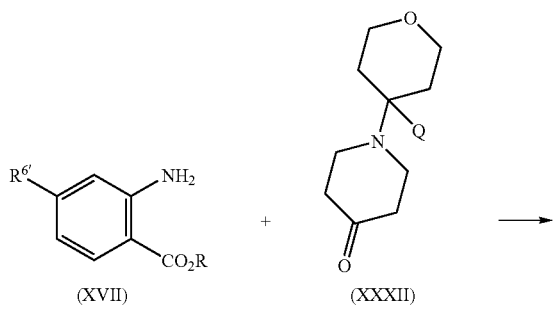

(XVII)     (XXXII)

→

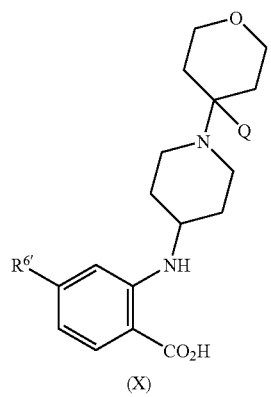

(X)

Compounds of formula (XI) are commercially available or can be prepared by literature processes.

Compounds of formula (XII) where Q=H can be prepared as shown in Scheme 14, by reductive alkylation of (XXXVII) where Z' represents Z or a group convertible to Z with the ketone (III). Conversion of a Z' hydroxy group to Z=chloro or bromo can be accomplished using standard methodology e.g. treatment with thionyl chloride or triphenylphosphine/carbon tetrabromide.

Scheme 14.

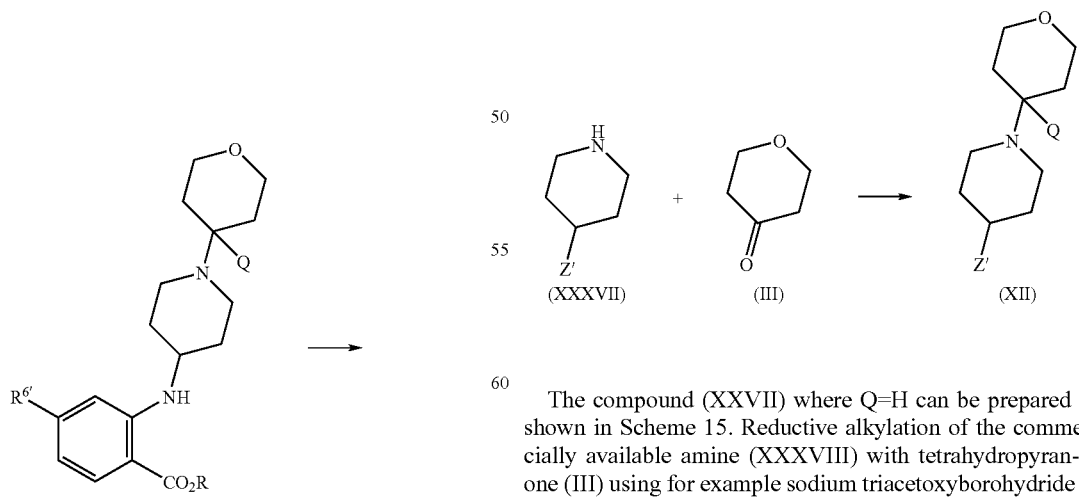

(XXXVII)     (III)     (XII)

The compound (XXVII) where Q=H can be prepared as shown in Scheme 15. Reductive alkylation of the commercially available amine (XXXVIII) with tetrahydropyran-4-one (III) using for example sodium triacetoxyborohydride in dichloroethane provides the intermediate (XXXIX) which is deprotected using HCl in ethanol or trifluoroacetic acid to afford the primary amine (XXVII).

Scheme 15.

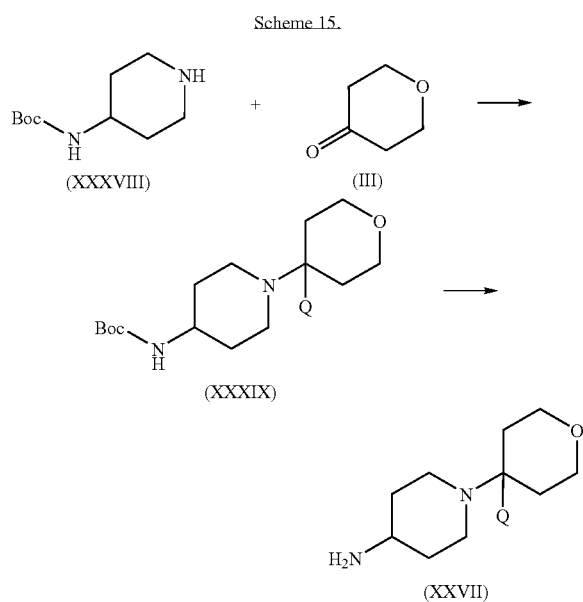

The compounds of formula (I) are of use in the treatment of psychotic disorders or cognitive impairment.

The compounds of formula (I) are expected to be useful in the treatment of psychotic disorders or cognitive impairment.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term psychotic disorder includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9);

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-induced Mood Disorder (including the subtypes With Depressive Features, With Manic Features and With Mixed Features) and Mood Disorder Not Otherwise Specified (296.90);

Anxiety disorders including Social Anxiety Disorder, Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-induced Anxiety Disorder and Anxiety Disorder Not Otherwise Specified (300.00);

Substance-related disorders including Substance Use Disorders such as Substance Dependence, Substance Craving and Substance Abuse; Substance-Induced Disorders such as Substance Intoxication, Substance Withdrawal, Substance-induced Delirium, Substance-induced Persisting Dementia, Substance-Induced Persisting Amnestic Disorder, Substance-Induced Psychotic Disorder, Substance-Induced Mood Disorder, Substance-Induced Anxiety Disorder, Substance-induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-induced Anxiety Disorder, Amphetamine-Induced Sexual Dysfunction, Amphetamine-induced Sleep Disorder and Amphetamine-Related Disorder Not Otherwise Specified (292.9); Caffeine Related Disorders such as Caffeine Intoxication (305.90), Caffeine-induced Anxiety Disorder, Caffeine-induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-induced Psychotic Disorder, Hallucinogen-Induced Mood Disorder, Hallucinogen-induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide;

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-induced Sleep Disorder including the subtypes Insomnia Type, Hypersomnia Type, Parasomnia Type and Mixed Type;

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50);

Autistic Disorder (299.00); Attention-Deficit/Hyperactivity Disorder including the subtypes Attention-Deficit/Hyperactivity Disorder Combined Type (314.01), Attention-Deficit/ Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23);

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9); and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of Formula (I) are also expected to be useful for the enhancement of cognition, including both the treatment of cognitive impairment on its own and the treatment of cognition impairment in other diseases such as schizophrenia, bipolar disorder, depression, other psychiatric disorders and psychotic conditions associated with cognitive impairment.

Within the context of the present invention, the term cognitive impairment includes, for example, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

The therapy of the present invention may also be used as a memory and/or cognition enhancer in healthy humans with no cognitive and/or memory deficit.

In a further aspect therefore, the invention provides a compound of formula (I) as hereinbefore described or a salt or solvate thereof for use in therapy.

In another aspect, the invention provides a compound of formula (I) or a salt or solvate thereof for use in the treatment of a condition which requires agonism of a muscarinic $M_1$ receptor.

In another aspect, the invention provides a compound of formula (I) as hereinbefore described or a salt or solvate thereof for use in the treatment of a psychotic disorder. The invention also provides a compound of formula (I) as hereinbefore described or a salt or solvate thereof for use in the treatment of cognitive impairment.

In another aspect, the invention provides the use of a compound of formula (I) as hereinbefore described or a salt or solvate thereof in the manufacture of a medicament for the treatment of a condition which requires agonism of a muscarinic $M_1$ receptor.

In another aspect, the invention provides the use of a compound of formula (I) as hereinbefore described or a salt or solvate thereof in the manufacture of a medicament for the treatment of a psychotic disorder. The invention also provides the use of a compound of formula (I) as hereinbefore described or a salt or solvate thereof in the manufacture of a medicament for the treatment of cognitive impairment.

In another aspect, the invention provides a method of treating a condition which requires agonism of a muscarinic $M_1$ receptor, which comprises administering to a mammal in need thereof an effective amount of a compound of formula (I) as hereinbefore described or a salt or solvate thereof.

In another aspect, the invention provides a method of treating a psychotic disorder which comprises administering to a mammal in need thereof an effective amount of a compound of formula (I) as hereinbefore described or a salt or solvate thereof. The invention also provides a method of treating cognitive impairment, which comprises administering to a mammal in need thereof an effective amount of a compound of formula (I) as hereinbefore described or a salt or solvate thereof.

The compounds of formula (I) and their salts and solvates thereof may also be suitable for combination with other actives, such as typical and atypical antipsychotics, mood stabilisers, antidepressants, anxiolytics, drugs for extrapyrimidal side effects and cognitive enhancers to provide improved treatment of psychotic disorders.

The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) or a salt or solvate thereof and at least one antipsychotic agent, a mood stabiliser, an antidepressant, an anxiolytic, a drug for extrapyrimidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a salt or solvate thereof may be administered as adjunctive therapeutic treatment to patients who are receiving administration of at least one antipsychotic agent, a mood stabiliser, an antidepressant, an anxiolytic, a drug for extrapyrimidal side effects or a cognitive enhancer, but the scope of the invention also includes the adjunctive therapeutic administration of at least one antipsychotic agent, a mood stabiliser, an antidepressant, an anxiolytic, a drug for extrapyrimidal side effects or a cognitive enhancer to patients who are receiving administration of compounds of formula (I) or a salt or solvate thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of compounds of formula (I) or a salt or solvate thereof to a patient receiving therapeutic administration of at least one antipsychotic agent. In a further aspect, the invention provides the use of compounds of formula (I) or a salt or solvate thereof in the manufacture of a medicament for adjunctive therapeutic administration for the treatment of a psychotic disorder in a patient receiving therapeutic administration of at least one antipsychotic agent. The invention further provides compounds of formula (I) or a salt or solvate thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I) or a salt or solvate thereof. In a further aspect, the invention provides the use of at least one antipsychotic agent in the manufacture of a medicament for adjunctive therapeutic administration for the treatment of a psychotic disorder in a patient receiving therapeutic administration of compounds of formula (I) or a salt or solvate thereof. The invention further provides at least one antipsychotic agent for adjunctive therapeutic administration for the treatment of a psychotic disorder in a patient receiving therapeutic administration of compounds of formula (I) or a salt or solvate thereof.

In a further aspect, the invention provides a method of treatment of a psychotic disorder by simultaneous therapeutic administration of compounds of formula (I) or a salt or solvate thereof in combination with at least one antipsychotic agent. The invention further provides the use of a combination of compounds of formula (I) or a salt or solvate thereof and at least one antipsychotic agent in the manufacture of a medicament for simultaneous therapeutic administration in the treatment of a psychotic disorder. The invention further provides the use of compounds of formula (I) or a salt thereof in the manufacture of a medicament for simultaneous therapeutic administration with at least one antipsychotic agent in the treatment of a psychotic disorder. The invention further provides compounds of formula (I) or a salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) or a salt thereof in the treatment of a psychotic disorder.

In a further aspect, the invention provides a kit-of-parts for use in the treatment of a psychotic disorder comprising a first dosage form comprising compounds of formula (I) or a salt or solvate thereof and one or more further dosage forms each comprising a antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyrimidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyrimidal side effects and a cognitive enhancer in the manufacture of a medicament for adjunctive therapeutic administration for the treatment of a psychotic disorder in a patient receiving therapeutic administration of a compound of the present invention.

The invention also provides the use of an active ingredient selected from the group consisting of: a mood stabiliser, an antidepressant, an anxiolytic, a drug for extrapyrimidal side effects and a cognitive enhancer for adjunctive therapeutic administration for the treatment of a psychotic disorder in a patient receiving therapeutic administration of a compound of the present invention In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyrimidal side effects and a cognitive enhancer.

The invention further provides the use of a combination of a compound of the present invention and an active ingredient selected from the group consisting of: a mood stabiliser, an antidepressant, an anxiolytic, a drug for extrapyrimidal side effects and a cognitive enhancer in the manufacture of a medicament for simultaneous therapeutic administration in the treatment of a psychotic disorder.

The invention further provides the use of a combination of a compound of the present invention and an active ingredient selected from the group consisting of: a mood stabiliser, an antidepressant, an anxiolytic, a drug for extrapyrimidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides the use of an active ingredient selected from the group consisting of: a mood stabiliser, an antidepressant, an anxiolytic, a drug for extrapyrimidal side effects and a cognitive enhancer in the manufacture of a medicament for simultaneous therapeutic administration with a compound of the present invention in the treatment of a psychotic disorder.

The invention further provides the use of an active ingredient selected from the group consisting of: a mood stabiliser, an antidepressant, an anxiolytic, a drug for extrapyrimidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyrimidal side effects and a cognitive enhancer for simultaneous therapeutic administration.

Examples of antipsychotic drugs that may be useful in the present invention include, but are not limited to: sodium channel blockers; mixed 5HT/dopamine receptor antagonists; mGluR5 positive modulators; D3 antagonists; 5HT6 angatonists; nicotinic alpha-7 modulators; glycine transporter GlyT1 inhibitors; D2 partial agonist/D3 antagonist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs that may be suitable for use in the present invention are as follows: clozapine (available under the tradename CLOZARIL®, from Mylan, Zenith Goldline, UDL, Novartis); olanzapine (available under the tradename ZYPREXA®, from Lilly; ziprasidone (available under the tradename GEODON®, from Pfizer); risperidone (available under the tradename RISPERDAL®, from Janssen); quetiapine fumarate (available under the tradename SEROQUEL®, from AstraZeneca); sertindole (available under the tradename SERLECT®); amisulpride (available under the tradename SOLION®, from Sanofi-Synthelabo); haloperidol (available under the tradename HALDOL®, from Ortho-McNeil); haloperidol decanoate (available under the tradename HALDOL Decanoate®); haloperidol lactate (available under the tradenames HALDOL® and INTENSOL®); chlorpromazine (available under the tradename THORAZINE®, from SmithKline Beecham (GSK); fluphenazine (available under the tradename PROLIXIN®, from Apothecon, Copley, Schering, Teva, and American Pharmaceutical Partners, Pasadena); fluphenazine decanoate (available under the tradename PROLIXIN Decanoate®); fluphenazine enanthate (available under the tradename PROLIXIN®); fluphenazine hydrochloride (available under the tradename PROLIXIN®); thiothixene (available under the tradename NAVANE®; from Pfizer); thiothixene hydrochloride (available under the tradename NAVANE®); trifluoperazine (10-[3-(4-methyl-1-piperazinyl)propyl]-2-(trifluoromethyl)phenothiazine dihydrochloride, available under the tradename STELAZINE®, from SmithKline Beckman; perphenazine (available under the tradename TRILAFON®; from Schering); perphenazine and amitriptyline hydrochloride (available under the tradename ETRAFON TRILAFON®); thioridazine (available under the tradename MELLARIL®; from Novartis, Roxane, HiTech, Teva, and Alpharma); molindone (available under the tradename MOBAN®, from Endo); molindone hydrochloride (available under the tradename MOBAN®); loxapine (available under the tradename LOXITANE®; from Watson); loxapine hydrochloride (available under the tradename LOXITANE®); and loxapine succinate (available under the tradename LOXITANE®). Furthermore, benperidol (Glianimon®), perazine (Taxilan®) or melperone (Eunerpan®)) may be used.

Other suitable antipsychotic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), iloperidone, pimozide and flupenthixol.

The antipsychotic drugs listed above by Tradename may also be available from other suppliers under a different Tradename.

In one further aspect of the invention, suitable antipsychotic agents include olanzapine, risperidone, quetiapine, aripiprazole, haloperidol, clozapine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, amineptine, radafaxine, mianserin, mirtazapine, nefazodone and trazodone).

Anxiolytics which may be used in the therapy of the present invention include V1b antagonists, 5HT7 antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic M1 agonists (such as cevimeline).

In one embodiment, the active ingredient for use in combination with a compound of the present invention, is an atypical antipsychotic, for example clozapine, olanzapine, risperidone, quetiapine, aripirazole, ziprasidone or amisulpride.

In one embodiment, the active ingredient for use in combination with a compound of the present invention is a typical antipsychotic, for example chlorpromazine, thioridazine, mesoridazine, fluphenazine, perphenazine, prochlorperazine, trifluoperazine, thiothixine, haloperidol, thiflurpromazine, pimozide, droperidol, chlorprothixene, molindone or loxapine.

In another embodiment, the active ingredient for use in combination with a compound of the present invention is a mood stabiliser, for example lithium, sodium valproate/valproic acid/divalproex, carbamazepine, lamotrigine, gabapentin, topiramate, oxcarbazepine or tiagabine.

In another embodiment, the active ingredient for use in combination with a compound of the present invention is an antidepressant, for example a serotonin agonist (such as rauwolscine, yohimbine or metoclopramide); a serotonin reuptake inhibitor (such as citalopram, escitalopram, fluoxetine, fluvoxamine, femoxetine, indalpine, zimeldine, paroxetine or sertraline); a dual serotonin/noradrenaline reuptake inhibitor (such as venlafaxine, reboxetine, duloxetine or milnacipran); a noradrenaline reuptake inhibitors (such as reboxetine); a tricyclic antidepressants (such as amitriptyline, clomipramine, imipramine, maprotiline, nortriptyline or trimipramine); a monoamine oxidase inhibitor (such as isocarboxazide, moclobemide, phenelzine or tranylcypromine);

or other (such as bupropion, aminpetine, radafaxine, mianserin, mirtazapine, nefazodone or trazodone).

In another embodiment, the active ingredient for use in combination with a compound of the present invention is an anxiolytic, for example a benzodiazepine such as alprazolam or lorazepam.

For use in medicine, the compounds of the present invention are usually administered as a standard pharmaceutical composition. The present invention therefore provides in a further aspect a pharmaceutical composition comprising a compound of formula (I) as hereinbefore described or a salt or solvate thereof and a pharmaceutically acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) as hereinbefore described and their salts or solvates which are active when given orally can be formulated as liquids or solids, for example syrups, suspensions or emulsions, tablets, capsules and lozenges.

A liquid formulation will generally consist of a suspension or solution of the compound or salt or solvate in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt or solvate in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. The composition may be in unit dose form such as a tablet, capsule or ampoule.

Each dosage unit for oral administration contains, for example, from 1 to 250 mg (and for parenteral administration contains, for example, from 0.1 to 25 mg) of a compound of the formula (I) or a salt thereof calculated as the free base.

The compounds of the invention will normally be administered in a daily dosage regimen (for an adult patient) of, for example, an oral dose of between 1 mg and 500 mg, such as between 10 mg and 400 mg, e.g. between 10 and 250 mg or an intravenous, subcutaneous, or intramuscular dose of between 0.1 mg and 100 mg, such as between 0.1 mg and 50 mg, e.g. between 1 and 25 mg of the compound of the formula (I) or a salt thereof calculated as the free base, the compound being administered 1 to 4 times per day. Suitably the compounds will be administered for a period of continuous therapy, for example for a week or more.

The antipsychotic agent component or components used in the adjunctive therapy of the present invention may also be administered in their basic or acidic forms as appropriate or, where appropriate, in the form of a salt or other derivative. All solvates and all alternative physical forms of the antipsychotic agent or agents or their salts or derivatives as described herein, including but not limited to alternative crystalline forms, amorphous forms and polymorphs, are also within the scope of this invention. In the case of the antipsychotic agent or agents, the forms and derivatives are, for example, those which are approved for therapeutic administration as monotherapies, including those mentioned above, but all references to antipsychotic agents herein include all salts or other derivatives thereof, and all solvates and alternative physical forms thereof.

For adjunctive therapeutic administration according to the invention, compounds of formula (I) or salts or solvates and the antipsychotic agent or agents or their salts, derivatives or solvates may each be administered in pure form, but each of the components will, for example, be formulated into any suitable pharmaceutically acceptable and effective composition which provides effective levels of the respective component in the body. The choice of the most appropriate pharmaceutical compositions for each component is within the skill of the art, and may be the same form or different forms for each of the components. Suitable formulations include, but are not limited to tablets, capsules, powders, granules, lozenges, suppositories, reconstitutable powders, or liquid preparations such as oral or sterile parenteral solutions or suspensions.

For simultaneous administration as a combined composition of compounds of formula (I) and the antipsychotic agent or agents according to the invention, compounds of formula (I) or their salts or solvates and the antipsychotic agent or agents and their salts, derivatives or solvates may be administered together in pure form, but the combined components will, for example, be formulated into any suitable pharmaceutically acceptable and effective composition which provides effective levels of each of the components in the body. The choice of the most appropriate pharmaceutical compositions for the combined components is within the skill of the art. Suitable formulations include, but are not limited to tablets, sub-lingual tablets, buccal compositions, capsules, powders, granules, lozenges, suppositories, reconstitutable powders, or liquid preparations such as oral or sterile parenteral solutions or suspensions.

In order to obtain consistency of adjunctive administration, the compositions of each of the components, or of the combination of the components is, for example, in the form of a unit dose.

The term "treatment" includes prophylaxis, where this is appropriate for the relevant condition(s).

Biological Test Methods

FLIPR Experiments on $M_1$ Receptor to Determine Agonist/Antagonist Potency

Compounds of the invention were characterized in a functional assay to determine their ability to activate the intracellular calcium pathway in CHO cells with stable expression of human muscarinic receptors using FLIPR (Fluorometric Imaging Plate Reader) technology. Briefly, CHO-M1 cells were plated (20,000/well) and allowed to grow overnight at 37 degrees. Media was removed and 30 uL loading buffer containing FLIPR Calcium 3 dye (Molecular Devices Co., Sunnyvale, Calif.) was added according to manufacturer's instructions. After incubation at 37 degrees for 45-60 minutes, 10 uL of the assay buffer containing test compounds was added to each well on FLIPR instrument. Calcium response was monitored to determine agonism. Plates were then incubated for another 10-15 minutes before 10 uL of assay buffer containing acetylcholine was added as the agonist challenge. Calcium response was then monitored again to determine compound's antagonism to acetylcholine. Concentration-response curves of both agonism and antagonism on M1 receptors were performed for each compound. Results were imported into ActivityBase data analysis suite (ID Business Solution Inc., Parsippany, N.J.) where the curves were analysed by non-linear curve fitting and the resulting pEC50/pIC50 were calculated.

FLIPR Experiments on $M_1$ Receptor to Determine Agonist Intrinsic Activity

To determine the intrinsic activities of M1 agonist compounds, compounds of the invention were characterized in FLIPR experiments on U2OS cells with transient expression of human muscarinic M1 receptors. Briefly, U2OS cells were transduced with M1 BacMam virus (#) in $2\times10e^5$/mL cell suspension with 0.1% virus/cell ratio (v/v). The virus to cell ratio was determined in separate experiments by functional titration to be most appropriate to measure intrinsic activities of partial agonists. After mixing with virus in suspension, cells were then plated (10,000/well) and allowed to grow overnight at 37 degrees. FLIPR experiment was then carried out next day using the same protocol as described above for CHO-M1 cells. Results were imported into ActivityBase data analysis suite where the curves were analysed by non-linear curve fitting and the resulting pEC50 values were calculated. The intrinsic activities of agonist compounds were calculated as percentage of maximum FLIPR response induced by acetylcholine added as control on the same compound plates, and converted to a fraction between 0 and 1.

: Ames, R S; Fornwald, J A; Nuthulaganti, P; Trill, J J; Foley, J J; Buckley, P T; Kost, T A; Wu, Z and Romanos, M A. (2004) Use of BacMam recombinant baculoviruses to support G protein-coupled receptor drug discovery. Receptors and Channels 10 (3-4): 99-109

The exemplified compounds have a $pEC_{50}$ value of >6.0 at the muscarinic $M_1$ receptor, and intrinsic activity >0.5.

FLIPR Experiments on $M_{2-5}$ Receptor to Determine Receptor Subtype Selectivity To determine selectivity of compounds of the invention against other muscarinic receptor subtypes, compounds were characterized in FLIPR experiments in CHO cells with stable expression of human muscarinic receptors, M2, M3, M4 or M5. In the case of M2 and M4 receptors, chimeric G-protein Gqi5 was also co-expressed to couple receptors to the calcium signaling pathway. Briefly, cells were plated (20,000/well) and allowed to grow overnight at 37 degrees. FLIPR experiment was then carried out next day using the same protocol as described above for CHO-M1 cells. Results were imported into ActivityBase data analysis suite where the curves were analysed by non-linear curve fitting and the resulting pEC50/pIC50 values were calculated.

The exemplified compounds are selective for the M1 receptor over M2, M3, M4 and M5 receptors, with typical selectivity (ratio of pEC50's) of ≧10-fold, and in certain cases ≧100-fold.

The invention is further illustrated by the following non-limiting examples.

SCX refers to a sulfonic acid ion exchange resin supplied by Varian.

All reactions were either done under argon or can be done under argon, unless stated otherwise (for example hydrogenation reactions).

DESCRIPTION 1

Ethyl 4-[(5-fluoro-2-nitrophenyl)amino]-1-piperidinecarboxylate (D1)

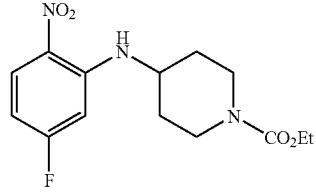

D1

Ethyl-4-amino-1-piperidine-carboxylate (11.9 g, 69 mmol) was added to a stirred suspension of 2,4-difluoronitrobenzene (10.0 g, 63 mmol), sodium carbonate (6.7 g, 63 mmol) and potassium iodide (0.1 g, 0.6 mmol) in dimethylformamide (100 mL). The mixture was heated to 50° C., stirred for 5 hours and then allowed to cool. The reaction mixture was diluted with water (130 mL) and ethyl acetate (200 mL). The organic phase was separated and the aqueous phase was extracted with ethyl acetate (2×200 mL). The organic extracts were combined, extracted with a 10% aqueous solution of citric acid (250 mL), dried over $MgSO_4$ and evaporated under reduced pressure. The residue was purified by column chromatography on silica, eluting with ethyl acetate/hexane (1:2) to give the title compound (16.9 g, 86% yield) as a yellow solid. ($R_f$: 0.5 (ethyl acetate/hexane 7:8))

DESCRIPTION 2

Ethyl 4-[(2-amino-5-fluorophenyl)amino]-1-piperidinecarboxylate (D2)

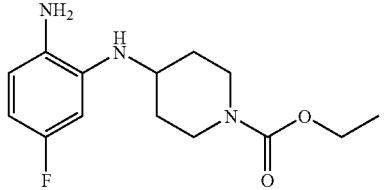

D2

A suspension of D1 (14.0 g, 45 mmol) and 5% Pd/C (3.0 g) in methanol (500 mL) in an autoclave (1000 mL) was put under an atmosphere of hydrogen (~20 atm). The mixture was stirred at room temperature for 3 hours and then filtered through a pad of celite. The filtrate was concentrated under reduced pressure to give the title compound (12.7 g, 100% yield) as a black solid that was used without further purification. ($R_f$: 0.3 (ethyl acetate/hexane 7:8))

DMSO-$d_6$) ☐ 10.98 (1H, br s), 8.93 (1H, br s), 7.40 (1H, d), 6.93 (1H, dd), 6.79 (1H, dd), 4.51-4.48 (1H, m), 3.35-3.32 (2H, m), 3.02-2.98 (2H, m), 2.55-2.52 (2H, m), 1.78-1.74 (2H, m); m.p.>190° C. (decomp).

DESCRIPTION 3

Ethyl 4-(6-fluoro-2-oxo-2,3-dihydro-1H-benzimidazol-1-yl)-1-piperidinecarboxylate (D3)

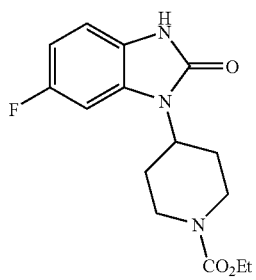

A solution of 1,1'-carbonyldiimidazole (12.6 g, 78 mmol) in acetonitrile (150 mL) was added portionwise over 10 minutes to a stirred solution of D2 (13.7 g, 49 mmol) in acetonitrile (250 mL) at 40° C. The reaction mixture was heated at 40° C. for 15 hours and then allowed to cool. The precipitate was collected by filtration and washed with acetonitrile (2×50 mL) to give the title compound (9.6 g, 69% yield) as a purple solid that was used without further purification. ($R_f$: 0.5 (ethyl acetate/hexane 7:8))

DESCRIPTION 4

6-Fluoro-1-(4-piperidinyl)-1,3-dihydro-2H-benzimidazol-2-one (D4)

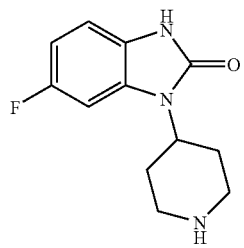

D3 (9.6 g, 30 mmol) was suspended in a 2.5M aqueous solution of sodium hydroxide (75 mL). The suspension was refluxed for 15 hours and then allowed to cool. The solution was acidified with 6M HCl (~40 mL) until no more effervescence was observed (~pH 2) and then the pH was carefully adjusted to pH 8.5 using 2.5 M aqueous NaOH. The resulting precipitate was collected by filtration, washed with cold water (20 mL) and then dried under vacuum at 40° C. for 15 hours to give the title compound (7.5 g, 100% yield) as a light purple solid ($R_f$: Baseline (ethyl acetate)). $^1$H-NMR (300 MHz,

DESCRIPTION 5

Ethyl 4-[(5-chloro-2-nitrophenyl)amino]-1-piperidinecarboxylate (D5)

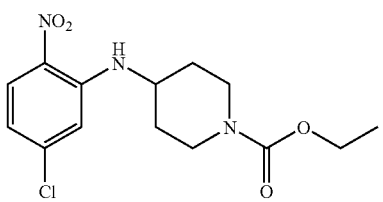

Ethyl-4-amino-1-piperidine-carboxylate (29.6 g, 0.17 mol) was added to a stirred suspension of 2,4-dichloronitrobenzene (30.0 g, 0.16 mol), sodium carbonate (16.5 g, 0.16 mol) and potassium iodide (0.26 g, 0.0016 mol) in dimethylformamide (300 mL). The mixture was heated to 140° C., stirred for 15 hours and then allowed to cool. The reaction mixture was diluted with water (400 mL) and ethyl acetate (600 mL). The aqueous phase was separated and the organic phase was extracted with water (2×300 mL). The organic phase was dried over $MgSO_4$ and evaporated under reduced pressure. The residue was purified by column chromatography on silica, eluting with ethyl acetate/hexane (1:3) to give the title compound (33.0 g, 65% yield) as an orange solid. ($R_f$: 0.4 (ethyl acetate/hexane 1:3))

DESCRIPTION 6

Ethyl 4-[(2-amino-5-chlorophenyl)amino]-1-piperidinecarboxylate (D6)

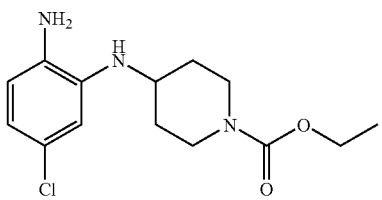

A suspension of D5 (15.0 g, 45 mmol) and 5% Pt/C (1.5 g) in methanol (500 mL) in an autoclave (1000 mL) was put under an atmosphere of hydrogen (~40 atm). The mixture was stirred at room temperature for 3 hours and then filtered through a pad of celite. The filtrate was concentrated under reduced pressure to give the title compound (13.5 g, 100% yield) as a dark brown solid that was used without further purification. ($R_f$: 0.3 (ethyl acetate/hexane 7:8))

DESCRIPTION 7

Ethyl 4-(6-chloro-2-oxo-2,3-dihydro-1H-benzimidazol-1-yl)-1-piperidinecarboxylate (D7)

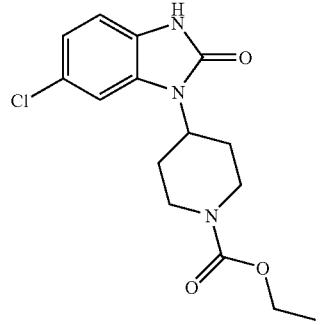

D7

1,1'-Carbonyldiimidazole (15.7 g, 97 mmol) was added portionwise over 10 minutes to a stirred solution of D6 (18.0 g, 60 mmol) in acetonitrile (300 mL). The reaction mixture was stirred at room temperature for 6 hours and the resulting precipitate was collected by filtration to give the title compound (12.0 g, 62% yield) as a violet solid that was used without further purification. ($R_f$: 0.2 (ethyl acetate))

DESCRIPTION 8

6-Chloro-1-(4-piperidinyl)-1,3-dihydro-2H-benzimidazol-2-one (D8)

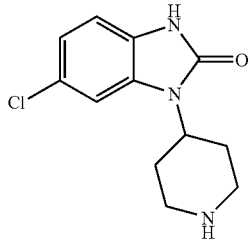

D8

D7 (12.0 g, 37 mmol) was suspended in a 2.5 M aqueous solution of sodium hydroxide (150 mL). The suspension was refluxed for 15 hours and then allowed to cool. The solution was acidified with 6 M HCl (~70 mL) until no more effervescence was observed (~pH 2) and then the pH was carefully adjusted to pH 8.5 using 2.5M aqueous NaOH whilst the solution was cooled to 0° C. The resulting precipitate was collected by filtration, washed with cold water (20 mL) and then dried under vacuum at 40° C. for 15 hours to give the title compound (7.1 g, 76% yield) as a light brown solid ($R_f$: Baseline (ethyl acetate)). $^1$H-NMR (300 MHz, DMSO-$d_6$) □ 11.11 (1H, br s), 8.97 (1H, br s), 7.52 (1H, s), 6.99-6.97 (2H, m), 4.51-4.48 (1H, m), 3.33-3.31 (2H, m), 3.02-2.97 (2H, m), 2.48-2.46 (2H, m), 1.81-1.77 (2H, m); m.p.>300° C.

DESCRIPTION 8 ALTERNATIVE PROCEDURE 6-chloro-1-(4-piperidinyl)-1,3-dihydro-2H-benzimidazol-2-one hydrochloride (D8)

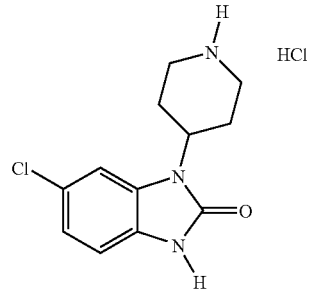

D8

1,1-Dimethylethyl 4-(6-chloro-2-oxo-2,3-dihydro-1H-benzimidazol-1-yl)-1-piperidine-carboxylate D29 (5.7 g) was dissolved in ethanol (20 mL) and HCl (4M in 1,4-dioxane, 20 mL) was added at room temperature. The mixture was stirred at room temperature for 1 h. then filtered washing with ether to give the title compound, 4.0 g.

DESCRIPTION 9

1-(Tetrahydro-2H-pyran-4-yl)-4-piperidinamine (D9)

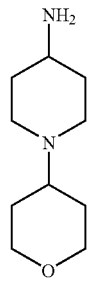

D9 a) 10 g (0.050 mol, 1 eq) of 4-boc-amino-piperidine, 6 g (0.060 mol, 1.2 eq) of tetrahydro-4H-pyran-4-one, 16 g (0.075 mol, 1.5 eq) of sodium triacetoxyborohydride, and 3 g (0.050 mol, 1 eq) of acetic acid were combined in 600 mL of dichloroethane and stirred at ambient temperature. After two days, the reaction was washed with 2×200 mL saturated sodium bicarbonate. The organic layer was separated, dried with sodium sulfate, and evaporated to yield 9.2 g (65% yield) of 1,1-dimethylethyl [1-(tetrahydro-2H-pyran-4-yl)-4-piperidinyl]carbamate as a white solid. $^1$H-NMR (400 MHz, DMSO-$d_6$): δ 6.73 (d, J=7.6 Hz, 1H), 3.86 (m, 2H), 3.24 (app t, 2H), 3.16 (m, 1H), 2.81 (m, 4H), 2.37 (m, 1H), 2.07 (app t, 2H), 1.73-1.59 (m, 4H), 1.44-1.24 (m, 4H), 1.37 (s, 9H).

b) 9.2 g (0.0323 mol, 1 eq) of 1,1-dimethylethyl [1-(tetrahydro-2H-pyran-4-yl)-4-piperidinyl]carbamate, 65 mL (0.258 mol, 8 eq) of 4 M HCl in dioxane, and enough methanol to achieve dissolution were combined and stirred at ambient temperature overnight. The reaction mixture was then evaporated. Dichloromethane and 1 M NaOH were added. Sodium chloride was then added to saturate the aqueous layer. The aqueous layer was extracted with dichloromethane twice. The organic layers were combined, dried with sodium sulfate, and evaporated to yield 5.5 g (92% yield) of 1-(tetrahydro-2H-pyran-4-yl)-4-piperidinamine as a low melting white solid. $^1$H-NMR (400 MHz, DMSO-$d_6$): δ 3.86 (m, 2H), 3.24 (m, 2H), 2.77 (m, 2H), 2.46 (m, 1H), 2.35 (m, 1H), 2.25-1.05 (v br s, 2H, NH$_2$), 2.07 (m, 2H), 1.64 (m, 4H), 1.39 (m, 2H), 1.16 (m, 2H); MS (ESI): 185 [M+H]+.

DESCRIPTION 10

N-(5-bromo-2-nitrophenyl)-1-(tetrahydro-2H-pyran-4-yl)-4-piperidinamine (D10)

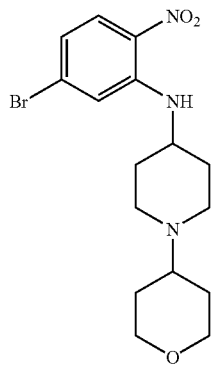

400 mg (0.0018 mol, 1 eq) of 4-bromo-2-fluoro-1-nitrobenzene, 330 mg (0.0018 mol, 1 eq) of D9, 350 mg (0.0027 mol, 1.5 eq) of diisopropylethylamine, and 5 mL of dimethylformamide were combined, heated to 200° C. and held for 1 min in a microwave reactor. 80 mL of water was then added and the reaction extracted with 2×75 mL of dichloromethane. The dichloromethane layers were combined, dried with sodium sulfate, and evaporated to yield N-(5-bromo-2-nitrophenyl)-1-(tetrahydro-2H-pyran-4-yl)-4-piperidinamine which was used without further purification in the next step. MS (ESI): 385 [M+H]+.

DESCRIPTION 11

(2-Amino-5-bromophenyl)[1-(tetrahydro-2H-pyran-4-yl)-4-piperidinyl]amine (D11)

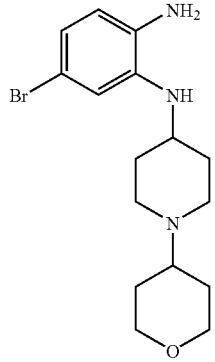

688 mg (0.0018 mol, 1 eq) of N-(5-bromo-2-nitrophenyl)-1-(tetrahydro-2H-pyran-4-yl)-4-piperidinamine D10, 350 mg (0.00018 mol, 0.1 eq) of 10% platinum on carbon, 375 mg (0.0057 mol, 3.2 eq) of ammonium formate, and 20 mL of methanol (degassed with nitrogen) were combined and stirred for 1 hour. The catalyst was then filtered off, and the filtrate was evaporated. Water and dichloromethane were added and shaken. Separation and drying of the dichloromethane layer with sodium sulfate followed by evaporation yielded a crude product which was purified exactly as in Example 1 where A=H$_2$O and B=CH$_3$CN to yield (2-amino-5-bromophenyl)[1-(tetrahydro-2H-pyran-4-yl)-4-piperidinyl]amine, the title compound. MS (ESI): 355 [M+H]+.

DESCRIPTION 12

Ethyl 4-[(5-methyl-2-nitrophenyl)amino]-1-piperidinecarboxylate (D12)

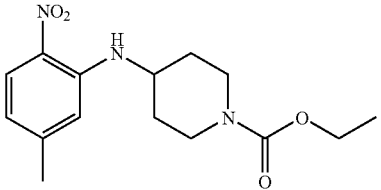

Ethyl-4-amino-1-piperidine-carboxylate (18.3 g, 106 mmol) was added to a stirred suspension of 3-fluoro-4-nitrotoluene (15.0 g, 97 mmol), sodium carbonate (10.3 g, 97 mmol) and potassium iodide (0.16 g, 0.97 mmol) in dimethylformamide (150 mL). The mixture was heated to 50° C., stirred for 15 hours and then allowed to cool. The reaction mixture was diluted with water (200 mL) and ethyl acetate (200 mL). The organic phase was separated and the aqueous phase was extracted with ethyl acetate (2×200 mL). The organic extracts were combined, extracted with a 10% aqueous solution of citric acid (250 mL), dried over MgSO$_4$ and evaporated under reduced pressure. The residue was purified by column chromatography on silica, eluting with dichloromethane and then ethyl acetate/hexane (7:8) to give the title compound (25.0 g, 84% yield) as a yellow solid. ($R_f$: 0.3 (ethyl acetate/hexane 7:8))

DESCRIPTION 13

Ethyl 4-[(2-amino-5-methylphenyl)amino]-1-piperidinecarboxylate (D13)

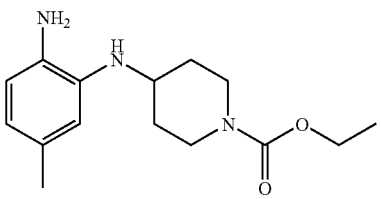

A suspension of D12 (20.0 g, 65 mmol) and 5% Pd/C (3.0 g) in methanol (400 mL) in an autoclave (1000 mL) was put under an atmosphere of hydrogen (~50 atm). The mixture was stirred at room temperature for 3 hours and then filtered through a pad of celite. The filtrate was concentrated under reduced pressure to give the title compound (18.0 g, 100% yield) as a purple oil that was used without further purification. ($R_f$: 0.1 (ethyl acetate/hexane 7:8))

DESCRIPTION 14a

Ethyl 4-(6-methyl-2-oxo-2,3-dihydro-1H-benzimidazol-1-yl)-1-piperidinecarboxylate (D14a)

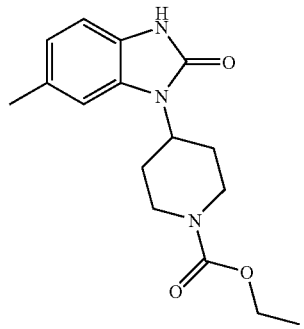

A solution of 1,1'-carbonyldiimidazole (12.2 g, 75 mmol) in acetonitrile (150 mL) was added portionwise over 10 minutes to a stirred solution of D13 (13.0 g, 47 mmol) in acetonitrile (150 mL) at 40° C. The reaction mixture was heated at 40° C. for 36 hours and then allowed to cool. The precipitate was collected by filtration and washed with acetonitrile (2×50 mL) to give the title compound (10.8 g, 76% yield) as a light purple solid that was used without further purification ($R_f$: 0.5 (ethyl acetate/hexane 7:8)). m.p. 222-224° C.

DESCRIPTION 14b

6-Methyl-1-(4-piperidinyl)-1,3-dihydro-2H-benzimidazol-2-one (D14b)

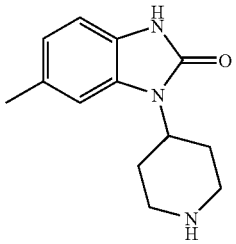

D14a (12.5 g, 41 mmol) was suspended in a 2.5 M aqueous solution of sodium hydroxide (150 mL). The suspension was refluxed for 15 hours and then allowed to cool. The solution was acidified with 6 M HCl (~70 mL) until no more effervescence was observed (~pH 2) and then the pH was carefully adjusted to pH 8.5 using 2.5 M aqueous NaOH. The resulting precipitate was collected by filtration, washed with cold water (20 mL) and then dried under vacuum at 40° C. for 15 hours to give the title compound (9.5 g, 100% yield) as a beige solid ($R_f$: Baseline (ethyl acetate/hexane 2:3)). $^1$H-NMR (300 MHz, DMSO-$d_6$): δ 10.77 (1H, br s), 9.00 (1H, br s), 7.29 (1H, s), 6.84 (1H, d), 6.78 (1H, d), 4.51-4.47 (1H, m), 3.33-3.30 (2H, m), 3.03-2.99 (2H, m), 2.61-2.58 (2H, m), 2.46 (3H, s), 1.76-1.72 (2H, m); m.p.>300° C.

DESCRIPTION 15

2-Fluoro-4-(methoxy)-1-nitrobenzene (D15)

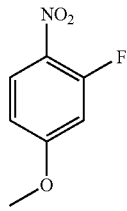

Potassium carbonate (79.0 g, 0.57 mol) was added to a stirred solution of 3-fluoro-4-nitrophenol (45.0 g, 0.29 mol) and methyl iodide (50.0 mL, 0.81 mol) in methylethyl ketone (450 mL) at room temperature. The suspension was stirred at 40° C. for 15 hours and then allowed to cool. The mixture was diluted with water (200 mL) and the organic phase was separated. The aqueous phase was extracted with dichloromethane (2×200 mL). The organic extracts were combined, dried over MgSO$_4$ and evaporated under reduced pressure to give the title compound (48.0 g, 97% yield) as a light yellow solid.

DESCRIPTION 16

Ethyl 4-{[5-(methyloxy)-2-nitrophenyl]amino}-1-piperidinecarboxylate (D16)

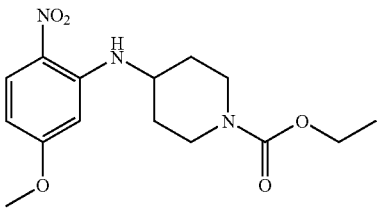

Ethyl-4-amino-1-piperidine-carboxylate (53.0 g, 0.31 mol) was added to a stirred suspension of D15 (48.0 g, 0.28 mol), sodium carbonate (29.7 g, 0.28 mol) and potassium iodide (0.46 g, 0.003 mol) in dimethylformamide (200 mL). The mixture was heated to 50° C., stirred for 15 hours and then allowed to cool. The reaction mixture was poured in water (500 mL), stirred for 10 minutes and the precipitate collected by filtration to give the title compound (71.0 g, 79%) as a yellow solid that was used without further purification ($R_f$: 0.5 (ethyl acetate/hexane 7:8)). m.p. 115-117° C.

DESCRIPTION 17

Ethyl 4-{[2-amino-5-(methyloxy)phenyl]amino}-1-piperidinecarboxylate (D17)

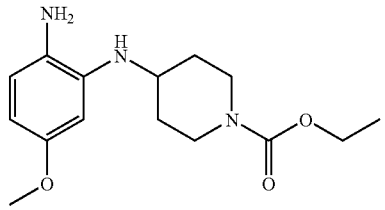

A suspension of D16 (25.0 g, 77 mmol) and 5% Pd/C (2.6 g) in methanol (500 mL) in an autoclave (1000 mL) was put under an atmosphere of hydrogen (~20 atm). The mixture was stirred at room temperature for 2.5 hours and then filtered through a pad of celite. The filtrate was concentrated under reduced pressure to give the title compound (21.4 g, 95% yield) as a purple solid that was used without further purification ($R_f$: 0.2 (ethyl acetate/hexane 7:8)). m.p. 97-99° C.

DESCRIPTION 18

Ethyl 4-[6-(methyloxy)-2-oxo-2,3-dihydro-1H-benzimidazol-1-yl]-1-piperidinecarboxylate (D18)

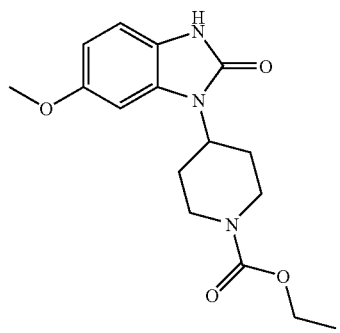

1,1'-Carbonyldiimidazole (17.8 g, 110 mmol) was added portionwise over 10 minutes to a stirred solution of D17 (21.4 g, 73 mmol) in acetonitrile (250 mL) at 50° C. The reaction mixture was heated at 50° C. for 15 hours and then allowed to cool. The solvent was removed under reduced pressure and the residue was diluted with dichloromethane (200 mL) and a 10% aqueous solution of citric acid (100 mL). The aqueous phase was separated and the organic phase was extracted with a 10% aqueous solution of citric acid (100 mL), dried over MgSO₄ and evaporated under reduced pressure to give the title compound (21.8 g, 95% yield) as a brown solid that was used without further purification. ($R_f$: 0.1 (ethyl acetate/hexane 7:8))

DESCRIPTION 19

6-(Methyloxy)-1-(4-piperidinyl)-1,3-dihydro-2H-benzimidazol-2-one (D19)

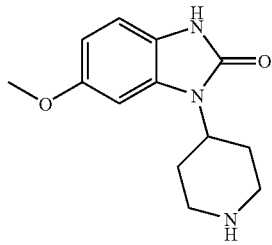

D18 (21.8 g, 68 mmol) was suspended in a 2.5 M aqueous solution of sodium hydroxide (200 mL). The suspension was refluxed for 15 hours and then allowed to cool. The solution was acidified with 6 M HCl (~70 mL) until no more effervescence was observed (~pH 2) and then the pH was carefully adjusted to pH 8.5 using 2.5 M aqueous NaOH whilst the solution was cooled to 0° C. The resulting precipitate was collected by filtration, washed with cold water (20 mL) and then dried under vacuum at 40° C. for 15 hours to give the title compound (12.5 g, 74% yield) as a brown solid ($R_f$: Baseline (ethyl acetate).

$^1$H-NMR (300 MHz, DMSO-$d_6$): δ 10.71 (1H, brs), 9.17 (1H, brs), 7.09 (1H, s), 6.85 (1H, d), 6.55 (1H, d), 4.50-4.48 (1H, m), 3.69 (3H, s), 3.33-3.31 (2H, m), 3.03-3.00 (2H, m), 2.61-2.58 (2H, m), 1.75-1.71 (2H, m); m.p.>190° C. (decomp).

DESCRIPTION 20

Ethyl 4-{[2-nitro-5-(trifluoromethyl)phenyl]amino}-1-piperidinecarboxylate (D20)

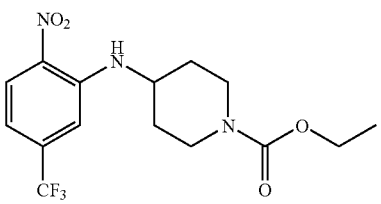

Ethyl-4-amino-1-piperidine-carboxylate (16.0 g, 92 mmol) was added to a stirred suspension of 3-chloro-4-nitrobenzotrifluoride (19.0 g, 84 mmol), sodium carbonate (8.9 g, 84 mmol) and potassium iodide (0.14 g, 0.84 mmol) in dimethylformamide (200 mL). The mixture was heated to 90° C., stirred for 15 hours and then allowed to cool. The reaction mixture was diluted with water (200 mL) and ethyl acetate (200 mL). The aqueous phase was separated and the organic phase was extracted with water (2×200 mL). The organic phase was dried over MgSO₄ and evaporated under reduced pressure. The residue was purified by column chromatography on silica, eluting with ethyl acetate/hexane (1:5) to give the title compound (12.0 g, 40% yield) as an orange solid. ($R_f$: 0.4 (ethyl acetate/hexane 1:5))

DESCRIPTION 21

Ethyl 4-{[2-amino-5-(trifluoromethyl)phenyl]amino}-1-piperidinecarboxylate (D21)

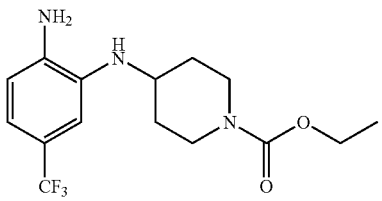

(D21)

A suspension of D20 (18.0 g, 50 mmol) and 5% Pd/C (1.7 g) in methanol (400 mL) in an autoclave (1000 mL) was put under an atmosphere of hydrogen (~30 atm). The mixture was stirred at room temperature for 3 hours and then filtered through a pad of celite. The filtrate was concentrated under reduced pressure to give the title compound (15.9 g, 96% yield) as a brown solid that was used without further purification. ($R_f$: 0.3 (ethyl acetate/hexane 7:8))

DESCRIPTION 22

Ethyl 4-[2-oxo-6-(trifluoromethyl)-2,3-dihydro-1H-benzimidazol-1-yl]-1-piperidinecarboxylate (D22)

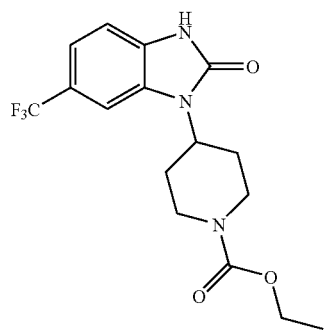

D22

1,1'-Carbonyldiimidazole (9.9 g, 61 mmol) was added portionwise over 10 minutes to a stirred solution of D21 (12.7 g, 38 mmol) in acetonitrile (200 mL). The reaction mixture stirred at room temperature for 5 hours and then the solvent was removed under reduced pressure. The residue was diluted with dichloromethane (200 mL) and extracted with a 10% aqueous solution of citric acid (2×100 mL). The organic phase was dried over MgSO$_4$ and evaporated under reduced pressure to give the title compound (13.5 g, 99% yield) as a brown solid that was used without further purification. ($R_f$: 0.2 (ethyl acetate))

DESCRIPTION 23

1-(4-piperidinyl)-6-(trifluoromethyl)-1,3-dihydro-2H-benzimidazol-2-one (D23)

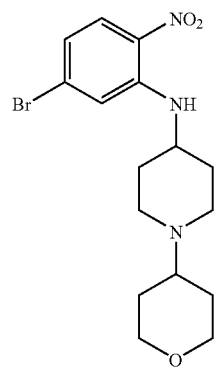

D23

Iodotrimethylsilane (17 mL, 120 mmol) was added to a stirred solution of D22 (13.5 g, 38 mmol) in chloroform (150 mL) under argon. The reaction mixture was refluxed for 15 hours and then allowed to cool. Methanol (30 mL) was added and the reaction mixture was stirred for 30 minutes. The precipitate was collected by filtration and washed with chloroform (2×20 mL). The solid was dissolved in water (150 mL) and the solution basified to pH 13 with solid sodium hydroxide. After stirring for 30 minutes, 6 M HCl was added until pH 8.5 was reached and the resulting precipitate was collected by filtration. The solid was dried under vacuum at 40° C. for 15 hours to give the title compound (11.1 g, 97% yield) as a colourless solid ($R_f$: Baseline (ethyl acetate/methanol (19:1)). $^1$H-NMR (300 MHz, DMSO-d$_6$): δ 7.60 (1H, s), 7.34 (1H, d), 7.14 (1H, d), 4.55 (1H, m), 3.40 (2H, d), 3.05 (2H, t), 2.50 (2H, m), 1.88 (2H, m); m.p.>200° C. (decomp.).

DESCRIPTION 24

N-(5-bromo-2-nitrophenyl)-1-(tetrahydro-2H-pyran-4-yl)-4-piperidinamine (D24)

D24

To a mixture of 4-bromo-2-fluoro-1-nitrobenzene (1.05 g, 0.0048 mol) and 1-(tetrahydro-2H-pyran-4-yl)-4-piperidinamine (0.883 g, 0.0048 mol) D9 in dimethylformamide (10 mL) was added diisopropylethylamine (1.175 mL, 0.0068 mol). The resulting mixture was sealed in a 20 mL Biotage Process Vial and irradiated at 200° C. for 1 min in the Smith Synthesizer. After irradiation, dichloromethane (15 mL) was added to the reaction solution. The resulted solution was washed with H$_2$O (2×10 mL). The combined aqueous layers were extracted with dichloromethane (2×10 mL). The organic layers were combined, dried with Na$_2$SO$_4$, and concentrated in vacuo to yield the title compound (1.8 g) which was used in next step directly without purification. MS (ESI): 384 [M+]; $^1$H NMR (400 MHz, CDCl$_3$): δ 1.68 (6H, m), 2.09 (2H, d), 2.49 (3H, m), 2.89 (2H, d), 3.39 (2H, t), 3.51 (1H, m), 4.04 (2H, dd), 6.72 (1H, dd), 7.01 (1H, d), 8.03 (1H, d), 8.14 (1H, d).

DESCRIPTION 25

N-(5-ethenyl-2-nitrophenyl)-1-(tetrahydro-2H-pyran-4-yl)-4-piperidinamine (D25)

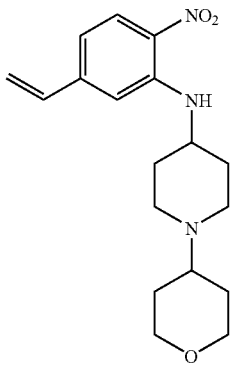

To a mixture of N-(5-bromo-2-nitrophenyl)-1-(tetrahydro-2H-pyran-4-yl)-4-piperidinamine D24 (1.8 g, 0.0047 mol) and vinyl tri(n-butyl)tin (1.58 mL, 0.0054 mol) in toluene (70 mL) was added, under a positive flow of N$_2$, triphenyl phosphine (0.295 g, 1.125 mmol) and bis(dibenzylidene acetone) palladium (0) (0.338 g, 0.675 mmol). The mixture was put under a N$_2$ atmosphere and heated at 130° C. for 1.5 hours (LC/MS was used to monitor the reaction). After the reaction was completed the reaction mixture was cooled to room temperature, filtered through a celite pad, and washed with dichloromethane. The filtrate was washed with 10% of aqueous NH$_4$OH solution (3×50 mL), H$_2$O (3×50 mL), and dried with Na$_2$SO$_4$, and concentrated in vacuo. The resulting residue was redissolved in acetonitrile. 416 mg of the title compound was crystallized out and the resulted solution was purified by using a Gilson preparative HPLC system with a Waters Xterra (C-18) column 100 mm by 50 mm ID, eluting with 10% B to 90% B in 10 min, where A=H$_2$O and B=CH$_3$CN pumped at 150 mL/min to yield additional 578 mg of the title compound (overall 994 mg, 67% yield). MS (ESI): 332 [M+H]+; $^1$H NMR (400 MHz, CDCl$_3$): δ 1.67 (6H, m), 2.11 (2H, d), 2.47 (3H, m), 2.90 (2H, d), 3.39 (2H, t), 3.61 (1H, m), 4.03 (2H, dd), 5.47 (1H, d), 5.88 (1H, d), 6.66 (1H, dd), 6.75 (2H, m), 8.14 (1H, d), 8.23 (1H, d).

DESCRIPTION 26

(2-amino-5-ethylphenyl)[1-(tetrahydro-2H-pyran-4-yl)-4-piperidinyl]amine (D26)

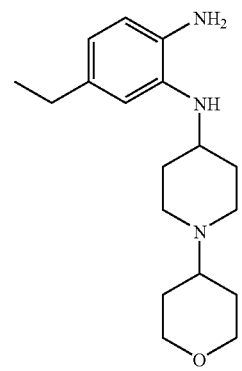

To a mixture of N-(5-ethenyl-2-nitrophenyl)-1-(tetrahydro-2H-pyran-4-yl)-4-piperidinamine D25 (416 mg, 1.26 mmol) and NH$_4$HCO$_2$ (792 mg, 12.6 mmol) in methanol (100 mL) was added, under a positive flow of N$_2$, 10% Pd—C (200 mg, 0.189 mmol). The resulted mixture was stirred under room temperature for 1.5 hours and was then filtered through a celite pad. The filtrate was concentrated in vacuo. The residue was dissolved in dichloromethane (100 mL). The resulting solution was washed with saturated NaCl solution (2×100 mL), dried with Na$_2$SO$_4$, and concentrated in vacuo to yield the title compound (251 mg, 66% yield). MS (ESI): 304 [M+H]+.

DESCRIPTION 27

1,1-Dimethylethyl 4-[(5-chloro-2-nitrophenyl)amino]-piperidinecarboxylate (D27)

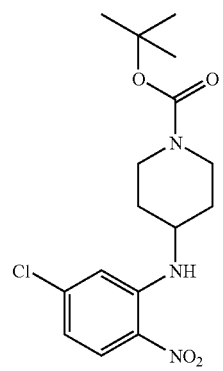

4-Chloro-2-fluoronitrobenzene (3.5 g) was dissolved in dry dimethylformamide (25 mL) and diisopropylethylamine (3.6 mL), and 1,1-dimethylethyl 4-amino-1-piperidinecarboxylate (4.2 g) were added at room temperature. The mixture was stirred at 80° C. for 1 h, then cooled to room temperature and water and ethyl acetate added. The organic layer was dried over MgSO$_4$, filtered and evaporated, and the residue was purified by chromatography eluting with 10 to 25% ethyl acetate in hexane to afford the title compound, 6.8 g.

DESCRIPTION 28

1,1-Dimethylethyl 4-[(2-amino-5-chlorophenyl)amino]-1-piperidinecarboxylate (D28)

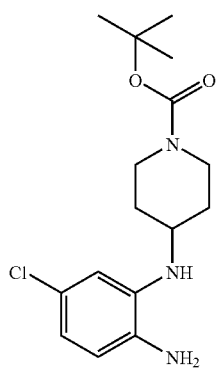

D28

1,1-Dimethylethyl 4-[(5-chloro-2-nitrophenyl)amino]-piperidinecarboxylate D27 (6.3 g) was dissolved in ethanol (100 mL) and Raney nickel (50% aqueous suspension, 5 mL) was added at room temperature; the mixture was heated to 40° C. and hydrazine monohydrate (3.0 mL) was added over 30 min. After 30 min more, the reaction mixture was cooled to room temperature, filtered through Celite and the solvent was evaporated to yield the title compound, 5.8 g.

DESCRIPTION 29

1,1-Dimethylethyl 4-(6-chloro-2-oxo-2,3-dihydro-1H-benzimidazol-1-yl)-1-piperidinecarboxylate (D29)

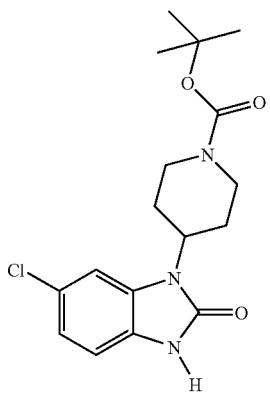

D29

1,1-Dimethylethyl 4-[(2-amino-5-chlorophenyl)amino]-1-piperidinecarboxylate (D28) (5.8 g) was dissolved in 100 ml of dichloromethane at 0° C. and phosgene (20% in toluene, 10 ml) and triethylamine (5.6 ml) were added and the mixture was stirred at 0° C. for 1 h, then washed with aqueous citric acid, dried over MgSO$_4$, filtered and evaporated The product was crystallised from diethyl ether to yield the title compound, 5.7 g.

DESCRIPTION 30

1,1-Dimethylethyl 4-{[({2-bromo-4-[(trifluoromethyl)oxy]phenyl}amino)carbonyl]amino}-1-piperidinecarboxylate (D30)

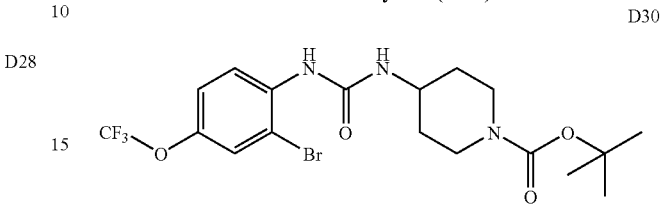

D30

A solution of 2-bromo-4-(trifluoromethyloxy)aniline (5.1 g), in 1,4-dioxane (30 mL) was treated with bis(trichloromethyl) carbonate (2.2 g). The mixture was heated to 100° C. to give a clear solution then allowed to cool to ambient temperature. The solvent was evaporated and the residue was dissolved in dichloromethane (70 mL) and 1,1-dimethylethyl 4-amino-1-piperidinecarboxylate (4.0 g) was added. The mixture was stirred overnight at room temperature. Silica gel was added and the solvent was evaporated. The residue was loaded onto a silica gel chromatography column which was eluted with hexane/ethyl acetate 0-100% followed by chromatography on silica gel eluted with dichloromethane/methanol 0-10% to give the title compound as a white solid from diethyl ether (4.3 g).

$^1$HNMR d(DMSO, 400 MHz) 1.25 (2H, m), 1.40 (9H, s), 1.79 (2H, m), 2.93 (2H, broad), 3.64 (1H, m), 3.80 (2H, m), 7.21 (1H, d), 7.35 (1H, d), 7.66 (1H, s), 7.91 (1H, s), 8.19 (1H, d).

DESCRIPTION 31

1,1-Dimethylethyl 4-{2-oxo-6-[(trifluoromethyl)oxy]-2,3-dihydro-1H-benzimidazol-1-yl}-1-piperidinecarboxylate (D31)

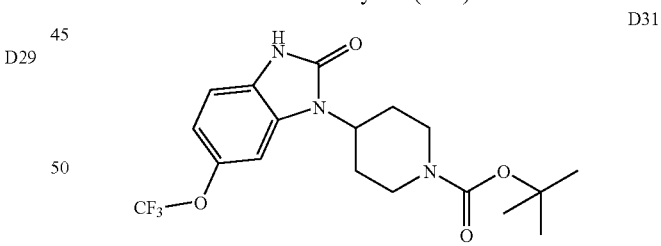

D31

A solution of tris(dibenzylideneacetone)dipalladium (0) (0.33 g), 1,1'-bis(diphenylphosphino)ferrocene (0.21 g), sodium tert-butoxide (1.1 g) in 1,4-dioxane (20 mL) was stirred under an atmosphere of argon for 10 minutes. 1,1-Dimethylethyl 4-{[({2-bromo-4-[(trifluoromethyl)oxy]phenyl}amino)carbonyl]amino}-1-piperidinecarboxylate (D30) (2.7 g) was added and the mixture was heated to 90° C. The mixture was stirred at this temperature overnight. The mixture was poured into dichloromethane which was washed with dilute ammonium chloride, brine and dried over sodium sulphate. The solvent was removed and the residue was chromatographed on silica gel eluted with ethyl acetate/hexane 0-50% to give the title compound as a solid foam. (1.54 g)

$^1$HNMR (DMSO, 400 MHz) 1.41 (9H, m), 1.72 (2H, s), 2.24 (2H, m), 2.85 (2H, broad), 4.18 (2H, m), 4.31 (1H, m), 6.88 (1H, d), 7.00 (1H, d), 7.10 (1H, s).

DESCRIPTION 32

1-(4-Piperidinyl)-6-[(trifluoromethyl)oxy]-1,3-dihydro-2H-benzimidazol-2-one hydrochloride (D32)

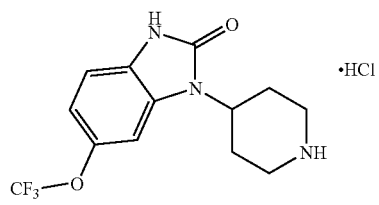

A solution of 1,1-dimethylethyl 4-{2-oxo-6-[(trifluoromethyl)oxy]-2,3-dihydro-1H-benzimidazol-1-yl}-1-piperidinecarboxylate (D31) (1.54 g) in methanol (20 mL) was treated with a saturated solution of hydrogen chloride in ethanol (10 mL). The mixture was stirred for 1 hour when the solvent was removed to give the title compound as a white solid (1.28 g).

$^1$HNMR (DMSO, 400 MHz) 1.81 (2H, m), 2.56 (2H, m), 3.04 (2H, m), 3.40 (2H, m), 4.56 (1H, m), 6.99 (1H, m), 7.05 (1H, d), 7.50 (1H, d), 8.97 (2H, br s), 11.2 (1H, s).

DESCRIPTION 33

1,1-Dimethylethyl 4-[({[2-bromo-4-(1-methylethyl)phenyl]amino}carbonyl)amino]-1-piperidinecarboxylate (D33)

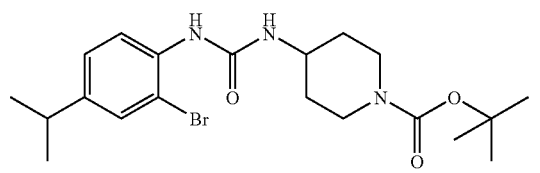

A solution of 2-bromo-4-(isopropyl)aniline (3.4 g), in 1,4-dioxane (30 mL) was treated with bis(trichloromethyl) carbonate (1.8 g). The mixture was heated to 100° C. to give a clear solution then allowed to cool to ambient temperature. The solvent was evaporated and the residue was dissolved in dichloromethane (50 mL) and 1,1-dimethylethyl 4-amino-1-piperidinecarboxylate (2.42 g) was added. The mixture was stirred overnight at room temperature. Silica gel was added and the solvent was evaporated. The residue was loaded onto a silica gel chromatography column which was eluted with dichloromethane/methanol 0-10% to give the title compound as a white solid (1.2 g).

$^1$HNMR (DMSO, 400 MHz) 1.15 (6H, m), 1.25 (2H, m), 1.40 (9H, s), 1.80 (2H, m), 2.80 (1H, m), 2.93 (2H, broad), 3.63 (1H, m), 3.77 (2H, m), 7.03 (1H, d), 7.13 (1H, d), 7.44 (1H, s), 7.68 (1H, s), 7.92 (1H, d).

DESCRIPTION 34

1,1-Dimethylethyl 4-[6-(1-methylethyl)-2-oxo-2,3-dihydro-1H-benzimidazol-1-yl]-1-piperidinecarboxylate (D34)

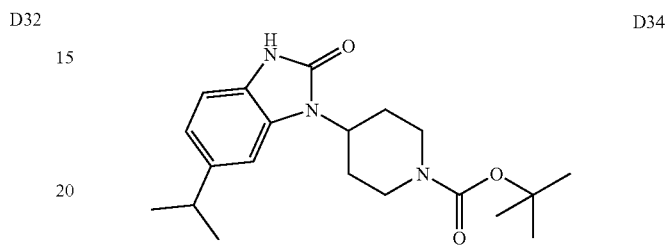

A solution of tris(dibenzylideneacetone)dipalladium (0) (0.14 g), 1,1'-bis(diphenylphosphino)ferrocene (0.07 g), sodium tert-butoxide (0.4 g) in 1,4-dioxane (10 mL) was stirred under an atmosphere of argon for 10 minutes. 1,1-dimethylethyl 4-[({[2-bromo-4-(1-methylethyl)phenyl]amino}carbonyl)amino]-1-piperidinecarboxylate D33 (2.7 g) was added and the mixture was heated to 90° C. The mixture was stirred at this temperature overnight. The mixture was poured into ethyl acetate which was washed with dilute sodium bicarbonate, brine and dried over sodium sulphate. The solvent was removed and the residue was chromatographed on silica gel eluted with ethyl acetate/hexane 0-50% to give the title compound as a solid. (0.723 g)

$^1$HNMR (DMSO, 400 MHz) 1.19 (6H, m), 1.44 (9H, s), 1.65 (2H, m), 2.22 (2H, m), 2.85 (2H, m), 4.02 (2H, m), 4.33 (1H, m), 6.85 (2H, m), 7.02 (1H, s), 10.2 (1H, s).

DESCRIPTION 35

6-(1-Methylethyl)-1-(4-piperidinyl)-1,3-dihydro-2H-benzimidazol-2-one hydrochloride (D35)

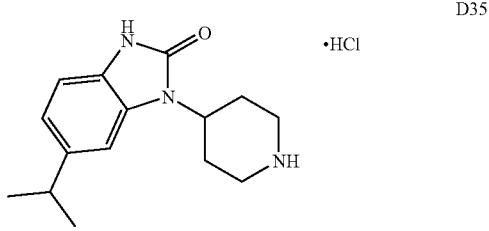

A solution of 1,1-dimethylethyl 4-[6-(1-methylethyl)-2-oxo-2,3-dihydro-1H-benzimidazol-1-yl]-1-piperidinecarboxylate D34 (0.71 g) in methanol (30 mL) was treated with a saturated solution of hydrogen chloride in ethanol (10 mL). The mixture was stirred for 1 hour when the solvent was removed to give the title compound as a white solid (0.59 g).

¹HNMR (DMSO, 400 MHz) 1.22 (6H, m), 1.81 (2H, m), 2.65 (2H, m), 2.87 (1H, m), 2.92 (2H, m), 3.13 (2H, m), 3.87 (2H, m), 4.51 (1H, m), 6.88 (2H, m), 7.29 (1H, s), 8.57 (1H, br), 9.04 (H, br), 10.8 (1H, s).

DESCRIPTION 36

4-{4-[2-Oxo-6-(trifluoromethoxy)-2,3-dihydro-1H-benzimidazol-1-yl]piperidin-1-yl}tetrahydro-2H-pyran-4-carbonitrile (D36)

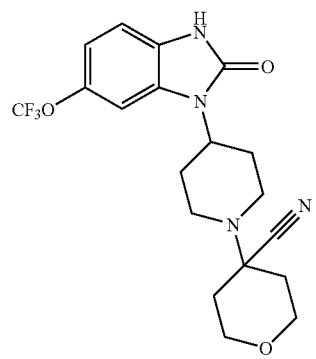

A mixture of 1-piperidin-4-yl-6-(trifluoromethoxy)-1,3-dihydro-2H-benzimidazol-2-one (D32, 301 mg), 2-hydroxy-2-methylpropanenitrile, (160 mg), tetrahydro-4H-pyran-4-one (200 mg) magnesium sulphate (600 mg) and N,N-dimethylacetamide (1 ml) were stirred at 60° C. under a slow stream of argon overnight. The resulting white paste was partitioned between dichloromethane and water and sonicated. The dichloromethane layer was separated, dried by passing through a 3 g hydromatrix cartridge. (Large proportion of the material was lost due to spillage). The solvent was removed and the title compound was obtained as a white solid from ether. Yield 62 mg. M⁺ 411.

¹H NMR δ (d⁶DMSO): 1.65 (2H, m), 1.78 (2H, m), 2.20 (4H, m), 2.40 (2H, m), 3.22 (2H, d), 3.45 (2H, m), 3.95 (2H, m), 4.25 (1H, m), 6.94 (1H, d), 7.01 (1H, d), 7.41 (1H, s), 11.1 (1H, s).

¹⁹F NMR δ (d⁶DMSO): 57.02

DESCRIPTION 37

4-Cyclopropyl-2-fluoro-1-nitrobenzene (D37)

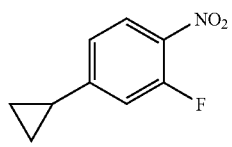

A mixture of 3-fluoro-4-nitrophenyltrifluoromethane-sulfonate (2.10 g, 7.3 mmole), cyclopropylboronic acid (0.69 g, 8.0 mmole), potassium fluoride (1.39 g, 24.0 mmole), sodium bromide (0.82 g, 8.0 mmole) and tetrakis(triphenylphosphine)palladium (0.25 g, 0.22 mmole) in toluene (100 ml) was stirred at reflux temperature under argon for 18 hrs. The cooled mixture was poured into water (100 ml) and extracted with ethyl acetate (2×75 ml). The combined organic extracts were washed with brine, dried (MgSO₄) and concentrated to dryness under vacuum. The residue was purified by silica gel chromatography eluting with 10-50% diethyl ether/40-60 pet ether to afford the product as yellow oil (0.98 g, 74%).

¹H NMR □ (CDCl₃): 0.83 (2H, m), 1.16 (2H, m), 1.96 (1H, m), 6.92 (2H, m), 7.97 (1H, t).

DESCRIPTION 38

1,1-Dimethylethyl-4-[(5-cyclopropyl-4-nitrophenyl)amino]-1-piperidinecarboxylate (D38)

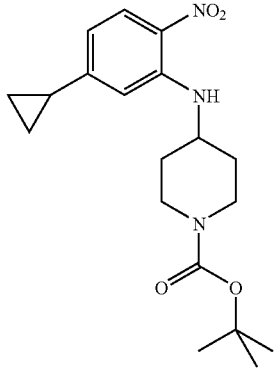

A stirred mixture of 4-cyclopropyl-2-fluoro-1-nitrobenzene (D37, 0.63 g, 3.5 mmole), 1-Boc-4-aminopiperidine (0.77 g, 3.9 mmole) and diisopropylethylamine (0.54 g, 4.2 mmole) in dry dimethylformamide (10 ml) was heated to 100° C. for 18 hrs. The solvent was removed by evaporation under vacuum and the residue partitioned between ethyl acetate and water. The organic phase was washed with water and brine, dried (MgSO₄) and concentrated to dryness under vacuum. The residue was purified by silica gel chromatography eluting with 10-60% diethyl ether/40-60 pet ether to afford the product as an orange gum (0.91 g, 72%).

¹H NMR □ (CDCl₃): 0.80 (2H, m), 1.08 (2H, m), 1.47 (9H, s), 1.56 (2H, m), 1.85 (1H, m), 2.04 (2H, bd), 3.06 (2H, bt), 3.69 (1H, m), 4.01 (2H, m), 6.20 (1H, d), 6.57 (1H, s), 8.06 (1H, s), 8.08 (1H, d).

DESCRIPTION 39

1,1-Dimethylethyl-4-[(2-amino-5-cyclopropylphenyl)amino]-1-piperidinecarboxylate (D39)

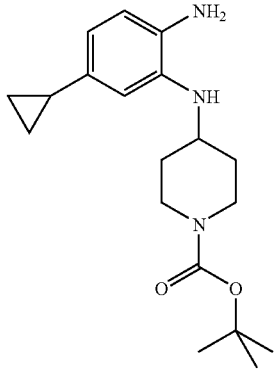

To a stirred mixture of 1,1-dimethylethyl-4-[(5-cyclopropyl-4-nitrophenyl)amino]-1-piperidinecarboxylate (D38, 0.20 g, 0.55 mmole) and Raney nickel (30 mg) in ethanol (5 ml) at 60° C. was added, dropwise over 15 mins, hydrazine hydrate. The mixture was then heated to reflux for 4 hrs. The cooled mixture was filtered and concentrated to dryness under vacuum. The residue was dissolved in ethyl acetate washed with water, dried (MgSO₄) and concentrated to dryness under vacuum to afford a purple gum (0.15 g, 82%). MH⁺=332.

¹H NMR ☐ (CDCl₃): 0.58 (2H, m), 0.84 (2H, m), 1.37 (1H, m), 1.47 (9H, s), 1.60 (2H, bs), 1.82 (1H, m), 2.02 (2H, bd), 2.97 (2H, bt), 3.31 (2H, bs), 3.41 (1H, m), 4.02 (2H, bs), 6.38 (1H, d), 6.44 (1H, s), 6.63 (1H, d).

DESCRIPTION 40

1,1-Dimethylethyl-4-(6-cyclopropyl-2-oxo-2,3-dihydro-1H-benzimidizol-1-yl)-1-piperidinecarboxylate (D40)

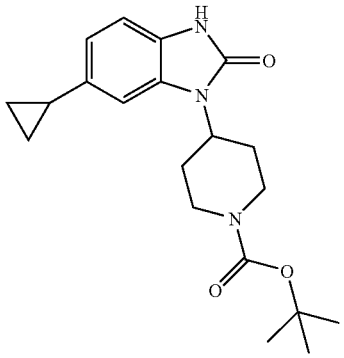

D40

A mixture of 1,1-dimethylethyl-4-[(2-amino-5-cyclopropylphenyl)amino]-1-piperidine carboxylate (D39, 0.75 g, 2.25 mmole) and 1,1'-carbonyldiimidazole (0.73 g, 4.5 mmole) in tetrahydrofuran (20 ml) was heated to reflux for 8 hrs. The cooled mixture was treated with ethyl acetate (25 ml) and washed with 1M citric acid, water and brine, dried (MgSO₄) and concentrated to dryness under vacuum to afford the crude product as a brown gum (0.93 g, >100%).

¹H NMR ☐ (CDCl₃): 0.58 (2H, m), 0.97 (2H, m), 1.50 (9H, s), 1.83 (2H, bd), 1.88 (1H, m), 2.34 (2H, bd), 2.87 (2H, bs), 4.41 (2H, bs), 4.45 (1H, m), 6.75 (1H, d), 6.88 (1H, s), 6.96 (1H, d), 8.82 (1H, s).

DESCRIPTION D41

6-Cyclopropyl-1-(4-piperidinyl)-1,3-dihydro-2H-benzimidazol-2-one (D41)

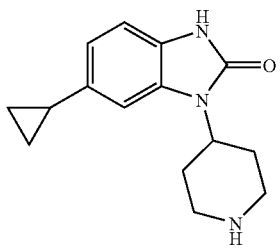

D41

A mixture of 1,1-dimethylethyl-4-(6-cyclopropyl-2-oxo-2,3-dihydro-1H-benzimidizol-1-yl)-1-piperidinecarboxylate (D40, 0.80 g, 2.24 mmole) and 6N HCl (3 ml) in ethanol (10 ml) was heated to reflux for 1 hr. The mixture was concentrated to dryness in vacuum and the residue was treated with sat. aq. potassium carbonate (10 ml) and extracted with ethyl acetate. The organic extract was dried (MgSO₄) and concentrated to dryness under vacuum. The residue was purified by silica gel chromatography eluting with dichloromethane/methanol/NH₄OH (100:15:2) to afford the product as a pale brown foam (0.48 g, 83%). MH⁺=258.

¹H NMR ☐ (CDCl₃): 0.68 (2H, m), 0.93 (2H, m), 1.83 (3H, bd), 1.95 (1H, m), 2.34 (2H, m), 2.78 (2H, t), 3.26 (2H, bd), 4.41 (1H, m), 6.75 (1H, d), 6.96 (1H, s), 7.05 (1H, d), 9.30 (1H, bs).

DESCRIPTION 42

4-[4-(6-Cyclopropyl-2-oxo-2,3-dihydro-1H-piperidinyl]-tetrahydro-2H-pyran-4-carbonitrile (D42)

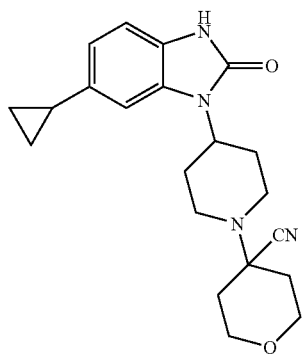

D42

Using a similar method to Description 36 the title compound was isolated as a colourless solid. MH⁺=367.

¹H NMR ☐ (d⁶DMSO): 0.78 (2H, m), 1.04 (2H, m), 1.80 (2H, m), 1.88 (2H, bd), 2.08 (1H, m), 2.32 (4H, m), 2.49-2.62 (2H, m), 3.38 (2H, d), 3.61 (2H, m), 4.08 (2H, d), 4.32 (1H, m), 6.82 (1H, d), 6.96 (1H, d), 7.13 (1H, s), 10.32 (1H, s).

DESCRIPTION 43

4-[4-(6-Methyl-2-oxo-2,3-dihydro-1H-benzimidazol-1-yl)-1-piperidinyl]tetrahydro-2H-pyran-4-carbonitrile (D43)

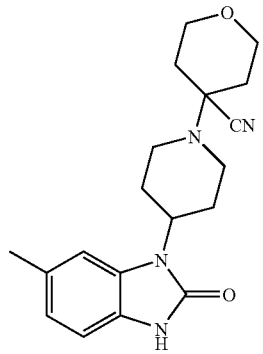

D43

6-Methyl-1-(4-piperidinyl)-1,3-dihydro-2H-benzimidazol-2-one hydrochloride salt (D14b, 1 g, 3.74 mmol) was dissolved in water (20 ml) and the pH of the solution was adjusted between 3 and 4. Tetrahydro-4H-pyran-4-one (0.455 g, 4.55 mmol) was added and the mixture stirred at room temperature for 10 minutes, then KCN (0.365 g, 5.61 mmol) was added and the solution was stirred at room temperature for 24 h. A white solid was collected by filtration, washed with cold water and dried in the oven (mixture 9:1 nitrile compound/starting material). This mixture was used without further purification (0.8 g, 2.35 mmol, 63% yield). MH⁺=341 and 342.

DESCRIPTION 44

N-(5-Cyclopropyl-2-nitrophenyl)-1-(tetrahydro-2H-pyran-4-yl)-4-piperidinamine (D44)

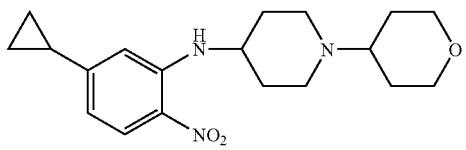

D44

A stirred mixture of 4-cyclopropyl-2-fluoro-1-nitrobenzene (D37, 180 mg, 0.99 mmol), 1-(tetrahydro-2H-pyran-4-yl)-4-piperidinamine dihydrochloride (diHCl salt of D9, 280 mg, 1.1 mmol) and N,N-diisopropylethylamine (0.56 ml, 3.3 mmol), in dimethylformamide (5 ml) was stirred at room temperature for 3 hrs, then heated at 90° C. for 18 hrs. The cooled mixture was concentrated under vacuum and the residue treated with dilute $K_2CO_3$ solution (20 ml) and extracted with ethyl acetate (3×30 ml). The combined extract was washed with water, dried ($MgSO_4$) and concentrated under vacuum. The residue was purified by chromatography on silica gel (40 g) eluting with 1-10% methanol/dichloromethane to afford the title compound as an orange solid (200 mg, 59%). M⁺+H=346.0.

¹H NMR δ (CDCl₃, 400 MHz): 0.75-0.82 (2H, m), 1.05-1.10 (2H, m), 1.55-1.80 (6H, m), 1.82-1.92 (1H, m), 2.05-2.15 (2H, m), 2.40-2.58 (3H, m), 2.85-2.95 (2H, m), 3.40 (2H, dt), 3.53-3.64 (1H, m), 4.05 (2H, dd), 6.20 (1H, dd), 6.56 (1H, d), 8.06 (1H, d), 8.21 (1H, d).

DESCRIPTION 45

4-Cyclopropyl-$N^2$-[1-(tetrahydro-2H-pyran-4-yl)-4-piperidinyl]-1,2-benzenediamine (D45)

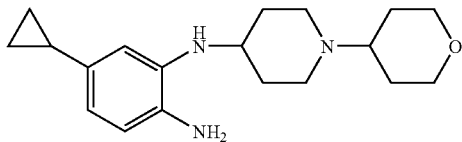

D45

A stirred mixture of N-(5-cyclopropyl-2-nitrophenyl)-1-(tetrahydro-2H-pyran-4-yl)-4-piperidinamine (D44, 150 mg, 0.43 mmol) and tin (II) chloride (326 mg, 1.72 mmol) in ethanol (10 ml) was treated with conc. HCl acid (~0.38 ml) and heated at reflux temperature with stirring for 18 hrs. The solvent was removed by concentration under vacuum and the residue treated with dilute $K_2CO_3$ solution and extracted with ethyl acetate, filtering the mixture to remove tin residues. The separated organic phase was washed with water and brine, dried ($MgSO_4$) and concentrated under vacuum to afford the title compound as a very pale brown sticky gum (114 mg, 83%). M⁺+H=316.1.

¹H-NMR δ (CDCl₃, 400 MHz): 0.55-0.62 (2H, m), 0.82-0.90 (2H, m), 1.45-2.00 (8H, m), 2.00-2.12 (2H, m), 2.35 (2H, dt), 2.45-2.55 (1H, m), 2.90-3.00 (2H, m), 3.0-3.4 (3H, br), 3.40 (2H, dt), 4.05 (2H, dd), 6.37 (1H, dd), 6.42 (1H, d), 6.62 (1H, d).

DESCRIPTION 46

2-Fluoro-4-[(1-methylethyl)oxy]-1-nitrobenzene (D46)

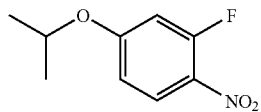

D46

A mixture of 5-fluoro-4-nitrophenol (314 mg, 2.0 mmol), propan-2-ol (120 mg, 2.0 mmol), diphenyl-2-pyridylphosphine (789 mg, 3.0 mmol) and di-tert-butyl azodicarboxylate (691 mg, 3.0 mmol) in tetrahydrofuran (15 ml) was stirred at room temperature under argon for 22 hrs. The mixture was treated with 1M HCl/diethyl ether (15 ml) and stirred at room temperature for 2 hrs, then concentrated under vacuum and the residue dissolved in diethyl ether (10 ml), treated with 5M HCl acid and stirred for 2 hrs. The organic layer was separated, washed with 5M HCl acid (15 ml), then 10% $Na_2CO_3$ solution (2×10 ml), dried ($MgSO_4$) and concentrated under vacuum. The residue was purified by chromatography on silica gel eluting with 5-70% ethyl acetate/60-80 petrol ether to afford the title compound as a yellow oil (276 mg, 69%).

DESCRIPTION 47

1,1-Dimethylethyl 4-({5-[(1-methylethyl)oxy]-2-nitrophenyl}amino)-1-piperidinecarboxylate (D47)

D47

A solution of 2-fluoro-4-[(1-methylethyl)oxy]-1-nitrobenzene (D46, 276 mg, 1.39 mmol) in dimethylformamide (10 ml) was treated with 1,1-dimethylethyl 4-amino-1-piperidinecarboxylate (278 mg, 1.39 mmol) and diisopropylethylamine (0.241 ml, 1.39 mmol) and stirred at approx. 80° C. for 17 hrs. The mixture was concentrated under vacuum and the residue treated with water and extracted with a mixture of ethyl acetate/diethyl ether (×2). The combined extract was dried and concentrated under vacuum to afford the title compound as a yellow oil/solid (514 mg, 97%).

DESCRIPTION 48

1,1-Dimethylethyl 4-({2-amino-5-[(1-methylethyl)oxy]phenyl}amino)-1-piperidinecarboxylate (D48)

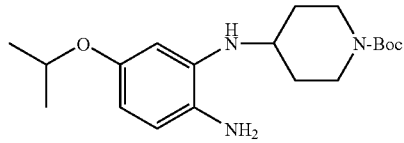

D48

A partial solution of 1,1-dimethylethyl 4-({5-[(1-methylethyl)oxy]-2-nitrophenyl}amino)-1-piperidinecarboxylate (D47, 514 mg, 1.35 mmol) in ethanol (20 ml) was treated with Raney Nickel followed by dropwise addition of a solution of hydrazine hydrate (0675 ml, 13.5 mmol) in ethanol. The mixture was heated at 45° C. for 2 hrs, then the Raney Nickel was filtered off washing with ethanol and the filtrate concentrated under vacuum to afford the title compound as a violet coloured oil (470 mg, 99%).

DESCRIPTION 49

1,1-Dimethylethyl 4-{6-[(1-methylethyl)oxy]-2-oxo-2,3-dihydro-1H-benzimidazol-1-yl}-1-piperidinecarboxylate (D49)

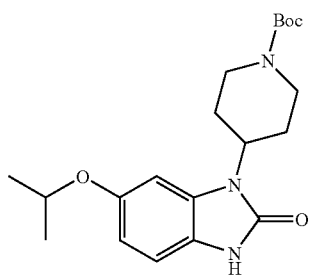

A solution of 1,1-dimethylethyl 4-({2-amino-5-[(1-methylethyl)oxy]phenyl}amino)-1-piperidinecarboxylate (D48, 470 mg, 1.34 mmol) in tetrahydrofuran (5 ml) was treated with N,N'-carbonyldiimidazole (322 mg, 2.01 mmol) and heated at 50° C. for 17 hrs. The mixture was concentrated under vacuum and the residue treated with $Na_2CO_3$ solution (10 ml) and extracted with ethyl acetate (2×20 ml). The combined extract was dried ($MgSO_4$), concentrated under vacuum and the residue purified by chromatography on silica gel eluting with 5-60% ethyl acetate/60-80 petrol ether to afford the title compound as a dark orange oil (351 mg, 69%). $M^+–H=374.3$.

DESCRIPTION 50

6-[(1-Methylethyl)oxy]-1-(4-piperidinyl)-1,3-dihydro-2H-benzimidazol-2-one (D50

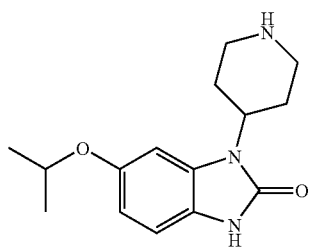

A solution of 1,1-dimethylethyl 4-{6-[(1-methylethyl)oxy]-2-oxo-2,3-dihydro-1H-benzimidazol-1-yl}-1-piperidinecarboxylate (D49, 351 mg, 0.93 mmol) in dichloromethane (5 ml) was treated with trifluoroacetic acid (3 ml) and stirred under argon for 1 hr. The mixture was concentrated under vacuum and the residue treated with 10% $Na_2CO_3$ solution and extracted with ethyl acetate (×3). The combined extract was concentrated under vacuum to leave the title compound as an orange oil (229 mg, 89%). $M^++H=276.1$.

DESCRIPTION 51

5-[(Difluoromethyl)oxy]-2-iodoaniline (D51)

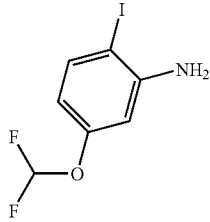

A solution of 3-[(difluoromethyl)oxy]aniline (3.16 g), iodine monochloride (3.9 g) and sodium acetate (6.5 g) in acetic acid (30 ml) was stirred for 1 hour, then partitioned between saturated sodium bicarbonate solution and ether. The ether layer was separated, washed consecutively with sodium thiosulphate solution and brine. The solvent was removed and the residue was loaded onto a silica gel and chromatographed on silica gel eluted with hexane/ethyl acetate 0-20% to give the title compound as a red oil (2.9 g). Mass Spectrum 286 M+H+

DESCRIPTION 52

1,1-Dimethylethyl 4-{[({4-[(difluoromethyl)oxy]-2-iodophenyl}amino)carbonyl]amino}-1-piperidinecarboxylate (D52)

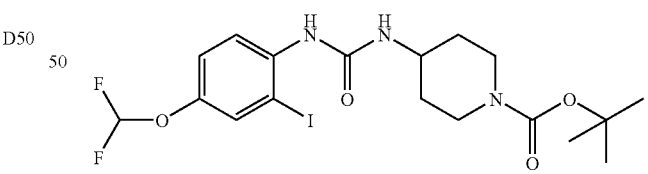

A solution of 5-[(difluoromethyl)oxy]-2-iodoaniline (D51, 2.88 g) in 1,4-dioxane (15 ml) was treated with bis(trichloromethyl) carbonate (1 g). The mixture was heated at reflux for 2 hours. The solvent was evaporated and the residue was dissolved in dichloromethane (40 ml) and 1,1-dimethylethyl 4-amino-1-piperidinecarboxylate (2.3 g) was added. The mixture was stirred overnight at room temperature. Silica gel was added and the solvent was evaporated. The residue was loaded onto a silica gel chromatography column which was eluted with hexane/ethyl acetate 0-50% to give the title compound. (1.38 g)

¹HNMR (d⁶DMSO, 400 MHz): 1.25 (2H, m), 1.40 (9H, s), 1.80 (2H, m), 2.9 (2H, broad), 3.62 (1H, m), 3.80 (2H, m), 7.05 (1H, d), 7.14 (1H, m), 7.16 (1H, t) 7.53 (1H, s), 7.60 (1H, s), 7.82 (1H, s).

DESCRIPTION 53

1,1-Dimethylethyl 4-{6-[(difluoromethyl)oxy]-2-oxo-2,3-dihydro-1H-benzimidazol-1-yl}-1-piperidinecarboxylate (D53)

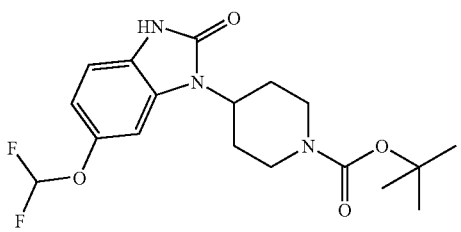

A solution of tris(dibenzylideneacetone)dipalladium (0) (0.18 g), 1,1'-bis(diphenylphosphino)ferrocene (0.10 g), sodium tert-butoxide (0.6 g) in 1,4-dioxane (10 ml) was stirred under an atmosphere of argon for 10 minutes. 1,1-Dimethylethyl 4-{[({4-[(difluoromethyl)oxy]-2-iodophenyl}amino)carbonyl]amino}-1-piperidinecarboxylate (D52, 1.3 g) was added and the mixture was heated to 90° C. The mixture was stirred at this temperature overnight. The mixture was poured into dichloromethane which was washed with water and brine. The solvent was removed and the residue was chromatographed on silica gel eluted with ethyl acetate/hexane 0-50% to give the title compound as a off-white solid. (0.54 g).

¹HNMR (d⁶DMSO, 400 MHz): 1.43 (9H, s), 1.66 (2H, s), 2.22 (2H, m), 2.9 (2H, broad), 4.07 (2H, m), 4.32 (1H, m), 6.79 (1H, d of d), 6.95 (1H, d), 7.10 (1H, t) 7.11 (1H, d).

DESCRIPTION 54

6-[(Difluoromethyl)oxy]-1-(4-piperidinyl)-1,3-dihydro-2H-benzimidazol-2-one hydrochloride (D54)

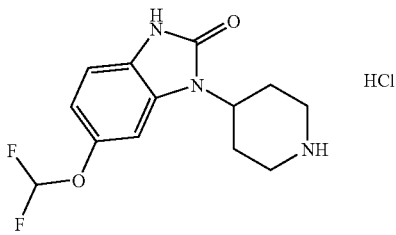

A solution of 1,1-dimethylethyl 4-{6-[(difluoromethyl)oxy]-2-oxo-2,3-dihydro-1H-benzimidazol-1-yl}-1-piperidinecarboxylate (D53, 0.54 g) in methanol (5 ml) was treated with a saturated solution of hydrogen chloride in ethanol (5 ml). The mixture was stirred for 1 hour when the solvent was removed to give the title compound as a white solid (0.45 g). Mass Spectrum 284 M+H+

¹HNMR (d⁶DMSO, 400 MHz): 1.84 (2H, m), 2.59 (2H, m), 3.10 (2H, m), 3.40 (2H, m), 4.5 (1H, m), 6.83 (1H, d of d), 7.00 (1H, d), 7.22 (1H, t), 7.40 (1H, d), 8.9 (2H, br s), 11.2 (1H, s).

DESCRIPTION 55

2-Fluoro-1-nitro-4-[(2,2,2-trifluoroethyl)oxy]benzene (D55)

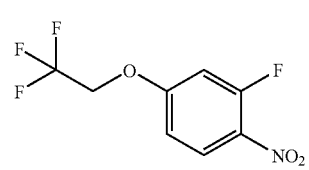

A stirred solution of 3-fluoro-4-nitrophenol (200 mg, 1.3 mmol) in dimethylformamide (3 ml) at 0° C. under argon was treated portionwise with sodium hydride (60 mg of 60% oil dispersion, 1.5 mmol) and maintained for 20 minutes. The mixture was treated with trifluoroethyl triflate (325 mg, 1.4 mmol), then allowed to warm to room temperature and stir overnight. The yellow solution was treated with water (40 ml) and brine (5 ml) and extracted with ethyl acetate. The extract was washed with water, dried (Na₂SO₄) and concentrated under vacuum to leave the title compound as a yellow oil (280 mg, 92%).

¹H-NMR δ (CDCl₃, 400 MHz): 4.45 (2H, q), 6.82-6.90 (2H, m), 8.15 (1H, t).

DESCRIPTION 56

N-{2-Nitro-5-[(2,2,2-trifluoroethyl)oxy]phenyl}-1-(tetrahydro-2H-pyran-4-yl)-4-piperidinamine (D56)

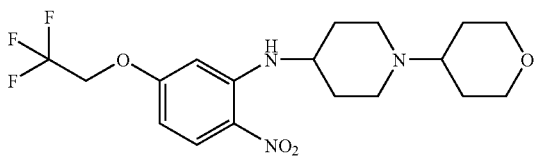

A stirred suspension of 1-(tetrahydro-2H-pyran-4-yl)-4-piperidinamine dihydrochloride (diHCl salt of D9, 350 mg, 1.4 mmol) in dimethylformamide (6 ml) at room temperature under argon was treated with N,N-diisopropylethylamine 51 mg, 4.0 mmol), then stirred for 10 minutes before adding 2-fluoro-1-nitro-4-[(2,2,2-trifluoroethyl)oxy]benzene (D55, 280 mg, 1.2 mmol) and heating at 75° C. for 36 hrs. The solution was concentrated under vacuum and the residue treated with 10% Na₂CO₃ solution and extracted with ethyl acetate. The extract was washed with brine, dried (Na₂SO₄) and concentrated under vacuum. The residue was purified by chromatography on silica gel (20 g) eluting with 0-20% methanol/ethyl acetate to afford the title compound as a bright yellow solid (210 mg, 45%).

¹H-NMR δ (CDCl₃, 400 MHz): 1.55-1.80 (6H, m), 2.05-2.16 (2H, m), 2.40-2.58 (3H, m), 2.85-2.95 (2H, m), 3.40 (2H, dt), 3.45-3.56 (1H, m), 4.05 (2H, dd), 4.40 (2H, q), 6.22 (1H, dd), 6.27 (1H, d), 8.20 (1H, d), 8.29 (1H, d).

DESCRIPTION 57

N²-[1-(Tetrahydro-2H-pyran-4-yl)-4-piperidinyl]-4-[(2,2,2-trifluoroethyl)oxy]-1,2-benzenediamine (D57)

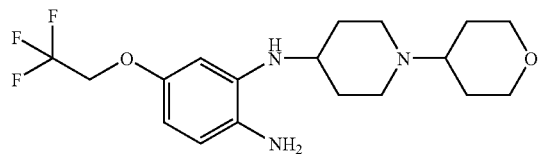

A stirred solution of N-{2-nitro-5-[(2,2,2-trifluoroethyl)oxy]phenyl}-1-(tetrahydro-2H-pyran-4-yl)-4-piperidinamine (D56, 210 mg, 0.52 mmol) in ethanol (15 ml) at room temperature under argon was treated with Raney Nickel (20 mg) followed by dropwise addition of hydrazine hydrate (0.16 ml, 5.0 mmol). The mixture was maintained at room temperature for 1 hr, then filtered through Kieselguhr and the filtrate concentrated under vacuum to leave the title compound as a pale grey solid (190 mg, 98%).

¹H-NMR δ (CDCl₃, 400 MHz): 1.46-1.70 (4H, m), 1.75-1.82 (2H, m), 21.0 (2H, br d), 2.38 (2H, br t), 2.48-2.60 (1H, m), 2.85-3.20 (2H, br s), 2.98 (2H, br d), 3.20-3.30 (1H, m), 3.39 (2H, dt), 3.60 (1H, br s), 4.05 (2H, dd), 4.27 (2H, q), 6.14 (1H, dd), 6.31 (1H, d), 6.65 (1H, d).

DESCRIPTION 58

4-Nitro-3-{[1-(tetrahydro-2H-pyran-4-yl)-4-piperidinyl]amino}benzonitrile (D58)

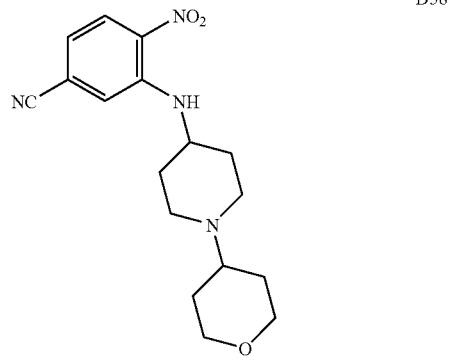

4-Cyano-2-fluoro-1-nitrobenzene (300 mg, 0.0018 mol, 1 eq), 1-(tetrahydro-2H-pyran-4-yl)-4-piperidinamine (D9, 330 mg, 0.0018 mol, 1 eq), diisopropylethylamine (350 mg, 0.0027 mol, 1.5 eq), and dimethylformamide (5 ml) were combined, heated to 200° C. and held for 1 min in a microwave reactor. 100 ml of water was then added and the reaction extracted with 2×75 ml dichloromethane. The dichloromethane layers were combined, dried with sodium sulfate, and evaporated to yield the title compound which was used without further purification in the next step. MS (ESI): 331 [M+H]+.

DESCRIPTION 59

4-Amino-3-{[1-(tetrahydro-2H-pyran-4-yl)-4-piperidinyl]amino}-benzonitrile (D59)

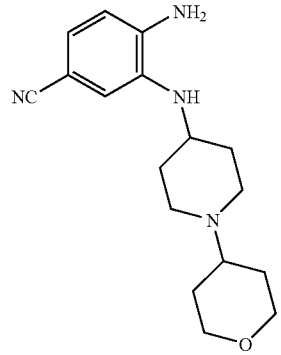

4-Nitro-3-{[1-(tetrahydro-2H-pyran-4-yl)-4-piperidinyl]amino}benzonitrile (D58, 592 mg, 0.0018 mol, 1 eq), 10% palladium on carbon (200 mg, 0.00018 mol, 0.1 eq), ammonium formate (375 mg, 0.0057 mol, 3.2 eq), and methanol (15 ml) (degassed with nitrogen) were combined and stirred for 1 hour. The catalyst was then filtered off, and the reaction evaporated, water and dichloromethane added and shaken. Separation and drying of the dichloromethane layer with sodium sulfate followed by evaporation yielded a crude product which was purified exactly as in Example 1 where A=H₂O and B=acetonitrile to afford the title compound. MS (ESI): 301 [M+H]+

Example 1

1-[1-(Tetrahydro-2H-pyran-4-yl)-4-piperidinyl]-1,3-dihydro-2H-benzimidazol-2-one trifluoroacetate (E1)

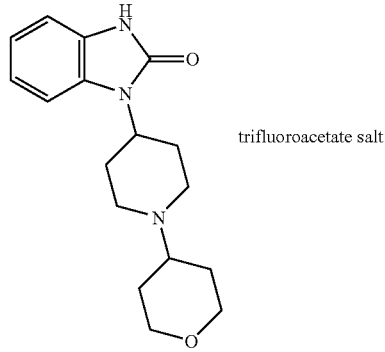

trifluoroacetate salt 260 mg (0.0012 mol, 1 eq) of commercially available 4-(2-keto-1-benzimidazolinyl)piperidine, 215 mg (0.0036 mol, 3 eq) of acetic acid (AcOH), 510 mg (0.0024 mol, 2 eq) of sodium triacetoxyborohydride, and 360 mg (0.0036 mol, 3 eq) of tetrahydro-4H-pyran-4-one were combined in 45 mL of dichloroethane (DCE), and the mixture was stirred overnight. The mixture was then evaporated, and the residue dissolved in 2 mL of methanol (MeOH) and purified via HPLC using a Gilson preparative HPLC system with a Waters Xterra MS C18 column, 100 mm by 50 mm ID, 5 μm, eluting with 5% B to 75% B in 10 min, where A=H₂O (0.1% trifluoroacetic acid) and B=CH₃CN (0.1% trifluoroacetic acid) pumped at 150 mL/min, to produce 363 mg (73% yield) 1-[1-(tetrahydro-2H-pyran-4-yl)-4-piperidinyl]-1,3-dihydro-2H-benzimidazol-2-one trifluoroacetate as a white solid. $^1$H-NMR (TFA salt) (400 MHz, DMSO-d₆): δ 10.94 (s, 1H), 9.55 (br s, 1H), 7.32-7.27 (m, 1H), 7.06-6.99 (m, 3H), 4.56 (m, 1H), 4.00 (m, 2H), 3.62 (m, 2H), 3.49 (m, 1H), 3.35 (m, 2H), 3.22 (m, 2H), 2.67 (m, 2H), 1.97 (m, 4H), 1.71 (m, 2H); MS (ESI): 302 [M+H]⁺.

Example 2

6-Fluoro-1-[1-(tetrahydro-2H-pyran-4-yl)-4-piperidinyl]-1,3-dihydro-2H-benzimidazol-2-one trifluoroacetate (E2)

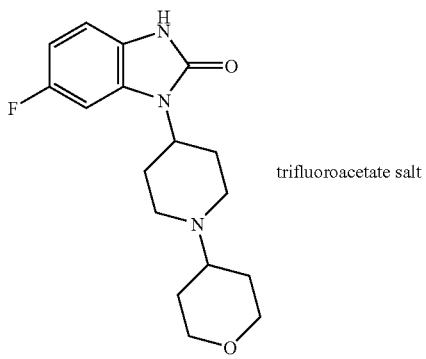

trifluoroacetate salt

Substituting the above obtained 6-fluoro-1-piperidin-4-yl-1,3-dihydro-benzoimidazol-2-one D4 for 4-(2-keto-1-benzimidazolinyl)piperidine and proceeding exactly as described in Example 1, a 61% yield of 6-fluoro-1-[1-(tetrahydro-2H-pyran-4-yl)-4-piperidinyl]-1,3-dihydro-2H-benzimidazol-2-one trifluoroacetate was produced as a white solid. $^1$H-NMR (TFA salt) (400 MHz, DMSO-d₆): δ 11.00 (s, 1H), 9.44 (br s, 1H), 7.23 (dd, J=2.4, 9.6 Hz, 1H), 6.98 (dd, J=4.8, 8.4 Hz, 1H), 6.84 (m, 1H), 4.54 (m, 1H), 4.01 (m, 2H), 3.62 (m, 2H), 3.50 (m, 1H), 3.34 (m, 2H), 3.19 (m, 2H), 2.63 (m, 2H), 1.97 (m, 4H), 1.71 (m, 2H); MS (ESI): 320 [M+H]+.

Example 3

6-Chloro-1-[1-(tetrahydro-2H-pyran-4-yl)-4-piperidinyl]-1,3-dihydro-2H-benzimidazol-2-one trifluoroacetate (E3)

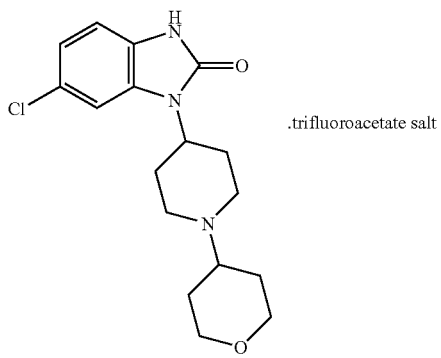

.trifluoroacetate salt

Substituting 6-chloro-1-piperidin-4-yl-1,3-dihydro-benzoimidazol-2-one D8 for 4-(2-keto-1-benzimidazolinyl)piperidine and proceeding exactly as described in Example 1, a 67% yield of 6-chloro-1-[1-(tetrahydro-2H-pyran-4-yl)-4-piperidinyl]-1,3-dihydro-2H-benzimidazol-2-one trifluoroacetate was produced as a white solid. $^1$H-NMR (TFA salt) (400 MHz, dmso-d₆): δ 11.11 (s, 1H), 9.23 (brs, 1H), 7.38 (s, 1H), 7.04 (d, J=8.0 Hz, 1H), 6.99 (d, J=8.0 Hz, 1H), 4.54 (m, 1H), 4.00 (m, 2H), 3.62 (m, 2H), 3.49 (m, 1H), 3.31 (m, 2H), 3.19 (m, 2H), 2.62 (m, 2H), 1.97 (m, 4H), 1.76 (m, 2H); MS (ESI): 336 [M+H]+.

Example 3 Alternative Procedure

6-Chloro-1-[1-(tetrahydro-2H-pyran-4-yl)-4-piperidinyl]-1,3-dihydro-2H-benzimidazol-2-one hydrochloride (E3)

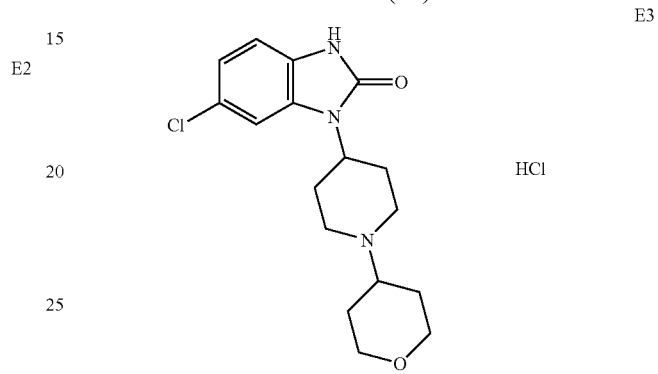

6-Chloro-5-fluoro-1-(4-piperidinyl)-1,3-dihydro-2H-benzimidazol-2-one hydrochloride (2.0 g), Ti(iPrO)₄ (4.2 mL), and tetrahydro-4H-pyran-4-one (1.4 g) were stirred together at room temperature for 1 h; dry methanol (30 mL) followed by NaBH₃CN (0.8 g) were added and the mixture was stirred at room temperature for 1 h. The crude mixture was then quenched with methanol and it was purified first by SCX column chromatography followed by filtration and silica gel chromatography (methanol-NH₃-dichloromethane). Conversion to the hydrochloride gave the title compound, 950 mg, MH⁺=336 and 338, $^1$H NMR (HCl salt) (DMSO-d6) 1.72 (2H, m), 1.94 (2H, m), 2.03 (2H, m), 2.81 (2H, m), 3.20 (2H, m), 3.33 (2H, m), 3.44 (1H, m), 4.01 (2H, m), 4.61 (1H, m), 7.02 (2H, m), 7.66 (1H, s), 10.52 (1H, bs) and 11.12 (1H, s).

Example 4

6-Bromo-1-[1-(tetrahydro-2H-pyran-4-yl)-4-piperidinyl]-1,3-dihydro-2H-benzimidazol-2-one hydrochloride (E4)

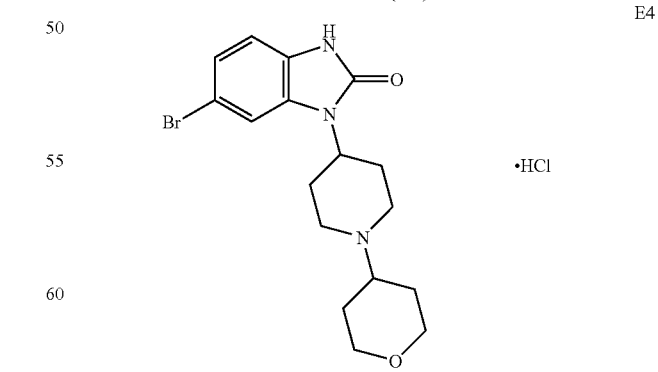

360 mg (0.001 mol, 1 eq) of 2-amino-5-bromophenyl)[1-(tetrahydro-2H-pyran-4-yl)-4-piperidinyl]amine D11, 200 mg (0.0016 mol, 1.6 eq) of diisopropylethylamine, 91 mg (0.000306 mol, 0.3 eq) of triphosgene, and 20 mL of dichloroethane were combined. After 5 min, 4 mL of 4 M HCl in dioxane was added and the resulting reaction mixture was evaporated. The residue was dissolved in 2 mL of methanol and purified exactly as in Example 1, where A=H$_2$O and B=acetonitrile to produce 182 mg (43% yield) of 6-bromo-1-[1-(tetrahydro-2H-pyran-4-yl)-4-piperidinyl]-1,3-dihydro-2H-benzimidazol-2-one hydrochloride as a light rose colored solid. $^1$H-NMR (HCl salt) (400 MHz, DMSO-d$_6$): δ 11.16 (s, 1H), 11.02 (br s, 1H), 7.87 (s, 1H), 7.16 (d, J=8.4 Hz, 1H), 6.95 (d, J=8.4 Hz, 1H), 4.60 (m, 1H), 3.99 (m, 2H), 3.59 (m, 2H), 3.50-3.30 (m, 3H), 3.19 (m, 2H), 2.83 (m, 2H), 2.05 (m, 2H), 1.91 (m, 2H), 1.76 (m, 2H); MS (ESI): 380 [M+H]+.

Example 5

6-Methyl-1-[1-(tetrahydro-2H-pyran-4-yl)-4-piperidinyl]-1,3-dihydro-2H-benzimidazol-2-one trifluoroacetate (E5)

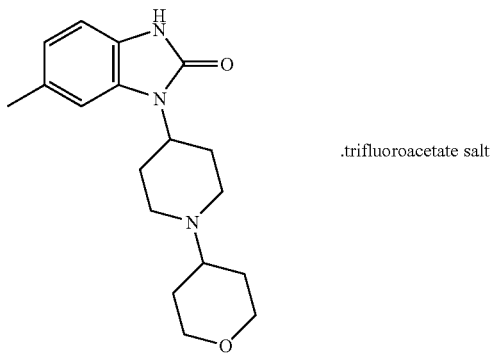

.trifluoroacetate salt

Substituting 6-methyl-1-piperidin-4-yl-1,3-dihydro-benzoimidazol-2-one D14 for 4-(2-keto-1-benzimidazolinyl)piperidine and proceeding exactly as described in Example 1, a 51% yield of 6-methyl-1-[1-(tetrahydro-2H-pyran-4-yl)-4-piperidinyl]-1,3-dihydro-2H-benzimidazol-2-one trifluoroacetate was produced as a white solid. $^1$H-NMR (TFA salt) (400 MHz, DMSO-d$_6$): δ 10.78 (s, 1H), 9.26 (br s, 1H), 7.07 (s, 1H), 6.87 (d, J=8.0 Hz, 1H), 6.81 (d, J=8.0 Hz, 1H), 4.50 (m, 1H), 3.98 (m, 2H), 3.61 (m, 2H), 3.49 (m, 1H), 3.33 (m, 2H), 3.20 (m, 2H), 2.66 (m, 2H), 2.34 (s, 3H), 1.96 (m, 4H), 1.70 (m, 2H); MS (ESI): 316 [M+H]+.

Example 5 Alternative Procedure

6-Methyl-1-[1-(tetrahydro-2H-pyran-4-yl)-4-piperidinyl]-1,3-dihydro-2H-benzimidazol-2-one hydrochloride (E5)

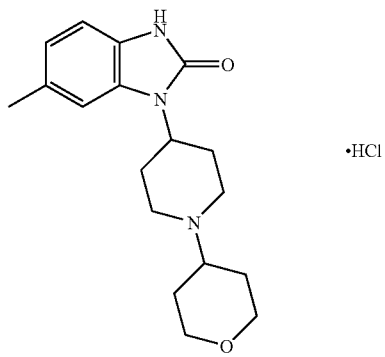

•HCl

From 6-methyl-1-(4-piperidinyl)-1,3-dihydro-2H-benzimidazol-2-one hydrochloride (280 mg) using the method of Example 3 Alternative Procedure to give the title compound, 170 mg, MH+=316, $^1$H NMR (HCl salt) (DMSO-d6) 1.75 (2H, m), 1.87 (2H, m), 2.03 (2H, m), 2.32 (3H, s), 2.88 (2H, m), 3.20 (2H, m), 3.35 (2H, m), 3.52 (1H, m), 4.58 (1H, m), 6.81 (2H, m), 7.51 (1H, s), 10.78 (1H, s) and 10.82 (1H, bs).

Example 6

6-(Methoxy)-1-[1-(tetrahydro-2H-pyran-4-yl)-4-piperidinyl]-1,3-dihydro-2H-benzimidazol-2-one trifluoroacetate (E6)

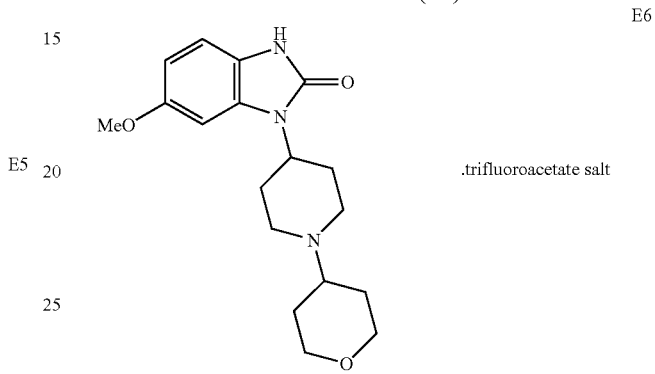

.trifluoroacetate salt

Substituting 6-methoxy-1-piperidin-4-yl-1,3-dihydro-benzoimidazol-2-one D19 for 4-(2-keto-1-benzimidazolinyl)piperidine and proceeding exactly as described in Example 1, a 53% yield of 6-(methyloxy)-1-[1-(tetrahydro-2H-pyran-4-yl)-4-piperidinyl]-1,3-dihydro-2H-benzimidazol-2-one trifluoroacetate was produced as a white solid. $^1$H-NMR (TFA salt) (400 MHz, DMSO-d$_6$): δ 10.73 (s, 1H), 9.41 (br s, 1H), 6.96 (d, J=2.4 Hz, 1H), 6.90 (d, J=8.4 Hz, 1H), 6.61 (dd, J=2.4, 8.4 Hz, 1H), 4.52 (m, 1H), 4.00 (m, 2H), 3.75 (s, 3H), 3.62 (m, 2H), 3.49 (m, 1H), 3.35 (m, 2H), 3.20 (m, 2H), 2.66 (m, 2H), 1.96 (m, 4H), 1.71 (m, 2H); MS (ESI): 332 [M+H]+.

Example 7

1-[1-(Tetrahydro-2H-pyran-4-yl)-4-piperidinyl]-6-(trifluoromethyl)-1,3-dihydro-2H-benzimidazol-2-one trifluoroacetate (E7)

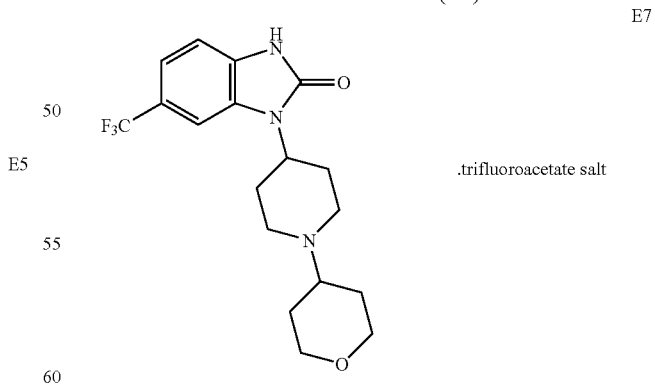

.trifluoroacetate salt

Substituting 1-piperidin-4-yl-6-trifluoromethyl-1,3-dihydro-benzoimidazol-2-one D23 for 4-(2-keto-1-benzimidazolinyl)piperidine and proceeding exactly as described in Example 1, a 54% yield of 1-[1-(tetrahydro-2H-pyran-4-yl)-4-piperidinyl]-6-(trifluoromethyl)-1,3-dihydro-2H-benzimidazol-2-one trifluoroacetate was produced as a white solid.

¹H-NMR (TFA salt) (400 MHz, DMSO-d₆): δ 11.41 (s, 1H), 9.45 (br s, 1H), 7.57 (s, 1H), 7.38 (d, J=8.0 Hz, 1H), 7.18 (d, J=8.0 Hz, 1H), 4.62 (m, 1H), 4.01 (m, 2H), 3.63 (m, 2H), 3.49 (m, 1H), 3.35 (m, 2H), 3.20 (m, 2H), 2.67 (m, 2H), 2.00 (m, 4H), 1.71 (m, 2H); MS (ESI): 370 [M+H]+.

Example 8

6-Ethyl-1-[1-(tetrahydro-2H-pyran-4-yl)-4-piperidinyl]-1,3-dihydro-2H-benzimidazol-2-one hydrochloride (E8)

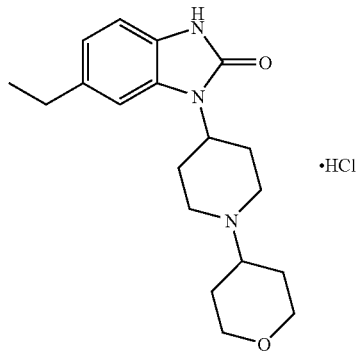

E8

To a solution of (2-amino-5-ethylphenyl)[1-(tetrahydro-2H-pyran-4-yl)-4-piperidinyl]amine D26 (251 mg, 0.83 mmol) in dichloromethane (10 mL) was added 1,1'-carbonyldiimidazole (403 mg, 2.49 mmol). The mixture was stirred under room temperature for 1 hour and 2 mL of 4 M HCl in 1,4-dioxane was added. The resulting mixture was stirred for 5 min and concentrated in vacuo. The residue was dissolved in MeOH and purified by using a Gilson preparative HPLC system with a Waters Xterra (C-18) column 100 mm by 50 mm ID, eluting with 10% B to 90% B in 10 min, where A=H₂O and B=CH₃CN pumped at 150 mL/min to yield 89 mg of the title compound (29% yield). MS (ESI): 330 [M+H]+; ¹H NMR (HCl salt) (400 MHz, CDCl₃): δ 1.30 (3H, t), 1.99 (5H, m), 2.25 (2H, d), 2.75 (2H, q), 3.03 (2H, m), 3.44 (4H, d), 3.68 (2H, m), 4.14 (2H, d), 4.69 (1H, m), 6.91 (1H, d), 7.00 (1H, d), 7.84 (1H, s), 9.36 (1H, s), 12.91 (1H, br).

Example 9

1-[1-(Tetrahydro-2H-pyran-4-yl)-4-piperidinyl]-6-[(trifluoromethyl)oxy]-1,3-dihydro-2H-benzimidazol-2-one hydrochloride (E9)

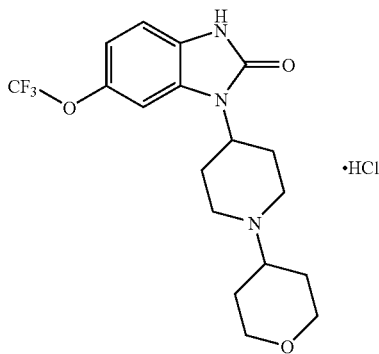

E9

1-(4-Piperidinyl)-6-[(trifluoromethyl)oxy]-1,3-dihydro-2H-benzimidazol-2-one hydrochloride D32 (0.6 g) 1,2-dichloroethane (50 mL) and triethylamine (10 mL), tetrahydro-4H-pyran-4-one (1.2 g), sodium triacetoxyborohydride (1.3 g) was stirred at room temperature over night. The mixture was poured into dilute ammonium chloride solution and extracted with dichloromethane. The organic phase was separated, washed with brine and dried with hydromatrix. The solvent was removed and the residue was chromatographed on silica gel eluted with dichloromethane/2M ammonia in methanol 0-10%. The resulting product was dissolved in a mixture of methanol and dichloromethane, treated with 1M hydrogen chloride in ether and the solvent was removed. Recrystallisation from methanol gave the title compound as a white solid (0.28 g).

Mass Spectrum MH⁺ 386

¹H NMR (HCl salt) (DMSO, 400 MHz) 1.76 (2H, m), 1.95 (2H, m), 2.03 (2H, m), 2.79 (2H, m), 3.14 (2H, m), 3.20 (2H, m), 3.43 (1H, m), 3.48 (2H, m), 3.98 (2H, m), 4.59 (1H, m), 6.99 (1H, d), 7.05 (1H, d), 7.60 (1H, s), 10.5 (1H, s broad), 11.2 (1H, s).

Example 10

6-(1-Methylethyl)-1-[1-(tetrahydro-2H-pyran-4-yl)-4-piperidinyl]-1,3-dihydro-2H-benzimidazol-2-one hydrochloride E10

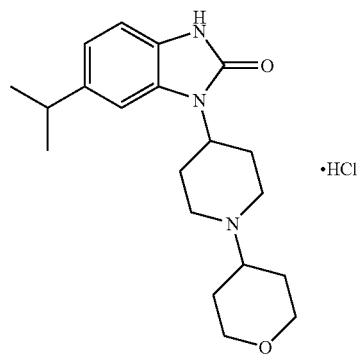

E10

6-(1-Methylethyl)-1-(4-piperidinyl)-1,3-dihydro-2H-benzimidazol-2-one hydrochloride D35 (0.59 g) 1,2-dichloroethane (50 mL) and triethylamine (3 mL), tetrahydro-4H-pyran-4-one (0.9 g), sodium triacetoxyborohydride (1.9 g) was stirred at room temperature overnight. The mixture was poured into dilute ammonium chloride solution and extracted with dichloromethane. The organic phase was separated, washed with brine and dried with hydromatrix. The solvent was removed and the residue was chromatographed on silica gel eluted with dichloromethane/2M ammonia in methanol 0-10%. The resulting product was dissolved in a mixture of methanol and dichloromethane, treated with 1M hydrogen chloride in ether and the solvent was removed. Recrystallisation from methanol gave the title compound as a white solid from ether (0.486 g). Mass Spectrum MH⁺ 344

¹H NMR (HCl salt) (DMSO, 400 MHz) 1.23 (6H, m), 1.8 (4H, m), 2.08 (2H, m), 2.94 (3H, m), 3.20 (2H, m), 3.31 (3H, m), 3.58 (2H, m), 4.00 (2H, m), 4.59 (1H, m), 6.89 (2H, m), 7.57 (1H, s), 10.75 (1H, s broad), 11.3 (1H, br s).

Example 11

6-Methyl-1-[1-(4-methyltetrahydro-2H-pyran-4-yl)-4-piperidinyl]-1,3-dihydro-2H-benzimidazol-2-one hydrochloride (E11)

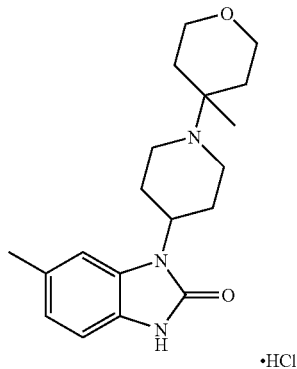

E11

·HCl

A stirred solution of 3M methylmagnesium bromide in diethyl ether (0.5 ml 1.5 mmol), was treated with a tetrahydrofuran (10 ml) solution of 4-[4-(6-methyl-2-oxo-2,3-dihydro-1H-benzimidazol-1-yl)-1-piperidinyl]tetrahydro-2H-pyran-4-carbonitrile (D43, 0.12 g, 0.45 mmol) under argon at room temperature for 2 h. The reaction mixture was cooled to 0° C. and 1M NH$_4$Cl solution (3 ml) was added dropwise. The mixture was partially concentrated, then extracted with dichloromethane (10 ml, 3 times). The organic layer was dried (MgSO$_4$) and concentrated to leave a solid. The crude material was dissolved in dichloromethane (5 ml) and purified with isocyanate resin, to leave 85 mg of pure compound. The hydrochloride salt was prepared by the addition of 1 ml of HCl in diethyl ether to the solution of the free base in dichloromethane. (94 mg, 0.29 mmol, 63% yield). MH$^+$=330 and 331

$^1$H NMR (HCl salt) δ (MeOD, 400 MHz): 1.5 (3H, s), 1.9 (4H, m), 2.1 (2H, m), 2.4 (3H, s), 2.8 (2H, s) 3.3 (2H, m), 3.6 (2H, m), 3.8 (2H, m), 4.0 (2H, m), 4.6 (1H, s), 6.9 (1H, d), 7.0 (1H, d), 7.2 (1H, s).

Example 12

1-[1-(4-Ethyltetrahydro-2H-pyran-4-yl)-4-piperidinyl]-6-methyl-1,3-dihydro-2H-benzimidazol-2-one hydrochloride (E12)

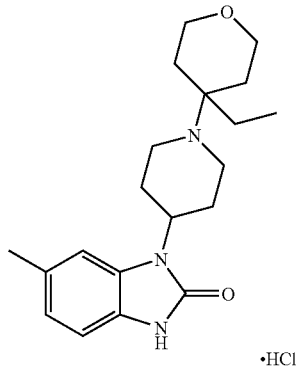

E12

·HCl

A stirred solution of 1M ethylmagnesium bromide in tetrahydrofuran (2 ml, 2 mmol), was treated with a tetrahydrofuran (6 ml) solution of 4-[4-(6-methyl-2-oxo-2,3-dihydro-1H-benzimidazol-1-yl)-1-piperidinyl]tetrahydro-2H-pyran-4-carbonitrile (D43, 0.064 g, 0.19 mmol) under argon at room temperature for 24 h. The reaction mixture was cooled to 0° C. and 1M NH$_4$Cl solution (5 ml) was added dropwise. The mixture was partially concentrated, then extracted with dichloromethane (10 ml, 3 times). The organic layer was dried (MgSO$_4$) and concentrated to leave a solid. The hydrochloride salt was prepared by the addition of 1 ml HCl in diethyl ether to the solution of the free base in dichloromethane (40 mg, 0.11 mmol, 61% yield). MH$^+$=344 and 345

$^1$H NMR (HCl salt) δ (MeOD, 400 MHz): 1.2 (3H, t), 2.0 (4H, m), 2.1 (4H, m), 2.4 (3H, s), 2.8 (2H, s) 3.4 (2H, m), 3.6 (2H, m), 3.8 (2H, m), 4.0 (2H, m), 4.6 (1H, s), 6.9 (1H, d), 7.0 (1H, d), 7.2 (1H, s).

Example 13

6-Methyl-1-[1-(4-propyltetrahydro-2H-pyran-4-yl)-4-piperidinyl]-1,3-dihydro-2H-benzimidazol-2-one hydrochloride (E13)

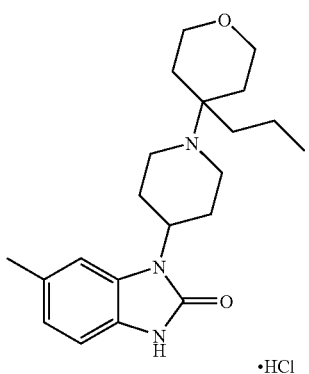

E13

·HCl

A stirred solution of 2M propylmagnesium chloride in diethyl ether (2 ml, 4 mmol), was treated with a tetrahydrofuran (5 ml) solution of 4-[4-(6-methyl-2-oxo-2,3-dihydro-1H-benzimidazol-1-yl)-1-piperidinyl]tetrahydro-2H-pyran-4-carbonitrile (D43, 0.080 g, 0.23 mmol) under argon at room temperature for 20 h. The reaction mixture was cooled to 0° C. and 1M NH$_4$Cl solution (7 ml) was added dropwise. The mixture was partially concentrated, then extracted with dichloromethane (10 ml, 3 times). The organic layer was dried (MgSO$_4$) and concentrated to leave a solid. The hydrochloride salt was prepared by the addition of 1 ml of HCl in diethyl ether to the solution of the free base in dichloromethane (24 mg, 0.07 mmol, 41% yield). MH$^+$=358 and 359

$^1$H NMR (HCl salt) δ (MeOD, 400 MHz): 1.1 (3H, t), 1.6 (2H, m), 2.0 (6H, m), 2.1 (2H, m), 2.4 (3H, s), 2.9 (2H, s) 3.3

(2H, m), 3.6 (2H, m), 3.8 (2H, m), 4.0 (2H, m), 4.6 (1H, s), 6.9 (1H, d), 7.0 (1H, d), 7.3 (1H, s).

Example 14

1-[1-(4-Methyltetrahydro-2H-pyran-4-yl)piperidin-4-yl]-6-(trifluoromethoxy)-1,3-dihydro-2H-benzimidazol-2-one hydrochloride (E14)

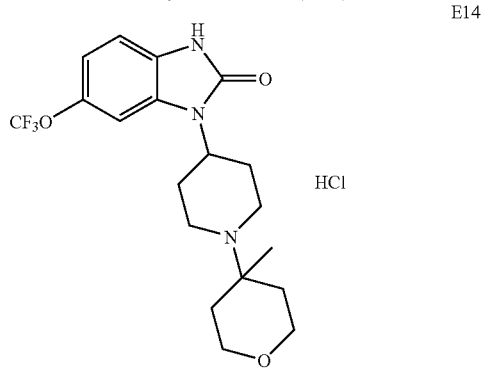

4-{4-[2-Oxo-6-(trifluoromethoxy)-2,3-dihydro-1H-benzimidazol-1-yl]piperidin-1-yl}tetrahydro-2H-pyran-4-carbonitrile (D36, 62 mg) in tetrahydrofuran (5 ml) was treated with 3M methylmagnesium bromide solution in tetrahydrofuran (0.3 ml) and stirred for 2 hours. A second aliquot of 3M methylmagnesium bromide solution in tetrahydrofuran (0.3 ml) was added and the solution was stirred for 2 hours, then treated with saturated ammonium chloride solution (3 ml). The mixture was treated with dichloromethane and water. The dichloromethane layer was separated, dried by passing through a 3 g hydromatrix cartridge and the solvent was removed. The residue was dissolved in methanol and treated with hydrogen chloride in ether to give a white solid which partitioned between dichloromethane and sodium bicarbonate solution. The dichloromethane layer was separated, dried by passing through a hydromatrix cartridge and the solvent was removed. The residue was treated with hydrogen chloride in ether to give the title compound as a white solid (28 mg). M+ 400.

$^1$H NMR (HCl salt) δ (d$^6$DMSO): 1.86 (3H, s), 2.3 (2H, m), 2.45 (4H, m), 3.25 (2H, m), 3.62 (2H, m), 3.9 (2H, d), 4.1 (2H, m), 4.35 (2H, m), 5.1 (1H, m), 7.50 (1H, d), 7.54 (1H, d), 8.07 (1H, s), 10.25 (1H, s), 11.65 (1H, s).

$^{19}$F NMR δ (d$^6$DMSO): 56.57.

Example 15

6-Cyclopropyl-1-[1-(4-methyltetrahydro-2H-pyran-4-yl)-4-piperidinyl]-1,3-dihydro-2H-benzimidazol-2-one (E15)

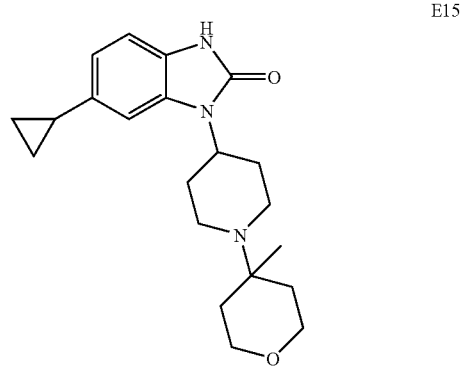

Using a similar method to Example 14 and starting with D42, the title compound was prepared and isolated as a colourless powder as the free base.

$^1$H NMR (free base) δ(CDCl$_3$): 0.68 (2H, m), 0.96 (2H, m), 1.57 (2H, m), 1.71 (3H, s), 1.85 (4H, m), 1.96 (1H, m), 2.25-2.44 (4H, m), 3.11 (2H, d), 3.57 (2H, m), 3.92 (2H, m), 4.62 (1H, m), 6.73 (1H, d), 6.96 (1H, d), 7.04 (1H, s), 9.13 (1H, s).

Example 16

6-Cyclopropyl-1-[1-(tetrahydro-2H-pyran-4-yl)-4-piperidinyl]-1,3-dihydro-2H-benzimidazol-2-one hydrochloride (E16)

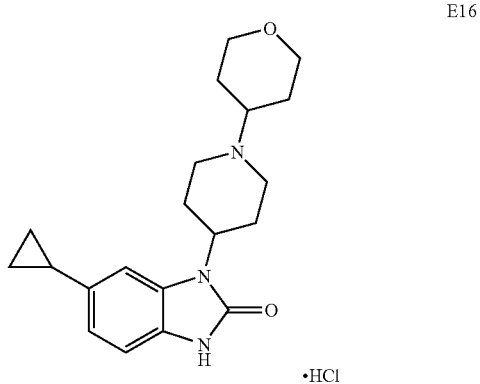

To a stirred solution of 4-cyclopropyl-N$^2$-[1-(tetrahydro-2H-pyran-4-yl)-4-piperidinyl]-1,2-benzenediamine (D45, 110 mg, 0.35 mmol) in anhydrous tetrahydrofuran (15 ml) was added N,N'-carbonyldiimidazole (113 mg, 0.70 mmol) and the mixture was stirred at room temperature for 1 hr followed by heating under reflux for 18 hrs. The mixture was cooled, diluted with ethyl acetate and washed with water (×2) and brine (×2), then dried (MgSO$_4$) and concentrated under vacuum. The residue was purified by silica gel chromatography eluting with 1-10% methanol/dichloromethane to afford the title compound as a cream coloured powder (79 mg, 66%). This was converted to its HCl salt which was also obtained as a cream coloured powder. M$^+$+H=342.3.

$^1$H NMR (free base) δ (CDCl$_3$, 400 MHz): 0.65-0.70 (2H, m), 0.90-1.00 (2H, m), 1.60-1.90 (6H, m), 1.90-2.00 (1H, m), 2.32-2.50 (4H, m), 2.50-2.63 (1H, m), 3.15 (2H, d), 3.40 (2H, t), 4.07 (2H, dd), 4.30-4.40 (1H, m), 6.74 (1H, dd), 6.95 (1H, d), 7.09 (1H, s), 9.08 (1H, s).

Example 17

6-[(1-Methylethyl)oxy]-1-[1-(tetrahydro-2H-pyran-4-yl)-4-piperidinyl]-1,3-dihydro-2H-benzimidazol-2-one hydrochloride (E17)

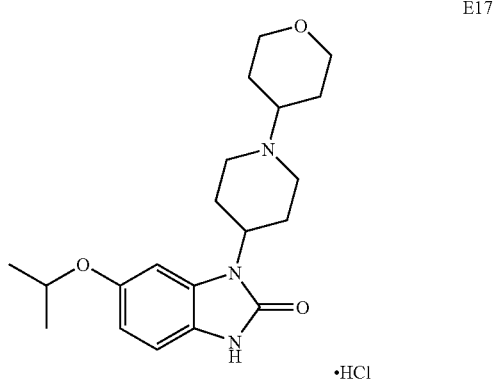

A solution of 6-[(1-methylethyl)oxy]-1-(4-piperidinyl)-1,3-dihydro-2H-benzimidazol-2-one (D50, 229 mg, 0.89 mmol) in dichloromethane (10 ml) was treated with tetrahydro-4H-pyran-4-one (623 mg, 6.23 mmol), sodium triacetoxyborohydride (1.3 g, 6.23 mmol) and triethylamine (270 mg, 3.67 mmol) and stirred at room temperature for 2 hrs. The mixture was diluted with dichloromethane, then aqueous NaOH solution (pH12) was added and the organic layer separated. The NaOH solution was extracted with dichloromethane (×2) and the combined dichloromethane extracts was washed with aqu, NaOH solution, dried (MgSO$_4$) and concentrated under vacuum to leave a pale orange oil, which was purified by chromatography on silica gel eluting with 0-50% of 10% methanol/dichloromethane: dichloromethane to afford the title compound as a pale orange solid (101 mg, 33%). M$^+$+H=360.2 which was converted to its HCl salt.

$^1$H NMR (HCl salt) ≈(d$^6$DMSO, 400 MHz): 1.23 (6H, d), 1.67-1.82 (2H, m), 1.88 (2H, br d), 2.04 (2H, br d), 2.74-2.90 (2H, m), 3.02-3.26 (2H, m), 3.28-3.50 (assumed 3H, m), 3.59 (2H, br d), 3.99 (2H, dd), 4.50-4.63 (1H, m), 4.65-4.75 (1H, m), 6.56 (1H, dd), 6.86 (1H, d), 7.19 (1H, d), 10.65 (1H, brs), 10.71 (1H, s).

Example 18

6-[(Difluoromethyl)oxy]-1-[1-(tetrahydro-2H-pyran-4-yl)-4-piperidinyl]-1,3-dihydro-2H-benzimidazol-2-one hydrochloride (E18)

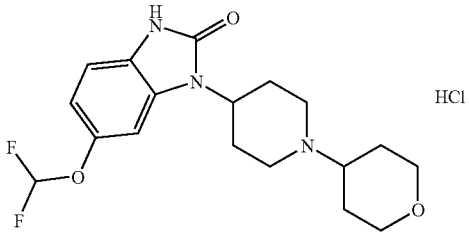

E18

6-[(Difluoromethyl)oxy]-1-(4-piperidinyl)-1,3-dihydro-2H-benzimidazol-2-one hydrochloride (D54, 0.3 g) 1,2-dichloroethane (10 ml) and triethylamine (0.5 ml), tetrahydro-4H-pyran-4-one (0.6 g), sodium triacetoxyborohydride (0.6 g) was stirred at room temperature over 3 days. The mixture was poured into sodium bicarbonate solution and extracted with dichloromethane. The organic phase was separated, washed with brine and the solvent was removed and the residue was chromatographed on silica gel eluted with dichloromethane/2M ammonia in methanol 0-10%. The resulting product was dissolved in a mixture of methanol and dichloromethane, treated with 1M hydrogen chloride in ether and the solvent was removed. Recrystallisation from methanol gave the title compound as a white solid (0.26 g). Mass Spectrum 368 M+H+

$^1$H NMR (HCl salt) ≈(d$^6$DMSO, 400 MHz): 1.76 (2H, m), 1.94 (2H, m), 2.03 (2H, m), 2.81 (2H, m), 3.22 (2H, m), 3.33 (2H, m), 3.37 (1H, m), 3.64 (2H, m), 3.98 (2H, m), 4.60 (1H, m), 6.82 (1H, d of d), 7.01 (1H, d), 6.85 (1H, s), 7.56 (1H, s), 10.63 (1H, s broad), 11.2 (1H, s).

Example 19

1-[1-(Tetrahydro-2H-pyran-4-yl)-4-piperidinyl]-6-[(2,2,2-trifluoroethyl)oxy]-1,3-dihydro-2H-benzimidazol-2-one hydrochloride (E19)

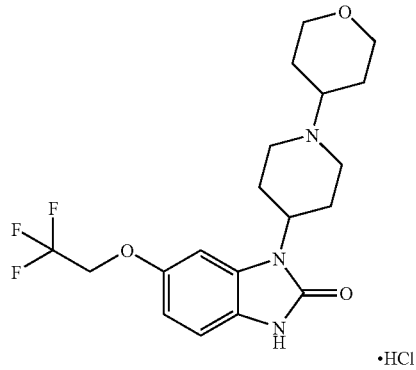

E19

A stirred solution of N$^2$-[1-(tetrahydro-2H-pyran-4-yl)-4-piperidinyl]-4-[(2,2,2-trifluoroethyl)oxy]-1,2-benzenediamine (D57, 95 mg, 0.25 mmol) in tetrahydrofuran (5 ml) at room temperature under argon was treated with N,N-diisopropylethylamine (100 mg, 0.78 mmol) followed by ethyl chloroformate (33 mg, 0.30 mmol) and maintained for 3 days. The mixture was concentrated under vacuum and the residue treated with dimethylformamide (5 ml) and heated at 150° C. under argon for 7 hrs. The solution was concentrated under vacuum and the residue treated with 10% Na$_2$CO$_3$ solution and extracted with ethyl acetate. The extract was dried (Na$_2$SO$_4$) and concentrated under vacuum to leave a brown oil, which was purified by Mass-Directed Automated HPLC to afford the title compound as a white solid. This was converted to its HCl salt and isolated as a beige solid (30 mg, 29%).

$^1$H NMR (free base) δ (CDCl$_3$, 400 MHz): 1.48-1.72 (2H, m), 1.72-1.94 (4H, m), 2.30-2.50 (4H, m), 2.52-2.62 (1H, m), 3.12 (2H, br d), 3.41 (2H, t), 4.08 (2H, dd), 4.27-4.42 (3H, m), 6.64 (1H, dd), 6.97-7.04 (2H, m), 9.55 (1H, br s).

Example 20

2-Oxo-3-[1-(tetrahydro-2H-pyran-4-yl)-4-piperidinyl]-2,3-dihydro-1H-benzimidazole-5-carbonitrile hydrochloride (E20)

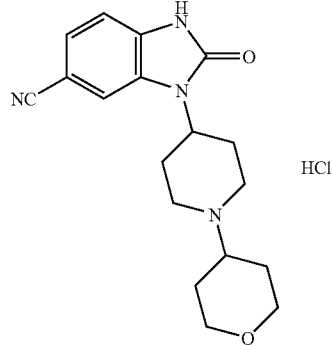

E20

4-Amino-3-{[1-(tetrahydro-2H-pyran-4-yl)-4-piperidinyl]amino}benzonitrile (D59, 240 mg, 0.0008 mol, 1 eq), diisopropylethylamine (140 mg, 0.00104 mol, 1.3 eq), triphosgene (70 mg, 0.00024 mol, 0.3 eq), and dichloroethane (20 ml) were combined. After 5 min, 4 ml of 4M HCl in dioxane were added, the reaction evaporated, the residue dissolved in methanol and purified exactly as in Example 1, where A=$H_2O$ and B=$CH_3CN$ to produce the title compound as a white solid. MS (ESI): 327 [M+H]+.

$^1$H NMR (HCl salt) d ($d^6$DMSO, 400 MHz): 11.58 (s, 1H), 10.82 (br s, 1H), 8.07 (s, 1H), 7.48 (d, J=8.0 Hz, 1H), 7.16 (d, J=8.0 Hz, 1H), 4.64 (m, 1H), 4.00 (m, 2H), 3.60 (m, 2H), 3.47 (m, 1H), 3.35 (m, 2H), 3.20 (m, 2H), 2.83 (m, 2H), 2.04 (m, 2H), 1.94 (m, 2H), 1.76 (m, 2H).

All 1H NMR are consistent with the structures shown.

All publications, including but not limited to patents and patent applications, cited in this specification are herein incorporated by reference as if each individual publication were specifically and individually indicated to be incorporated by reference herein as though fully set forth.

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims.

The invention claimed is:

1. A compound of formula (I) or a salt thereof:

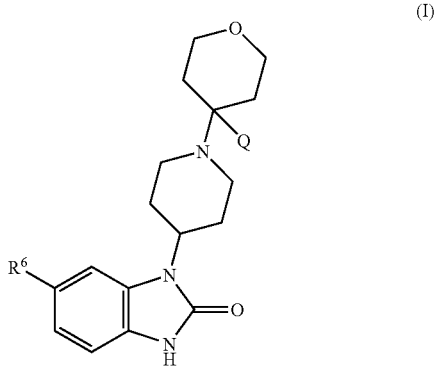

(I)

wherein
R$^6$ is selected from hydrogen, halogen, C$_{1-6}$alkyl, C$_{1-6}$alkyl substituted with one or more fluorine atoms, C$_{3-6}$cycloalkyl, C$_{3-6}$cycloalkyl substituted with one or more fluorine atoms, C$_{1-6}$ alkoxy, C$_{1-6}$ alkoxy substituted with one or more fluorine atoms, and cyano, and
Q is hydrogen or C$_{1-6}$alkyl.

2. A compound as claimed in claim 1 wherein R$^6$ is selected from chloro, bromo, methyl, ethyl, isopropyl, methoxy, trifluoromethoxy and trifluoromethyl.

3. A compound as claimed in claim 1 wherein Q is selected from hydrogen, methyl, ethyl and propyl.

4. A compound as claimed in claim 1 which is selected from:
1-[1-(Tetrahydro-2H-pyran-4-yl)-4-piperidinyl]-1,3-dihydro-2H-benzimidazol-2-one
6-Fluoro-1-[1-(tetrahydro-2H-pyran-4-yl)-4-piperidinyl]-1,3-dihydro-2H-benzimidazol-2-one
6-Chloro-1-[1-(tetrahydro-2H-pyran-4-yl)-4-piperidinyl]-1,3-dihydro-2H-benzimidazol-2-one
6-Bromo-1-[1-(tetrahydro-2H-pyran-4-yl)-4-piperidinyl]-1,3-dihydro-2H-benzimidazol-2-one
6-Methyl-1-[1-(tetrahydro-2H-pyran-4-yl)-4-piperidinyl]-1,3-dihydro-2H-benzimidazol-2-one
6-(Methoxy)-1-[1-(tetrahydro-2H-pyran-4-yl)-4-piperidinyl]-1,3-dihydro-2H-benzimidazol-2-one
1-[1-(Tetrahydro-2H-pyran-4-yl)-4-piperidinyl]-6-(trifluoromethyl)-1,3-dihydro-2H-benzimidazol-2-one
6-Ethyl-1-[1-(tetrahydro-2H-pyran-4-yl)-4-piperidinyl]-1,3-dihydro-2H-benzimidazol-2-one
1-[1-(Tetrahydro-2H-pyran-4-yl)-4-piperidinyl]-6-[(trifluoromethyl)oxy]-1,3-dihydro-2H-benzimidazol-2-one
6-(1-Methylethyl)-1-[1-(tetrahydro-2H-pyran-4-yl)-4-piperidinyl]-1,3-dihydro-2H-benzimidazol-2-one
6-Methyl-1-[1-(4-methyltetrahydro-2H-pyran-4-yl)-4-piperidinyl]-1,3-dihydro-2H-benzimidazol-2-one
1-[1-(4-Ethyltetrahydro-2H-pyran-4-yl)-4-piperidinyl]-6-methyl-1,3-dihydro-2H-benzimidazol-2-one
6-Methyl-1-[1-(4-propyltetrahydro-2H-pyran-4-yl)-4-piperidinyl]-1,3-dihydro-2H-benzimidazol-2-one
1-[1-(4-Methyltetrahydro-2H-pyran-4-yl)piperidin-4-yl]-6-(trifluoromethoxy)-1,3-dihydro-2H-benzimidazol-2-one
6-Cyclopropyl-1-[1-(4-methyltetrahydro-2H-pyran-4-yl)-4-piperidinyl]-1,3-dihydro-2H-benzimidazol-2-one
6-Cyclopropyl-1-[1-(tetrahydro-2H-pyran-4-yl)-4-piperidinyl]-1,3-dihydro-2H-benzimidazol-2-one
6-[(1-Methylethyl)oxy]-1-[1-(tetrahydro-2H-pyran-4-yl)-4-piperidinyl]-1,3-dihydro-2H-benzimidazol-2-one
6-[(Difluoromethyl)oxy]-1-[1-(tetrahydro-2H-pyran-4-yl)-4-piperidinyl]-1,3-dihydro-2H-benzimidazol-2-one
1-[1-(Tetrahydro-2H-pyran-4-yl)-4-piperidinyl]-6-[(2,2,2-trifluoroethyl)oxy]-1,3-dihydro-2H-benzimidazol-2-one
2-Oxo-3-[1-(tetrahydro-2H-pyran-4-yl)-4-piperidinyl]-2,3-dihydro-1H-benzimidazole-5-carbonitrile
and salts thereof.

5. A pharmaceutical composition comprising a compound as claimed in claim 1 and a pharmaceutically acceptable carrier thereof.

6. A method of treating a psychotic disorder or cognitive impairment, which comprises administering to a mammal in need thereof an effective amount of a compound as claimed in claim 1.

7. A process for preparing a compound of formula (I) or a salt thereof as defined in claim 1, which process is selected from:

process (A1) which comprises coupling a compound of formula (II)

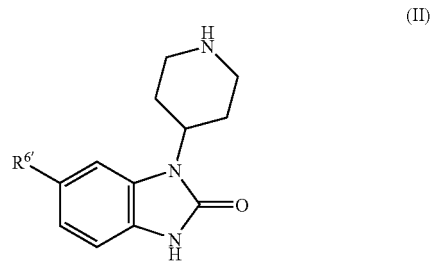

(II)

with a compound of formula (III)

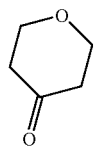
(III)

wherein
R⁶' is a group R⁶ as defined in claim 1, or a group convertible to R⁶; under conditions suitable for reductive alkylation; and process (A2) which comprises reacting a compound of formula (II) with a compound of formula (III) in the presence of a source of cyanide to form the cyano intermediate (XXXX) which can be reacted with an alkyl Grignard reagent QMgX to form compounds of formula (I)

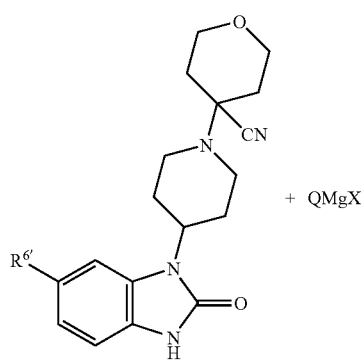
(XXXX)

+ QMgX wherein R⁶' is a group R⁶ as defined in claim 1, or a group convertible to R⁶, and Q is hydrogen or $C_{1-6}$alkyl under conditions suitable for Grignard reactions; and process (B) which comprises coupling a compound of formula (IV)

(IV)

with a compound of formula (V)

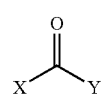
(V)

wherein R⁶' is a group R⁶ as defined in claim 1, or a group convertible to R⁶, Q is hydrogen or $C_{1-6}$alkyl; and X and Y both represent leaving groups optionally in an inert solvent, optionally in the presence of a base, and optionally with heating; and process (C) which comprises treatment of a compound of formula (VI)

(VI)

with a palladium or copper catalyst (VII) to effect an intramolecular cyclisation, wherein R⁶' is a group R⁶ as defined in claim 1, or a group convertible to R⁶, Q is hydrogen or $C_{1-6}$alkyl; and Z is a leaving group such as bromo, iodo, chloro or triflate; and process (D) which comprises coupling a compound of formula (VIII)

(VIII)

with a compound of formula (IX)

(IX)

wherein R⁶' is a group R⁶ as defined in claim 1, or a group convertible to R⁶, Q is hydrogen or $C_{1-6}$alkyl; and R is a C1-5 alkyl group by heating in an inert solvent, for example xylene, followed by reduction of the piperidine double bond; and process (E) which comprises reaction of a compound of formula (X)

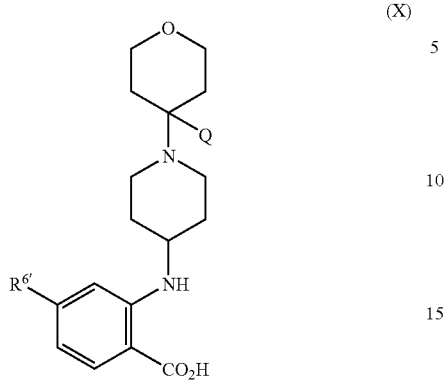

(X)

with a reagent/combination of reagents to effect the Curtius rearrangement of compound (X), followed by intramolecular cyclisation; wherein $R^{6'}$ is a group $R^6$ as defined in claim 1, or a group convertible to $R^6$, and Q is hydrogen or $C_{1-6}$alkyl; and process (F) which comprises coupling a compound of formula (XI)

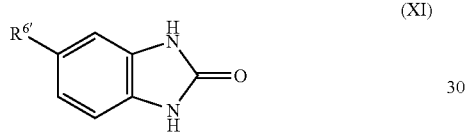

(XI)

with a compound of formula (XII)

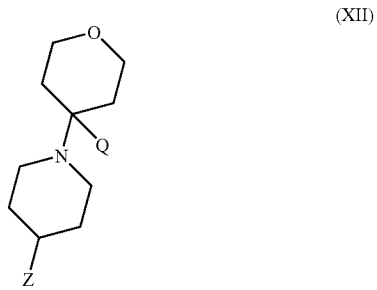

(XII)

wherein $R^{6'}$ is a group $R^6$ as defined in claim 1, or a group convertible to $R^6$, Q is hydrogen or $C_{1-6}$alkyl; and Z is hydroxy or a leaving group under alkylation or Mitsunobu reaction conditions;

and optionally thereafter, for any of the above processes:

removing any protecting groups; and/or converting a compound of formula (I) or a salt thereof to another compound of formula (I) or a salt thereof.

\* \* \* \* \*